(12) United States Patent
Price et al.

(10) Patent No.: US 10,322,028 B2
(45) Date of Patent: Jun. 18, 2019

(54) METHOD AND APPARATUS FOR SENSING POSITION BETWEEN LAYERS OF AN EYE

(71) Applicant: ORBIT BIOMEDICAL LIMITED, London (GB)

(72) Inventors: Daniel W. Price, Loveland, OH (US); Brendan J. Oberkircher, Cincinnati, OH (US); Saeed Sokhanvar, Belmont, MA (US); Daniel J. Yasevac, Somerville, MA (US); Michel Bruehwiler, Newton, MA (US); Leah R. Soffer, Somerville, MA (US); Gregory W. Johnson, Milford, OH (US); William D. Dannaher, Cincinnati, OH (US); Stefan Troller, Sissach (CH); Urban Schnell, Münchenbuchsee (CH); Jean Christophe Roulet, Lignières (CH); Alain Saurer, Bôle (CH); Michael F. Keane, Downingtown, PA (US)

(73) Assignee: ORBIT BIOMEDICAL LIMITED, London (GB)

(*) Notice: Subject to any disclaimer, the term of this patent is extended or adjusted under 35 U.S.C. 154(b) by 726 days.

(21) Appl. No.: 14/842,035

(22) Filed: Sep. 1, 2015

(65) Prior Publication Data

US 2016/0074212 A1    Mar. 17, 2016

Related U.S. Application Data

(60) Provisional application No. 62/049,079, filed on Sep. 11, 2014.

(51) Int. Cl.
*A61F 9/00* (2006.01)
*A61B 3/00* (2006.01)
(Continued)

(52) U.S. Cl.
CPC .......... *A61F 9/0008* (2013.01); *A61B 3/0041* (2013.01); *A61B 3/102* (2013.01);
(Continued)

(58) Field of Classification Search
CPC ................ A61B 3/0041; A61B 3/102; A61B 2090/3614; A61B 3/12; A61B 90/361;
(Continued)

(56) References Cited

U.S. PATENT DOCUMENTS 6,564,087 B1 *  5/2003  Pitris .................. A61B 1/00172
                                                    600/478
7,413,734 B2     8/2008  Mistry et al.
(Continued)

FOREIGN PATENT DOCUMENTS

WO    WO 2000/07530 A2    2/2000
WO    WO 2005/107845 A1   11/2005
(Continued)

OTHER PUBLICATIONS

Gao, W., et al., "Measuring Retinal Contributions to the Optical Stiles-Crawford Effect with Optical Coherence Tomography," Optics Express, 16.9 (2008): pp. 6486-6501, OSA Publishing, 16 pgs.
(Continued)

*Primary Examiner* — Brandy S Lee
(74) *Attorney, Agent, or Firm* — Frost Brown Todd LLC

(57) ABSTRACT

An apparatus for delivering therapeutic agent to an eye comprises a body, a cannula, a hollow needle, an actuation assembly, and a detection/visualization system. The cannula extends distally from the body and is sized and configured to be insertable between a choroid and a sclera of a patient's eye. The actuation assembly is operable to actuate the needle relative to the cannula to thereby drive a distal portion of the needle along an exit axis. The cannula may be inserted through a sclerotomy incision and advanced through the
(Continued)

choroid to deliver the therapeutic agent adjacent to the potential space between the neurosensory retina and the retinal pigment epithelium layer. The detection/visualization system is operable to detect or visualize penetration of the choroid of a patient's eye and provide feedback to the operator and/or automatic control of the apparatus based on penetration of the choroid.

20 Claims, 49 Drawing Sheets

(51) Int. Cl.
*A61B 3/10* (2006.01)
*A61B 3/12* (2006.01)
*G02B 3/00* (2006.01)
*A61B 90/00* (2016.01)
*A61B 90/20* (2016.01)

(52) U.S. Cl.
CPC .............. *A61B 3/12* (2013.01); *A61F 9/0017* (2013.01); *A61B 90/20* (2016.02); *A61B 90/361* (2016.02); *A61B 2090/3614* (2016.02); *G02B 3/0087* (2013.01)

(58) Field of Classification Search
CPC ............ A61B 17/0231; A61B 17/3421; A61B 17/3478; A61B 2090/3735; A61B 90/20; A61F 9/0008; A61F 9/0017; A61F 9/00736; G02B 3/0087
See application file for complete search history.

(56) References Cited

U.S. PATENT DOCUMENTS

| | | | |
|---|---|---|---|
| 2006/0030753 A1* | 2/2006 | Boutillette | A61B 1/00071 600/146 |
| 2006/0098206 A1* | 5/2006 | Kim | G01B 11/0675 356/495 |
| 2010/0173866 A1 | 7/2010 | Hee et al. | |
| 2010/0228119 A1* | 9/2010 | Brennan | A61B 5/0066 600/424 |
| 2010/0286674 A1* | 11/2010 | Ben-Yakar | A61B 5/0059 606/10 |
| 2012/0191064 A1* | 7/2012 | Conston | A61F 9/00727 604/506 |
| 2015/0223977 A1 | 8/2015 | Oberkircher et al. | |

FOREIGN PATENT DOCUMENTS

| | | |
|---|---|---|
| WO | WO 2007/087061 A2 | 8/2007 |
| WO | WO 2010/132751 A1 | 11/2010 |
| WO | WO 2015/126694 A1 | 8/2015 |

OTHER PUBLICATIONS

International Search Report and Written Opinion dated Nov. 25, 2015 for Application No. PCT/US2015/049425, 13 pgs.
U.S. Appl. No. 62/049,079, filed Sep. 11, 2014.

* cited by examiner

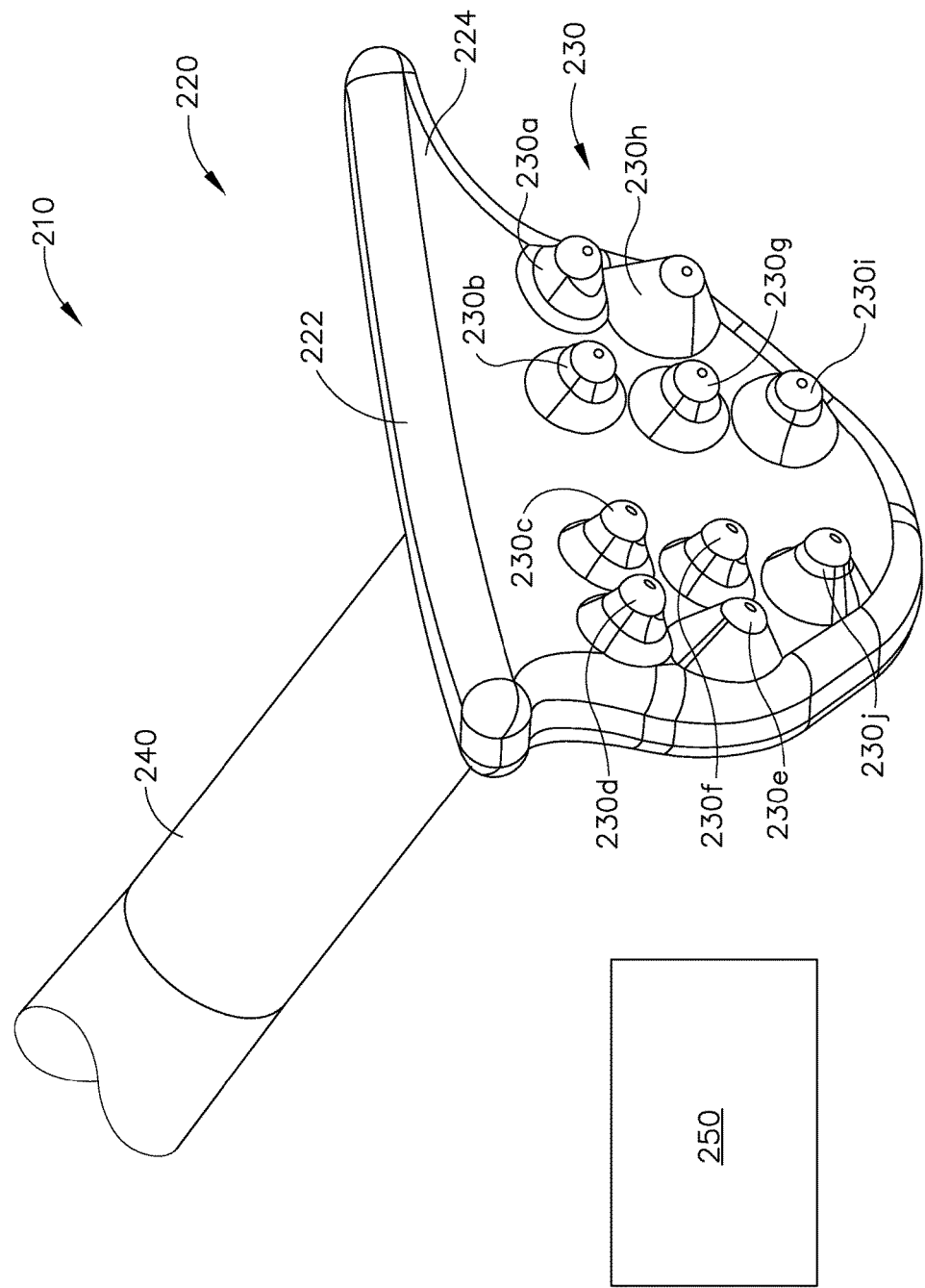

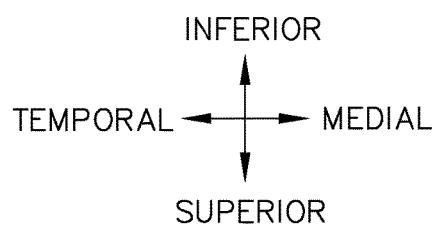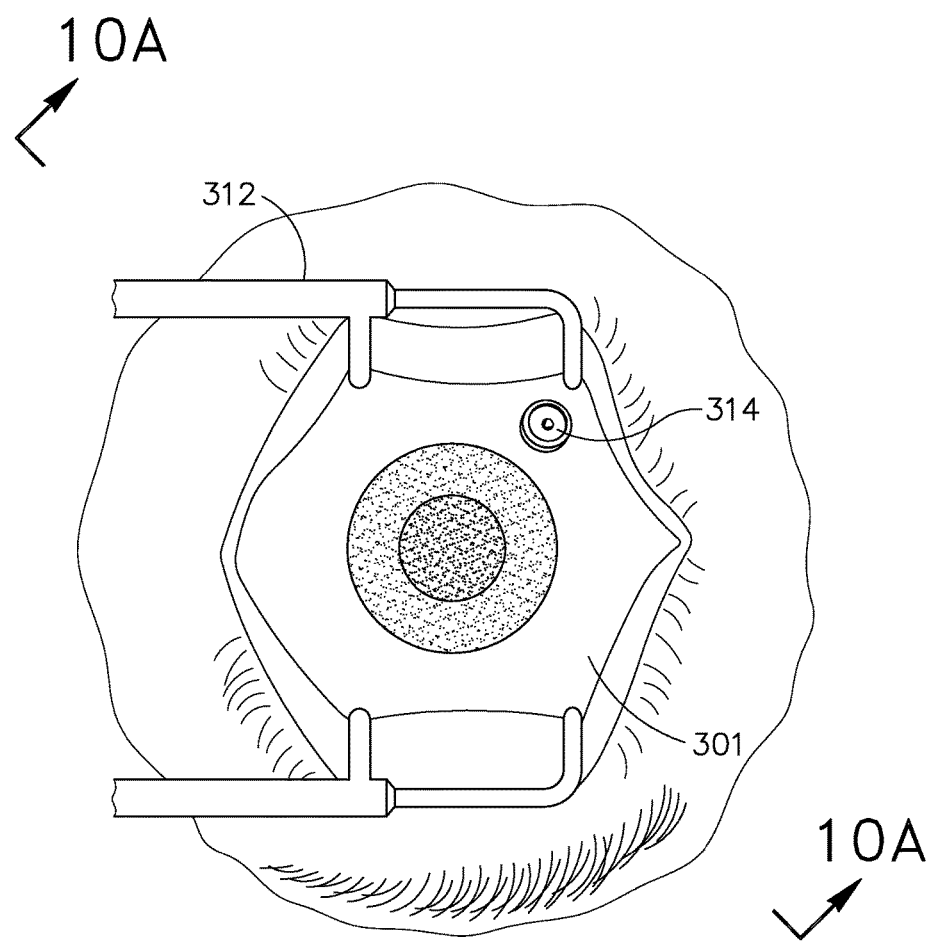
Fig.9A

US 10,322,028 B2

METHOD AND APPARATUS FOR SENSING POSITION BETWEEN LAYERS OF AN EYE

PRIORITY

This application claims priority to U.S. Provisional Patent Application No. 62/049,079, entitled "Suprachoroidal Sensing Technology," filed Sep. 11, 2014, the disclosure of which is incorporated by reference herein.

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Ethicon Endo-Surgery, Inc. and Janssen Research & Development, LLC.

BACKGROUND

The human eye comprises several layers. The white outer layer is the sclera, which surrounds the choroid layer. The retina is interior to the choroid layer. The sclera contains collagen and elastic fiber, providing protection to the choroid and retina. The choroid layer includes vasculature providing oxygen and nourishment to the retina. The retina comprises light sensitive tissue, including rods and cones. The macula is located at the center of the retina at the back of the eye, generally centered on an axis passing through the centers of the lens and cornea of the eye (i.e., the optic axis). The macula provides central vision, particularly through cone cells.

Macular degeneration is a medical condition that affects the macula, such that people suffering from macular degeneration may experience lost or degraded central vision while retaining some degree of peripheral vision. Macular degeneration may be caused by various factors such as age (also known as "AMD") and genetics. Macular degeneration may occur in a "dry" (nonexudative) form, where cellular debris known as drusen accumulates between the retina and the choroid, resulting in an area of geographic atrophy. Macular degeneration may also occur in a "wet" (exudative) form, where blood vessels grow up from the choroid behind the retina. Even though people having macular degeneration may retain some degree of peripheral vision, the loss of central vision may have a significant negative impact on the quality of life. Moreover, the quality of the remaining peripheral vision may be degraded and in some cases may disappear as well. It may therefore be desirable to provide treatment for macular degeneration in order to prevent or reverse the loss of vision caused by macular degeneration. In some cases it may be desirable to provide such treatment in a highly localized fashion, such as by delivering a therapeutic substance in the subretinal layer (under the neurosensory layer of the retina and above the retinal pigment epithelium) directly adjacent to the area of geographic atrophy, near the macula. However, since the macula is at the back of the eye and underneath the delicate layer of the retina, it may be difficult to access the macula in a practical fashion.

While a variety of surgical methods and instruments have been made and used to treat an eye, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 8 depicts a perspective view of an exemplary suture measurement template for use in an exemplary method for the subretinal administration of a therapeutic agent from a suprachoroidal approach;

FIG. 9A depicts a top plan view of an eye of a patient, with surrounding structures of the eye immobilized and a chandelier installed;

Figure 1:
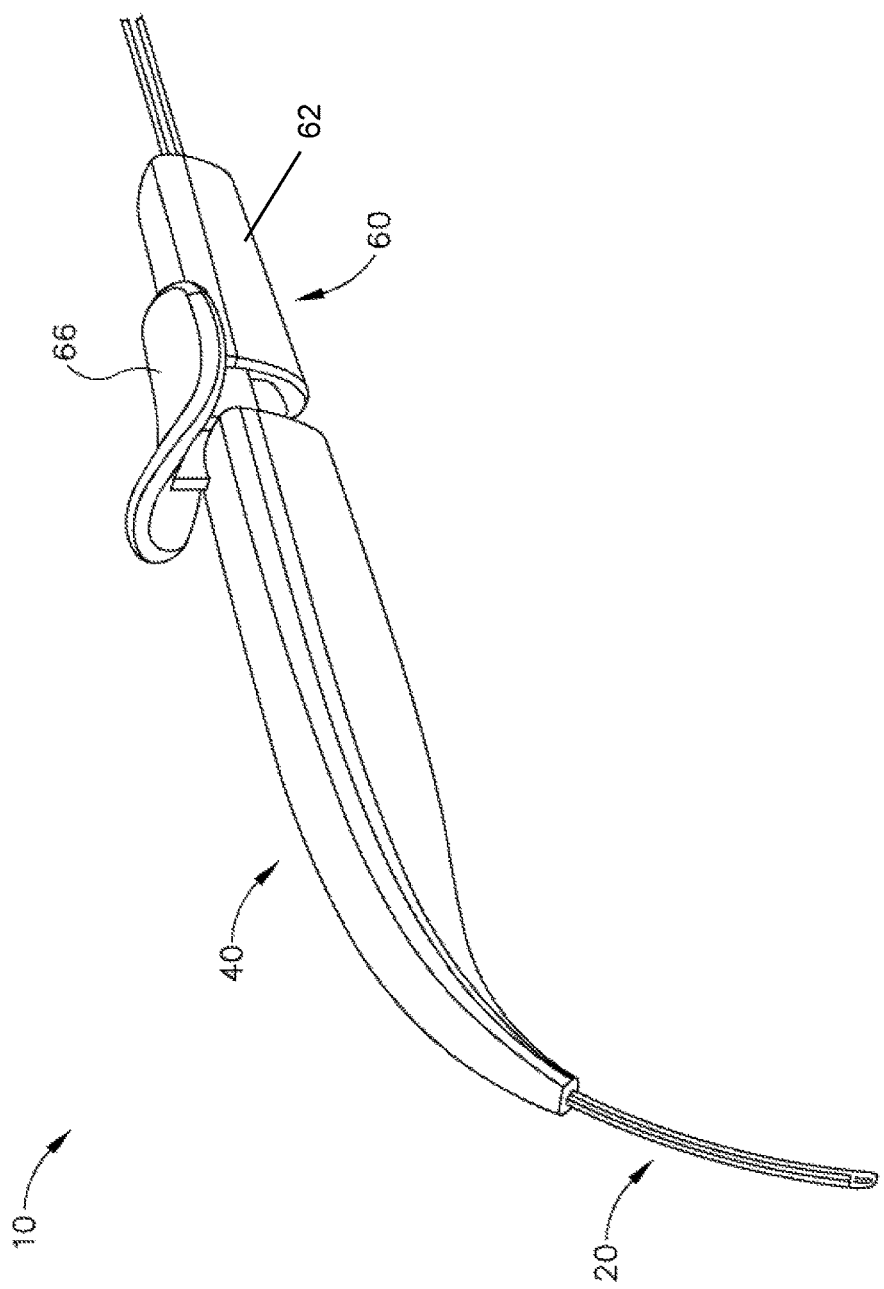
FIG. 1 depicts a perspective view of an exemplary instrument for subretinal administration of a therapeutic agent from a suprachoroidal approach.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

I. Exemplary Instrument with Slider Articulation Feature

FIGS. 1-4 show an exemplary instrument (10) that is configured for use in a procedure for the subretinal administration of a therapeutic agent to an eye of a patient from a suprachoroidal approach. Instrument (10) comprises a flexible cannula (20), a body (40), and a slidable actuation assembly (60). Cannula (20) extends distally from body (40) and has a generally rectangular cross section. Cannula (20) is generally configured to support a needle (30) that is slidable within cannula (20), as will be described in greater detail below.

In the present example, cannula (20) comprises a flexible material such as Polyether block amide (PEBA), which may be manufactured under the trade name PEBAX. Of course, any other suitable material or combination of materials may be used. Also in the present example, cannula (20) has a cross-sectional profile dimension of approximately 2.0 mm by 0.8 mm, with a length of approximately 80 mm. Alternatively, any other suitable dimensions may be used.

As will be described in greater detail below, cannula (20) is flexible enough to conform to specific structures and contours of the patient's eye, yet cannula (20) has sufficient column strength to permit advancement of cannula (20) between the sclera and choroid of patient's eye without buckling. Several factors may contribute to suitable flexibility of cannula (20). For instance, the durometer of the material used to construct cannula (20) at least partially characterizes the flexibility of cannula (20). By way of example only, the material that is used to form cannula (20) may have a shore hardness of approximately 27 D, approximately 33 D, approximately 42 D, approximately 46 D, or any other suitable shore hardness. It should be understood that the shore hardness may fall within the range of approximately 27 D to approximately 46 D; or more particularly within the range of approximately 33 D to approximately 46 D; or more particularly within the range of approximately 40 D to approximately 45 D. The particular cross-sectional shape of cannula (20) may also at least partially characterize the flexibility of cannula (20). Additionally, the stiffness of needle (30) disposed within cannula (20) may at least partially characterize the flexibility of cannula (20).

In the present example, the flexibility of cannula (20) may be quantified by calculating a flexural stiffness for cannula (20). Flexural stiffness is calculated by the product of the elastic modulus and the area moment of inertia. By way of example only, one exemplary material that may be used to form cannula (20) may have a shore hardness of D27, an elastic modulus (E) of $1.2 \times 10^7$ N/m$^2$, and an area moment of inertia ($I_x$) of $5.52 \times 10^{-14}$ m$^4$, providing a calculated flexural stiffness about the x-axis at $0.7 \times 10^{-6}$ Nm$^2$. Another exemplary material that may be used to form cannula (20) may have a shore hardness of D33, an elastic modulus (E) of $2.1 \times 10^7$ N/m$^2$, and an area moment of inertia ($I_x$) of $5.52 \times 10^{-14}$ m$^4$, providing a calculated flexural stiffness about the x-axis at $1.2 \times 10^{-6}$ Nm$^2$. Another exemplary material that may be used to form cannula (20) may have a shore hardness of D42, an elastic modulus (E) of $7.7 \times 10^7$ N/m$^2$, and an area moment of inertia ($I_x$) of $5.52 \times 10^{-14}$ m$^4$, providing a calculated flexural stiffness about the x-axis at $4.3 \times 10^{-6}$ Nm$^2$. Another exemplary material that may be used to form cannula (20) may have a shore hardness of D46, an elastic modulus (E) of $17.0 \times 10^7$ N/m$^2$, and an area moment of inertia ($I_x$) of $5.52 \times 10^{-14}$ m$^4$, providing a calculated flexural stiffness about the x-axis at $9.4 \times 10^{-6}$ Nm$^2$. Thus, by way of example only, the flexural stiffness of cannula (20) may fall within the range of approximately $0.7 \times 10^{-6}$ Nm$^2$ to approximately $9.4 \times 10^{-6}$ Nm$^2$; or more particularly within the range of approximately $1.2 \times 10^{-6}$ Nm$^2$ to approximately $9.4 \times 10^{-6}$ Nm$^2$; or more particularly within the range of approximately $2.0 \times 10^{-6}$ Nm$^2$ to approximately $7.5 \times 10^{-6}$ Nm$^2$; or more particularly within the range of approximately $2.0 \times 10^{-6}$ Nm$^2$ to approximately $6.0 \times 10^{-6}$ Nm$^2$; or more particularly within the range of approximately $3.0 \times 10^{-6}$ Nm$^2$ to approximately $5.0 \times 10^{-6}$ Nm$^2$; or more particularly within the range of approximately $4.0 \times 10^{-6}$ Nm$^2$ to approximately $5.0 \times 10^{-6}$ Nm$^2$.

In the present example, the flexibility of cannula (20) may also be quantified by the following formula:

$$\delta = \frac{FL^3}{48EI} \quad (1)$$

In the above equation, flexural stiffness (EI) is calculated experimentally by deflecting cannula (20) having a fixed span (L) a set distance to yield a predetermined amount of deflection ($\delta$). The amount of force (F) required for such a deflection may then be recorded. For instance, when using such a method cannula (20) may have a span of 0.06 m and may be deflected for a given distance. By way of example only, one exemplary material that may be used to form cannula (20) may require a force of 0.0188 N to achieve a deflection of 0.0155 m, providing a calculated flexural stiffness about the x-axis of $5.5 \times 10^{-6}$ Nm$^2$. In another exemplary material that may be used to form cannula (20) may require a force of 0.0205 N to achieve a deflection of 0.0135 m, providing a calculated flexural stiffness about the x-axis of $6.8 \times 10^{-6}$ Nm$^2$. In still another exemplary material that may be used to form cannula (20) may require a force of 0.0199 N to achieve a deflection of 0.0099 m, providing a calculated flexural stiffness about the x-axis of $9.1 \times 10^{-6}$ Nm$^2$. In yet another exemplary material that may be used to form cannula (20) may require a force of 0.0241 N to achieve a deflection of 0.0061 m, providing a calculated flexural stiffness about the x-axis of $1.8 \times 10^{-6}$ Nm$^2$. In yet another exemplary material that may be used to form cannula (20) may require a force of 0.0190 N to achieve a deflection 0.0081 m, providing a calculated flexural stiffness about the x-axis of $1.0 \times 10^{-6}$ Nm$^2$. In yet another exemplary material that may be used to form cannula (20) may require a force of 0.0215 N to achieve a deflection of 0.0114 m, providing a calculated flexural stiffness about the x-axis of $8.4 \times 10^{-6}$ Nm$^2$. In yet another exemplary material that may be used to form cannula (20) may require a force of 0.0193 N to achieve a deflection of 0.0170 m, providing a calculated flexural stiffness about the x-axis of $5.1 \times 10^{-6}$ Nm$^2$. In yet another exemplary material that may be used to form cannula (20) may require a force of 0.0224 N to achieve a deflection of 0.0152 m, providing a calculated flexural stiffness about the x-axis of $6.6 \times 10^{-6}$ Nm$^2$. In yet another exemplary material that may be used to form cannula (20) may require a force of 0.0183 N to achieve a deflection of 0.0119 m, providing a calculated flexural stiffness about the x-axis of $6.9 \times 10^{-6}$ Nm$^2$. In yet another exemplary material that may be used to form cannula (20) may require a force of 0.0233 N to achieve a deflection of 0.0147 m, providing a calculated flexural stiffness about the x-axis of $7.1\times10^{-6}$ $Nm^2$. In yet another exemplary material that may be used to form cannula (20) may require a force of 0.0192 N to achieve a deflection of 0.0122, providing a calculated flexural stiffness about the x-axis of $7.1\times10^{-6}$ $Nm^2$. In yet another exemplary material that may be used to form cannula (20) may require a force of 0.0201 N to achieve a deflection of 0.0201, providing a calculated flexural stiffness about the x-axis of $4.5\times10^{-6}$ $Nm^2$. Thus, by way of example only, the flexural stiffness of cannula (20) may fall within the range of approximately $1.0\times10^{-6}$ $Nm^2$ to approximately $9.1\times10^{-6}$ $Nm^2$. It should be understood that in other examples, the flexural stiffness of cannula may fall within the range of approximately $0.7\times10^{-6}$ $Nm^2$ to approximately $11.1\times10^{-6}$ $Nm^2$; or more particularly within the range of approximately $2.0\times10^{-6}$ $Nm^2$ to approximately $6.0\times10^{-6}$ $Nm^2$.

Needle (30) may have a flexural stiffness that differs from the flexural stiffness of cannula (20). By way of example only, needle (30) may be formed of a nitinol material that has an elastic modulus (E) of $7.9\times10^{10}$ $N/m^2$, and an area moment of inertia ($I_x$) of $2.12\times10^{-17}$ $m^4$, providing a calculated flexural stiffness about the x-axis at $1.7\times10^{-6}$ $Nm^2$. By way of further example only, the flexural stiffness of needle (30) may fall within the range of approximately $0.5\times10^{-6}$ $Nm^2$ to approximately $2.5\times10^{-6}$ $Nm^2$; or more particularly within the range of approximately $0.75\times10^{-6}$ $Nm^2$ to approximately $2.0\times10^{-6}$ $Nm^2$; or more particularly within the range of approximately $1.25\times10^{-6}$ $Nm^2$ to approximately $1.75\times10^{-6}$ $Nm^2$.

Figure 5:
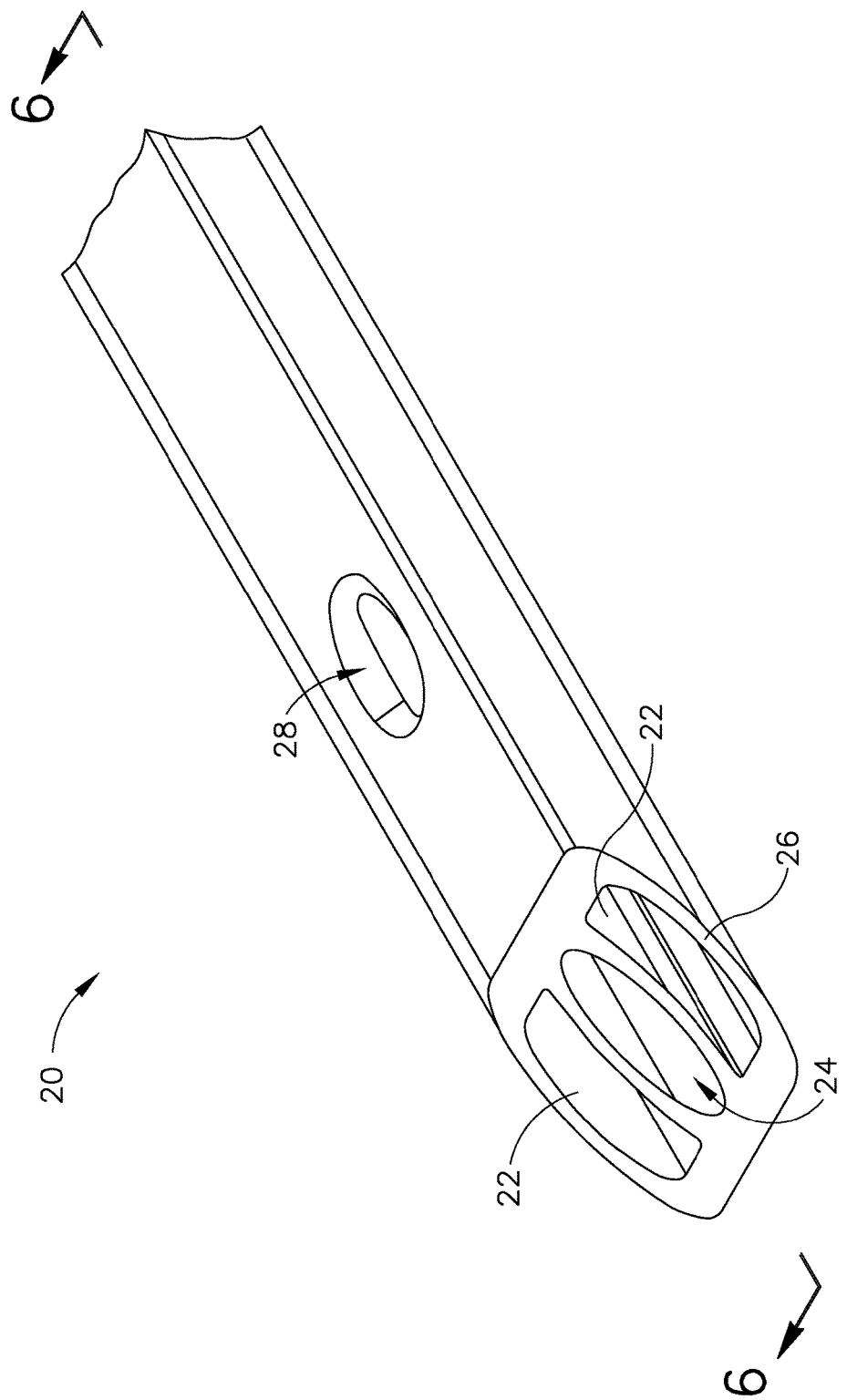
FIG. 5 depicts a perspective view of the distal end of an exemplary cannula that may be incorporated into the instrument of FIG. 1.
Figure 6:
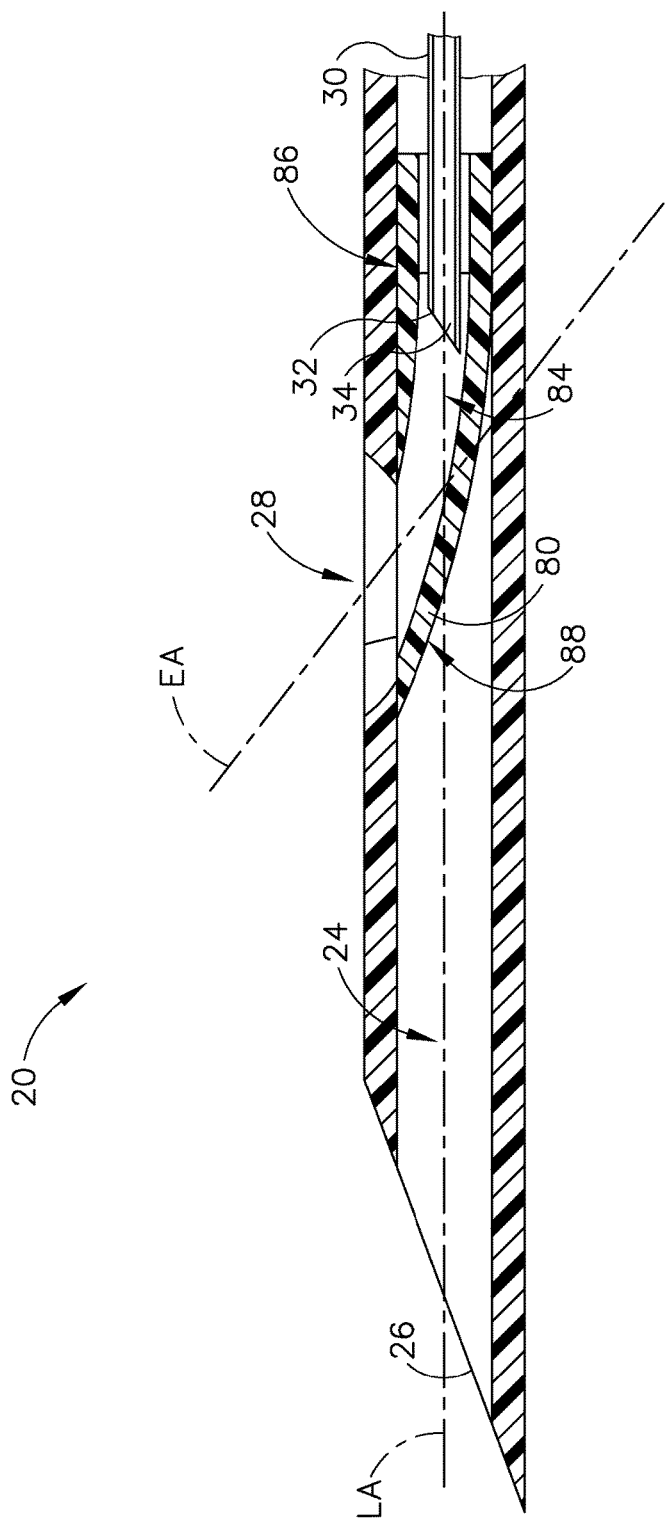
FIG. 6 depicts a cross-sectional view of the cannula of FIG. 5, with the cross-section taken along line 6-6 of FIG. 5.

As can be seen in FIGS. 5 and 6, cannula (20) comprises two side lumens (22) and a single central lumen (24) extending longitudinally through cannula (20) and terminating at an atraumatic, beveled distal end (26). A beveled lateral opening (28) is located proximal to beveled distal end (26). Side lumens (22) contribute to the flexibility of cannula (20). Although lumens (22, 24) are shown as being open at beveled distal end (26), it should be understood that in some examples, side lumens (22, 24) may be optionally closed at beveled distal end (26). As will be described in greater detail below, central lumen (24) is configured to receive needle (30) and a needle guide (80). In some versions, an optical fiber (not shown) is also disposed in central lumen (24) alongside needle (30). Such an optical fiber may be used to provide illumination and/or optical feedback as will be described in greater detail below.

Beveled distal end (26) is generally beveled to provide separation between the sclera and choroid layers to enable cannula (20) to be advanced between such layers while not inflicting trauma to the sclera or choroid layers. In the present example, beveled distal end (26) is beveled at an angle of approximately 15° relative to the longitudinal axis of cannula (20) in the present example. In other examples, beveled distal end (26) may have a bevel angle within the range of approximately 5° to approximately 50°; or more particularly within the range of approximately 5° to approximately 40°; or more particularly within the range of approximately 10° to approximately 30°; or more particularly within the range of approximately 10° to approximately 20°.

A needle guide (80) is disposed within lumen (24) such that the distal end of needle guide (80) abuts beveled lateral opening (28). Needle guide (80) is generally configured to direct needle (30) upwardly along an exit axis (EA) that is obliquely oriented relative to the longitudinal axis (LA) of cannula (20) through beveled opening (28) of cannula (20). Needle guide (80) may be formed of plastic, stainless steel, and/or any other suitable biocompatible material(s). The shape of needle guide (80) is configured for insertion into central lumen (24). In the present example, needle guide (80) is secured within central lumen (24) by a press or interference fit, although in other examples, adhesives and/or mechanical locking mechanisms may be used to secure needle guide (80).

As can best be seen in FIG. 6, needle guide (80) defines an internal lumen (84) that is configured to slidably receive needle (30). In particular, internal lumen (84) includes a generally straight proximal portion (86) and a curved distal portion (88). Straight proximal portion (86) corresponds to the longitudinal axis (LA) of cannula (20), while curved distal portion (88) curves upwardly away from the longitudinal axis of cannula (20). Curved distal portion (88) of the present example is curved to direct needle (30) along an exit axis (EA) that extends distally from cannula (20) at an angle of approximately 7° to approximately 9° relative to the longitudinal axis (LA) of cannula (20). It should be understood that such an angle may be desirable to deflect needle (30) in a direction to ensure penetration of needle into the choroid (306) and to minimize the possibility of needle (30) continuing beneath the choroid (306) through the suprachoroidal space (as opposed to penetrating through the choroid (306)) and the possibility of retinal perforation. By way of further example only, curved distal portion (88) may urge needle (30) to exit cannula (20) along an exit axis (EA) that is oriented at an angle within the range of approximately 5° to approximately 30° relative to the longitudinal axis (LA) of cannula (20); or more particularly within the range of approximately 5° to approximately 20° relative to the longitudinal axis (LA) of cannula (20); or more particularly within the range of approximately 5° to approximately 10° relative to the longitudinal axis (LA) of cannula (20).

Needle (30) is in the form of an inner cannula that has a sharp distal end (32) and defines an internal lumen (34). Distal end (32) of the present example has a lancet configuration. In some other versions, distal end (32) has a tri-bevel configuration or any other configuration as described in U.S. patent application Ser. No. 14/619,256, entitled "Method and Apparatus for Suprachoroidal Administration of Therapeutic Agent," filed Feb. 11, 2015, the disclosure of which is incorporated by reference herein. Still other suitable forms that distal end (32) may take will be apparent to those of ordinary skill in the art in view of the teachings herein. Needle (30) of the present example comprises a stainless steel hypodermic needle that is sized to deliver the therapeutic agent while being small enough to minimize incidental trauma as needle (30) penetrates tissue structures of the patient's eye, as will be described in greater detail below. While stainless steel is used in the present example, it should be understood that any other suitable material(s) may be used, including but not limited to nitinol, etc.

By way of example only, needle (30) may be 35 gauge with a 100 μm inner diameter, although other suitable sizes may be used. For instance, the outer diameter of needle (30) may fall within the range of 27 gauge to 45 gauge; or more particularly within the range of 30 gauge to 42 gauge; or more particularly within the range of 32 gauge to 39 gauge. As another merely illustrative example, the inner diameter of needle (30) may fall within the range of approximately 50 μm to approximately 200 μm; or more particularly within the range of approximately 50 μm to approximately 150 μm; or more particularly within the range of approximately 75 μm to approximately 125 μm.

Referring back to FIGS. 1-2, body (40) is generally shaped as an elongate rectangle with a curved distal end. The particular shape of body (40) that is shown is configured to be grasped by an operator. Alternatively, body (40) may be mounted on a support device or robotic arm for ease of positioning instrument (10), as described in U.S. patent application Ser. No. 14/619,256, entitled "Method and Apparatus for Suprachoroidal Administration of Therapeutic Agent," filed Feb. 11, 2015, the disclosure of which is incorporated by reference herein.

Actuation assembly (60) includes an actuation member (62) and a locking member (66). Locking member (66) is removably attachable to body engagement portion (50), between body (40) and actuation member (62). As will be described in greater detail below, locking member (66) fills a space between body (40) and actuation member (62) to prevent actuation member (62) from being advanced distally relative to body (40). However, locking member (66) can be removed to selectively permit actuation member (62) to be advanced distally relative to body (40).

Figure 2:
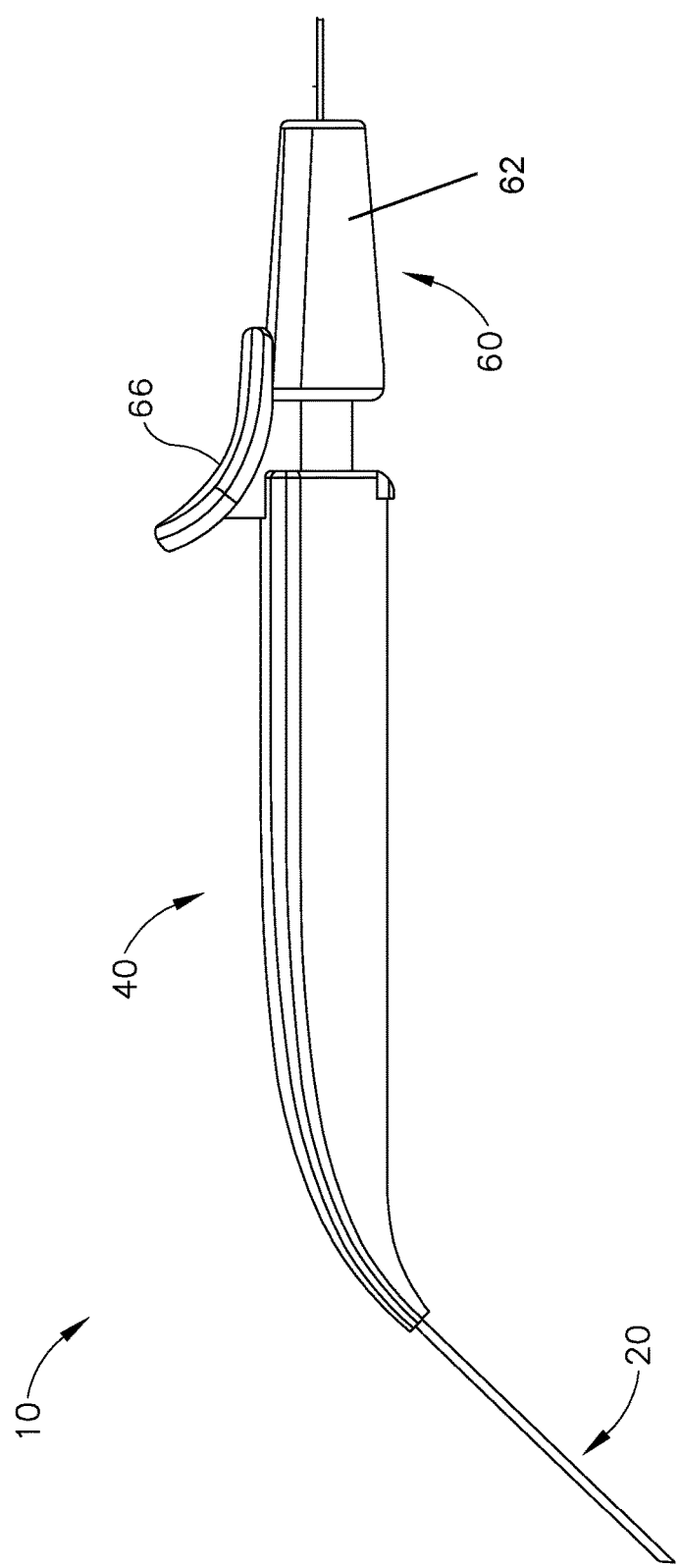
FIG. 2 depicts a side elevational view of the instrument of FIG. 1.
Figure 3:
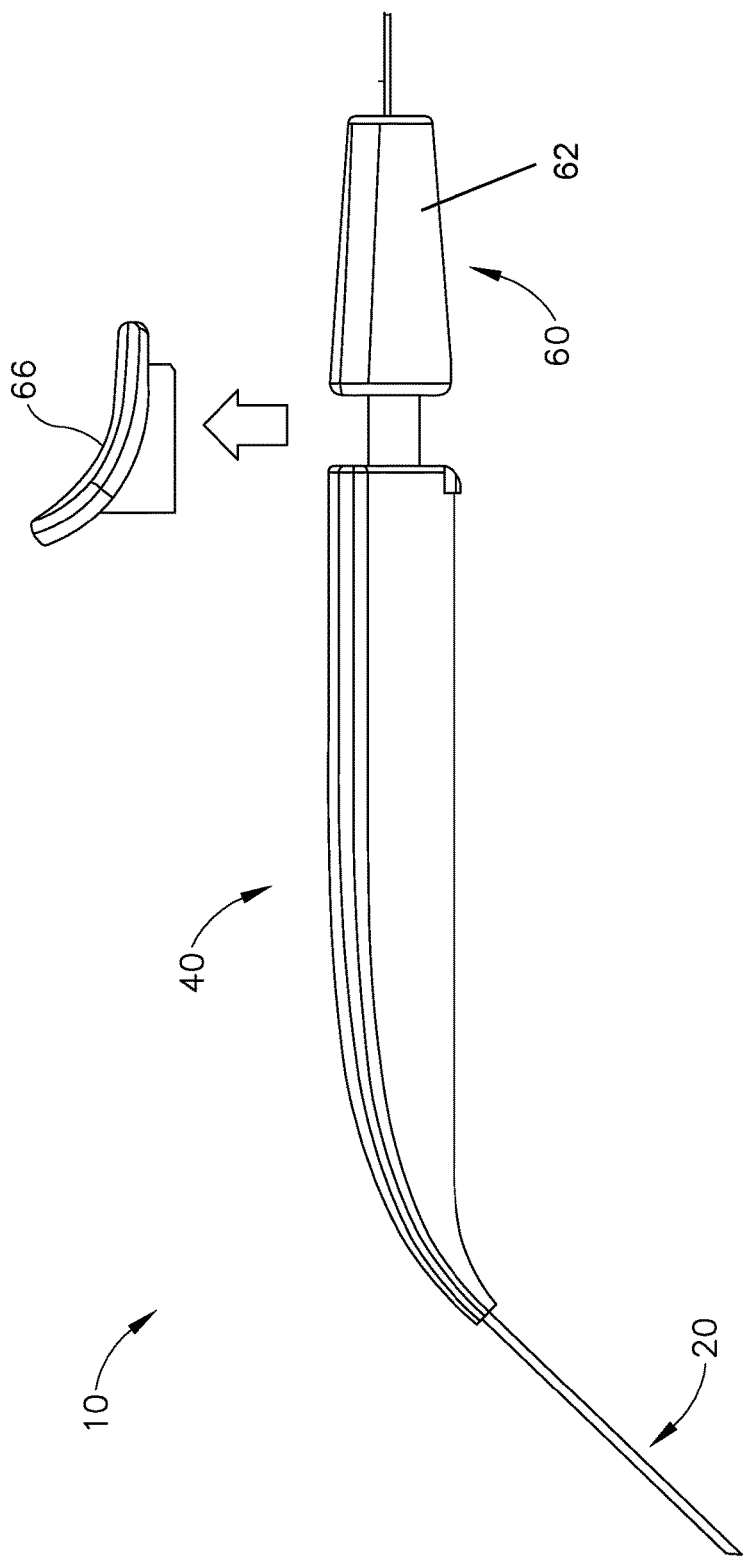
FIG. 3 depicts another side elevational view of the instrument of FIG. 1, with a locking member removed.
Figure 4:
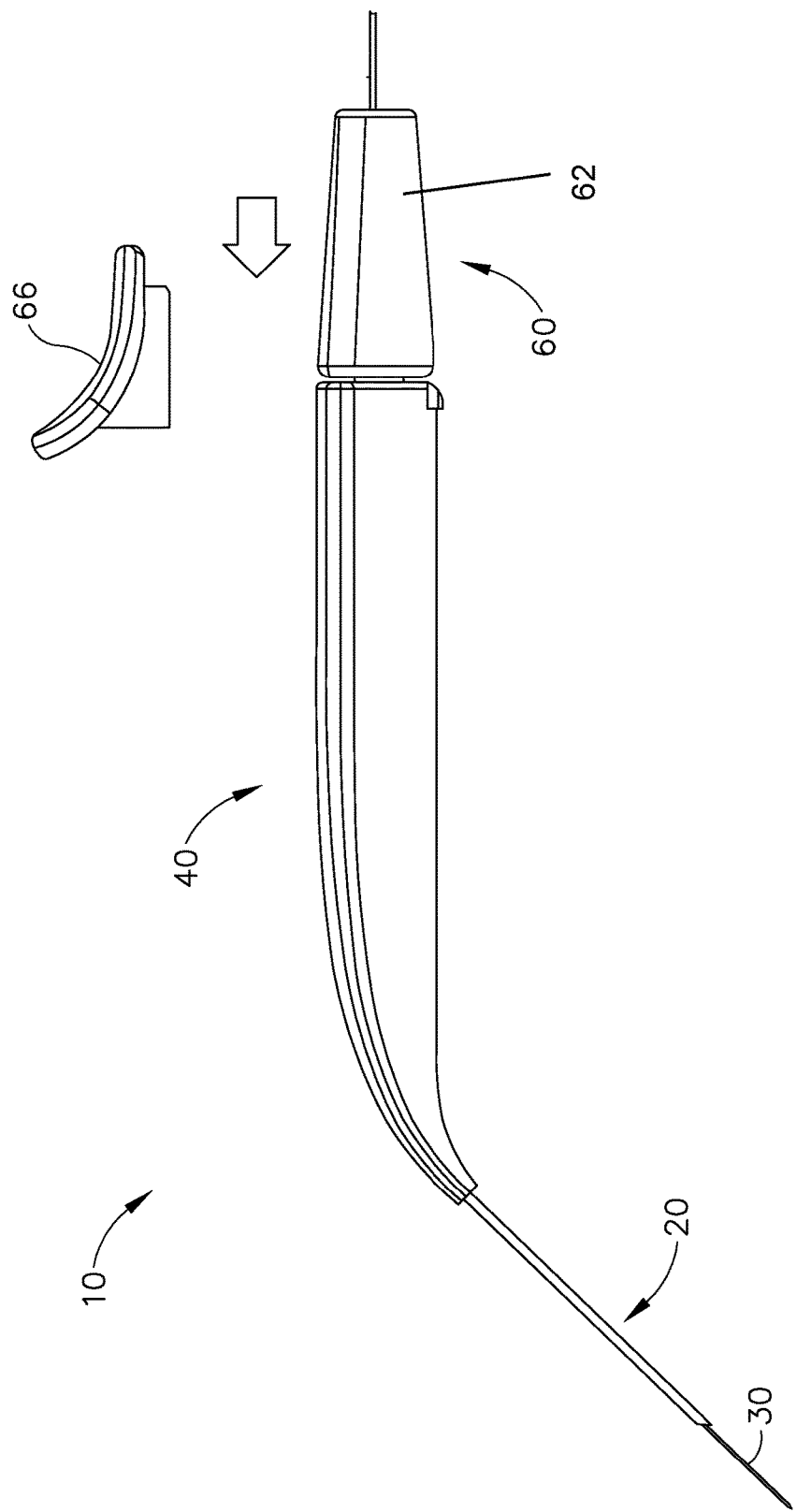
FIG. 4 depicts another side elevational view of the instrument of FIG. 1, with an actuation member advanced distally to extend the needle distally from the cannula.

FIGS. 2-4 show an exemplary actuation of instrument (10). In particular, as can be seen in FIG. 2, needle (30) is initially retracted into cannula (20) and locking member (66) is positioned between body (40) and actuation member (62), thereby preventing advancement of actuation member (62). With instrument (10) in this configuration, cannula (20) may be positioned within an eye of a patient as will be described in greater detail below.

Once cannula (20) is positioned within an eye of a patient, an operator may desire to advance needle (30) relative to cannula (20). To advance needle (30), an operator may first remove locking member (66) by pulling locking member (66) away from instrument (10), as can be seen in FIG. 3. Once locking member (66) is removed, actuation member (62) may be moved or translated relative to body (40) to advance needle (30) relative to cannula (20) as described in U.S. patent application Ser. No. 14/619,256, entitled "Method and Apparatus for Suprachoroidal Administration of Therapeutic Agent," filed Feb. 11, 2015, the disclosure of which is incorporated by reference herein. Actuation member (62) of the present example is only configured to translate needle (30) and not rotate needle (30). In other examples, it may be desirable to rotate needle (30). Accordingly, alternative examples may include features in actuation member (62) to rotate and translate needle (30).

In the present example, advancement of actuation member (62) into contact with body (40) as shown in FIG. 4 corresponds to advancement of needle (30) to a position relative to cannula (20) to a predetermined amount of penetration within an eye of a patient. In other words, instrument (10) is configured such that an operator only has to advance actuation member (62) into contact with body (40) to properly position needle (30) within an eye of a patient. In some examples, the predetermined amount of advancement of needle (30) relative to cannula (20) is between approximately 0.25 mm to approximately 10 mm; or more particularly within the range of approximately 0.1 mm to approximately 10 mm; or more particularly within the range of approximately 2 mm to approximately 6 mm; or more particularly to approximately 4 mm. In other examples, contact between actuation member (62) and body (40) may have no particular significance besides the maximum advancement of needle (30) relative to cannula (20). Instead, instrument (10) may be equipped with certain tactile feedback features to indicate to an operator when needle (30) has been advanced to certain predetermined distances relative to cannula (20). Accordingly, an operator may determine the desired depth of penetration of needle (30) into a patient's eye based on direct visualization of indicia on instrument and/or based on tactile feedback from instrument (10). Of course, such tactile feedback features may be combined with the present example, as will be apparent to those of ordinary skill in the art in view of the teachings herein.

II. Exemplary Alternative Instruments and Features

In some examples, it may be desirable to vary certain components or features of the instruments described herein. For instance, it may be desirable to utilize instruments similar to instrument (10) with alternative mechanisms to actuate needle (30). Yet in other examples, it may be desirable to utilize instruments similar to instrument (10) equipped with different cannula (20) or needle (30) geometries. Instruments having the above referenced variations may be desirable for different surgical procedures, or surgical procedures similar to the procedure discussed above, to engage tissue structures having varying physical properties. While certain examples of variations are described herein, it should be understood that the instruments described herein may include any other alternative features as will be apparent to those of ordinary skill in the art in view of the teachings herein.

Figure 7:
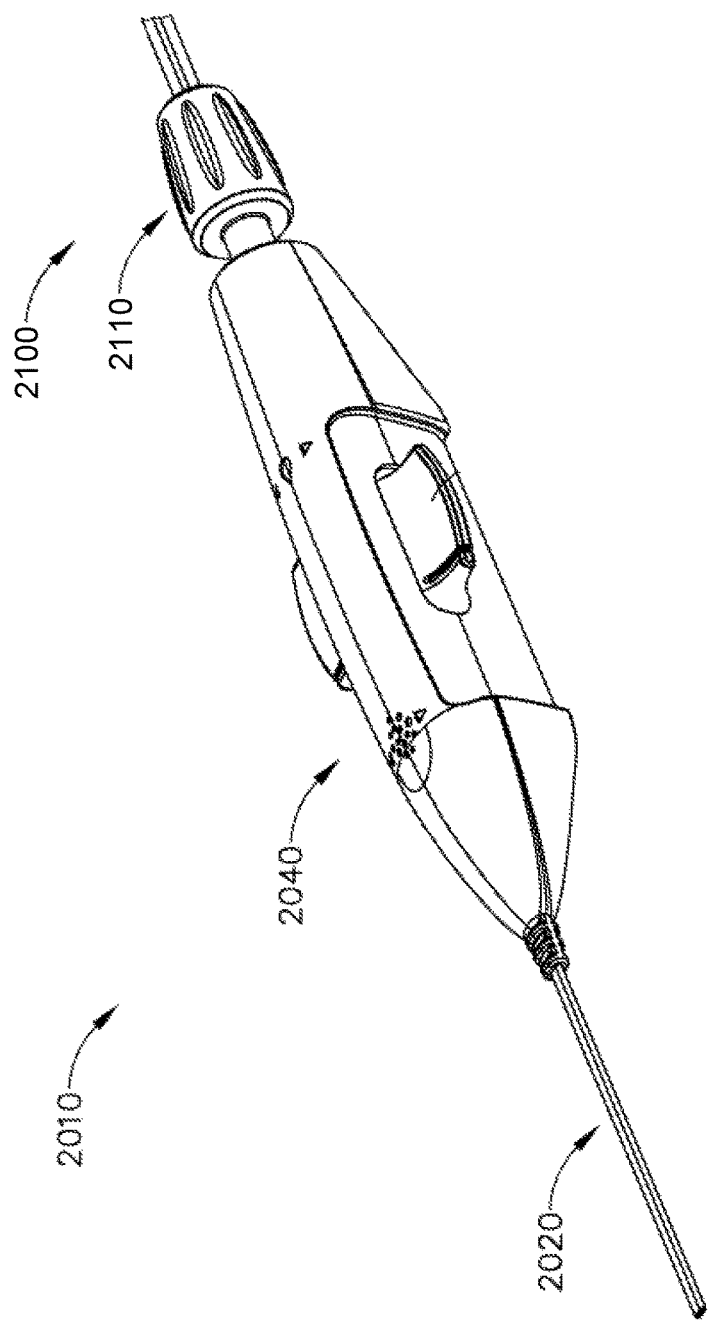
FIG. 7 depicts a perspective view of another exemplary alternative instrument for subretinal administration of a therapeutic agent from a suprachoroidal approach.

FIG. 7 shows an exemplary alternative instrument (2010) that is similar to instrument (10) described above. While certain features and operabilities of instrument (2010) are described below, it should be understood that, in addition to or in lieu of the following, instrument (2010) may be configured and/or operable in accordance with any of the teachings of U.S. patent application Ser. No. 14/619,256, entitled "Method and Apparatus for Suprachoroidal Administration of Therapeutic Agent," filed Feb. 11, 2015, the disclosure of which is incorporated by reference herein. Like with instrument (10), instrument (2010) of the present example is generally usable in the procedure described herein to deliver a therapeutic fluid subretinally to an eye of a patient from a suprachoroidal approach. It should therefore be understood that instrument (2010) may be readily used in place of instrument (10) to perform the medical procedures described herein. Like instrument (10), instrument (2010) of this example comprises a cannula (2020), a body (2040), and an actuation assembly (2100). Cannula (2020) includes a nitinol needle (2030) (shown in FIGS. 20-21, 23B, 26B-26C, and 27B) extending therethrough and is substantially the same as cannula (20) described above. In the present example, cannula (2020) and needle (2030) are substantially identical to cannula (20) and needle (30) described above.

The primary difference between instrument (10) and instrument (2010) is that actuation assembly (2100) of instrument (2010) is rotatable instead of being slidable. Additionally, instrument (2010) includes a valve assembly (not shown) that is operable to change the fluid state of needle (2030). Actuation assembly (2100) is generally operable to translate the valve assembly longitudinally to thereby translate needle (2030) longitudinally relative to cannula (2020) through rotation of a knob member (2110).

When actuation assembly (2100) is in the proximal position, an operator may rotate knob member (2110) in either a counter clockwise or clockwise direction. If knob member (2110) is rotated in the counter clockwise direction, rotation member (2110) will merely rotate freely. To begin advancement of actuation assembly (2100), the valve assembly, and needle (2030), an operator may rotate knob member (2110) in the clockwise direction. Clockwise rotation of knob member (2110) will act to translate knob member (2110) distally and will also act to translate the valve assembly and needle (2030) distally. An operator may continue clockwise rotation of knob member (2110) to drive needle (2030) out of the distal end of cannula (2020), such that a distal end (2032) of needle (2030) is distal to the distal end of cannula (2020). Once needle (2030) has been advanced to its furthest distal position relative to the distal end of cannula (2020), further clockwise rotation of knob member (2110) will merely result in free rotation of knob member (2110) due to slipping of clutch features that are integrated into actuation assembly (2100). With needle (2030) in the distal position, the operator may actuate valve assembly to enable the delivery of therapeutic agent via a lumen (2034) of needle (2030) as described in greater detail below.

After the therapeutic agent is delivered, the operator may then wish to retract needle (2030). Counter clockwise rotation of knob member (2110) will cause proximal translation of actuation assembly (2100), the valve assembly, and needle (2030) relative to body (2040). It should be understood that as actuation assembly (2100) is rotated to actuate the valve assembly, and needle (2030), the valve assembly and needle (2030) remain substantially rotationally stationary relative to body (2040). It should also be understood that although rotation member (2110) of the present example is described as being manually rotated, rotation member (2110) may be rotated via a motor and/or some other motive source. Thus, it should be understood that translation of needle (2030) may be mechanically/electrically driven via a servomotor. The actuation of a servomotor may be controlled by a servo controller as will be described in more detail below. Such a servo control may be manually operated. Additionally or alternatively, such a servo controller may be operated via a computer acting on feedback from instrument (2010) or any other component described herein.

III. Exemplary Suture Measurement Template

FIG. 8 shows an exemplary suture measurement template (210) that may be used in a procedure providing subretinal delivery of a therapeutic agent from a suprachoroidal approach, as will be described in greater detail below. Generally, template (210) is configured to be pressed against an eye of a patient to stamp a particular pattern of pigment onto the patient's eye. It should be understood that reference herein to pressing template (210) against an eye of a patent may include, but is not necessarily limited to, pressing template (210) directly against the sclera (304) surface (e.g., after the conjunctiva has been taken down or otherwise displaced). Template (210) comprises a rigid body (220) and a rigid shaft (240). As will be described in greater detail below, body (220) is generally contoured to correspond to the curvature of a patient's eye such that body (220) may be pressed or placed onto at least a portion of the patient's eye. Body (220) comprises an upper guide portion (222) and a plurality of protrusions (230) extending distally from an eye face (224) of body (220).

Upper guide portion (222) is generally semi-circular in shape and is disposed at the top of body (220). The semi-circular shape of upper guide portion (222) has a radius that corresponds to the curvature of the limbus of a patient's eye. In other words, upper guide portion (222) curves proximally along a first radius corresponding to a radius of curvature of a patient's eyeball; and downwardly (toward the longitudinal axis of shaft (240)) along a second radius corresponding to a radius of curvature of the limbus of the patient's eye. As will be described in greater detail below, upper guide portion (222) may be used to properly locate template (210) relative to the limbus of the patient's eye. Accordingly, any pigmentation that may be deposited onto a patient's eye by template may be positioned relative to the limbus of the patient's eye.

Protrusions (230) are spaced a predetermined distance from upper guide portion (222). In particular, protrusions (230) form a pattern that may correspond to relevant marks for use during the method described below. Protrusions (230) of the present example comprise four suture loop protrusions (230a-230h) and two sclerotomy protrusions (230i, 230j). Suture loop protrusions (230a-320h) and sclerotomy protrusions (230i, 230j) extend outwardly from body (220) an equal distance such that protrusions (230) collectively maintain the curvature defined by body (220). In other words, the tips of protrusions (230a-230j) all lie along a curved plane that is defined by a radius of curvature complementing the radius of curvature of the patient's eyeball. The tips of protrusions (230a-230j) are rounded and atraumatic such that protrusions (230a-230j) may be pressed against the eye without damaging the sclera or other portions of the patient's eye.

Shaft (240) extends proximally from body (220). Shaft (240) is configured to permit an operator to grasp template (210) and manipulate body (220). In the present example, shaft (240) is integral with body (220). In other examples, shaft (240) may be selectively attachable to body by a mechanical fastening means such as a threaded coupling or a mechanical snap fit, etc. In some versions, an operator may be presented with a kit comprising a shaft (240) and a plurality of bodies (220). The bodies (220) may have different curvatures to correspond with different eyeballs having different radii of curvature. The operator may thus select an appropriate body (220) from the kit based on the anatomy of the particular patient before the operator; and the operator may then secure the selected body (220) to the shaft (240). Although not shown, it should be understood that the proximal end of shaft (240) may additionally include a t-grip, knob, or other gripping feature to permit an operator to more readily grip shaft (240).

In an exemplary use, suture loop protrusions (232) and sclerotomy protrusions (234) each correspond to a particular portion of the method described below. In particular, prior to, or during the method described below, an operator may coat protrusions (230) with a biocompatible pigment or ink by pressing protrusions (230) onto a pigment or ink pad (250), by brushing the pigment or ink onto protrusions (230), or by otherwise applying the pigment or ink to protrusions (230). Once protrusions (230) have received the pigment or ink, an operator may mark an eye of a patent by pressing protrusions (230) of template (210) onto the eye of the patient, as will be described in greater detail below. Once template (210) is removed from an eye of a patient, the pigment from protrusions may remain adhered to the eye to mark particular points of interest, as will be described in greater detail below.

IV. Exemplary Method for Subretinal Delivery of Therapeutic Agent from a Suprachoroidal Approach FIGS. 9A-11C show an exemplary procedure for subretinal delivery of therapeutic agent from a suprachoroidal approach using instrument (10) described above. It should be understood however, that instrument (2010) may be readily used in addition to or in lieu of instrument (10) in the procedure described below. By way of example only, the method described herein may be employed to treat macular degeneration and/or other ocular conditions. Although the procedure described herein is discussed in the context of the treatment of age-related macular degeneration, it should be understood that no such limitation is intended or implied. For instance, in some merely exemplary alternative procedures, the same techniques described herein may be used to treat retinitis pigmentosa, diabetic retinopathy, and/or other ocular conditions. Additionally, it should be understood that the procedure described herein may be used to treat either dry or wet age-related macular degeneration.

Figure 9B:
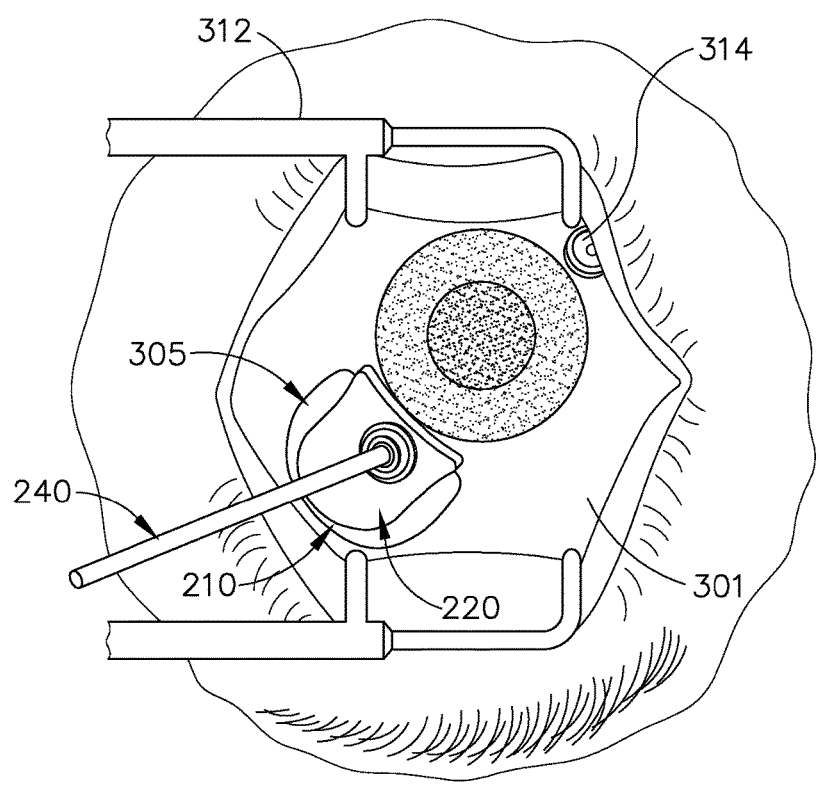
FIG. 9B depicts a top plan view of the eye of FIG. 9A, with the template of FIG. 8 disposed on the eye.
Figure 10A:
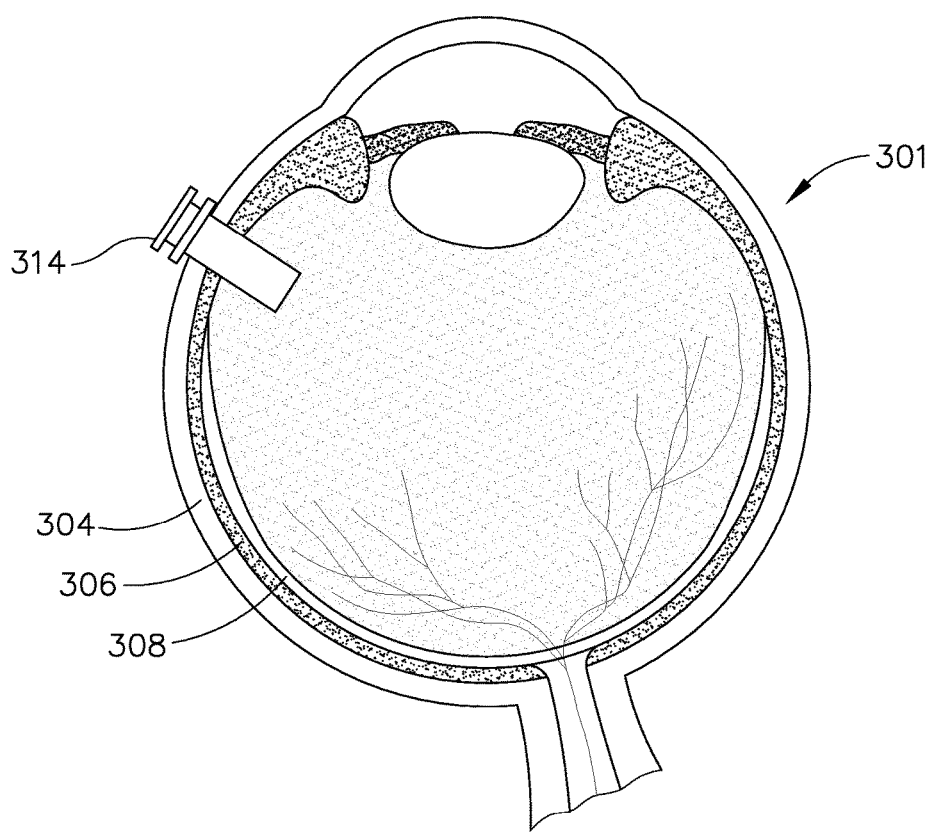
FIG. 10A depicts a cross-sectional view of the eye of FIG. 9A, with the cross-section taken about line 10A-10A of FIG. 9A.
Figure 10B:
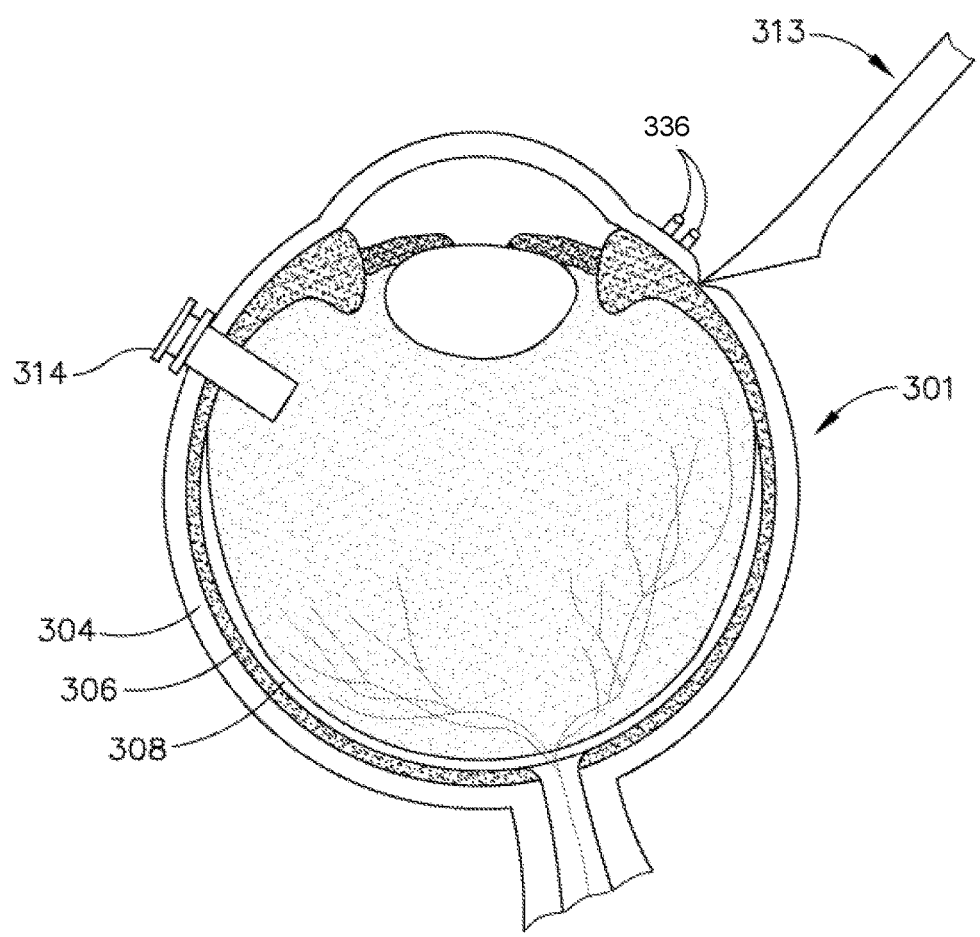
FIG. 10B depicts a cross-sectional view of the eye of FIG. 9A, with the cross-section taken about line 10B-10B of FIG. 9E.

As can be seen in FIG. 9A, the procedure begins by an operator immobilizing tissue surrounding a patient's eye (301) (e.g., the eyelids) using a speculum (312), and/or any other instrument suitable for immobilization. While is immobilization described herein with reference to tissue surrounding eye (301), it should be understood that eye (301) itself may remain free to move. Once the tissue surrounding eye (301) has been immobilized, an eye chandelier port (314) is inserted into eye (301) to provide intraocular illumination when the interior of eye (301) is viewed through the pupil. In the present example, eye chandelier port (314) is positioned in the inferior medial quadrant such that a superior temporal quadrant sclerotomy may be preformed. As can be seen in FIG. 10A, eye chandelier port (314) is positioned to direct light onto the interior of eye (301) to illuminate at least a portion of the retina (e.g., including at least a portion of the macula). As will be understood, such illumination corresponds to an area of eye (301) that is being targeted for delivery of therapeutic agent. In the present example, only chandelier port (314) is inserted at this stage, without yet inserting an optical fiber (315) into port (314). In some other versions, an optical fiber (315) may be inserted into chandelier port (314) at this stage. In either case, a microscope may optionally be utilized to visually inspect the eye (301) to confirm proper positioning of eye chandelier port (314) relative to the target site. Although FIG. 9A shows a particular positioning of eye chandelier port (314), it should be understood that eye chandelier port (314) may have any other positioning as will be apparent to those of ordinary skill in the art in view of the teachings herein.

Figure 9C:
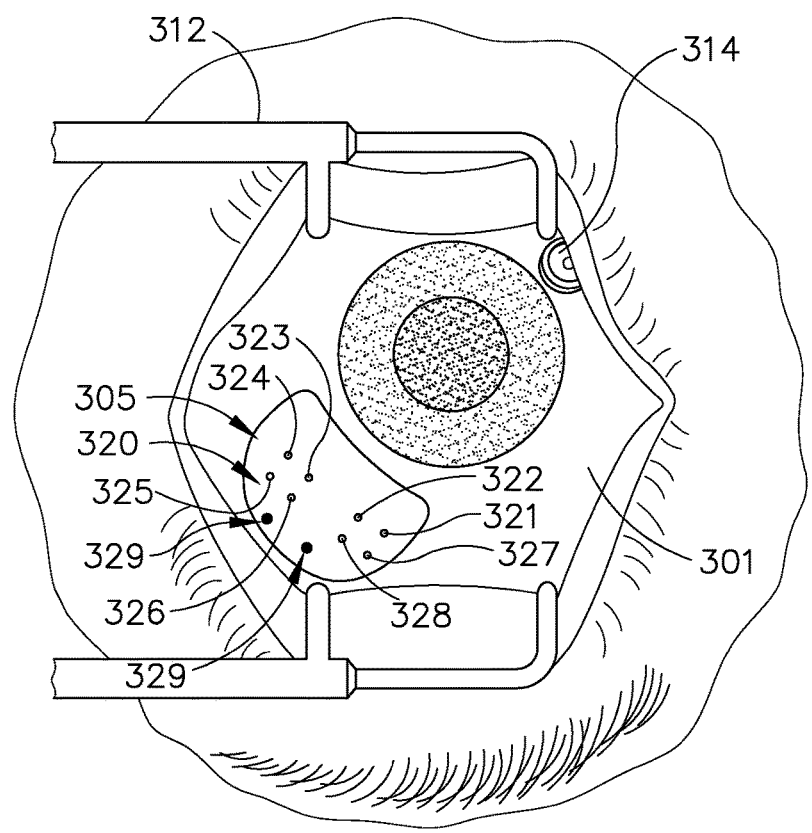
FIG. 9C depicts a top plan view of the eye of FIG. 9A, with a plurality of markers disposed on the eye.

Once eye chandelier port (314) has been positioned, the sclera (304) may be accessed by dissecting the conjunctiva by incising a flap in the conjunctiva and pulling the flap posteriorly. After such a dissection is completed, the exposed surface (305) of the sclera (304) may optionally be blanched using a cautery tool to minimize bleeding. Once conjunctiva dissection is complete, the exposed surface (305) of the sclera (304) may optionally be dried using a WECK-CEL or other suitable absorbent device. Template (210), described above, may then be used to mark eye (301). As can be seen in FIG. 9B, template (210) is positioned to align with the limbus of eye (301). An operator may apply a light force to template (210) to apply pigment to eye (301). Template (210) is then removed, leaving pigment adhered to the exposed surface (305) of the sclera (304) to provide a visual guide (320) for an operator, as can be seen in FIG. 9C. An operator may then use visual guide (320) to attach a suture loop assembly (330) and to perform a sclerotomy. Visual guide (320) comprises a set of suture loop markers (321, 322, 323, 324, 325, 326, 327) and a pair of sclerotomy markers (329).

Figure 9D:
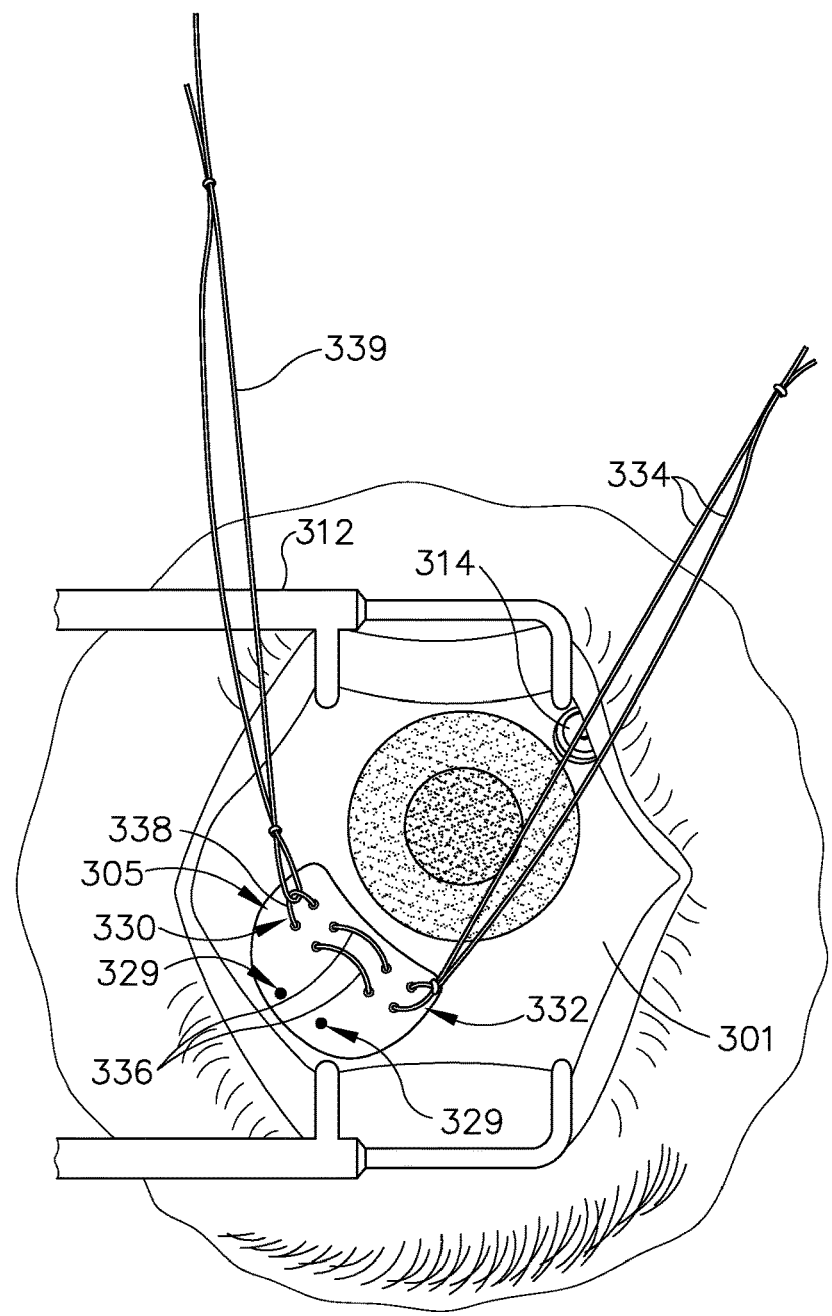
FIG. 9D depicts a top plan view of the eye of FIG. 9A, with a suture loop attached to the eye.
Figure 9E:
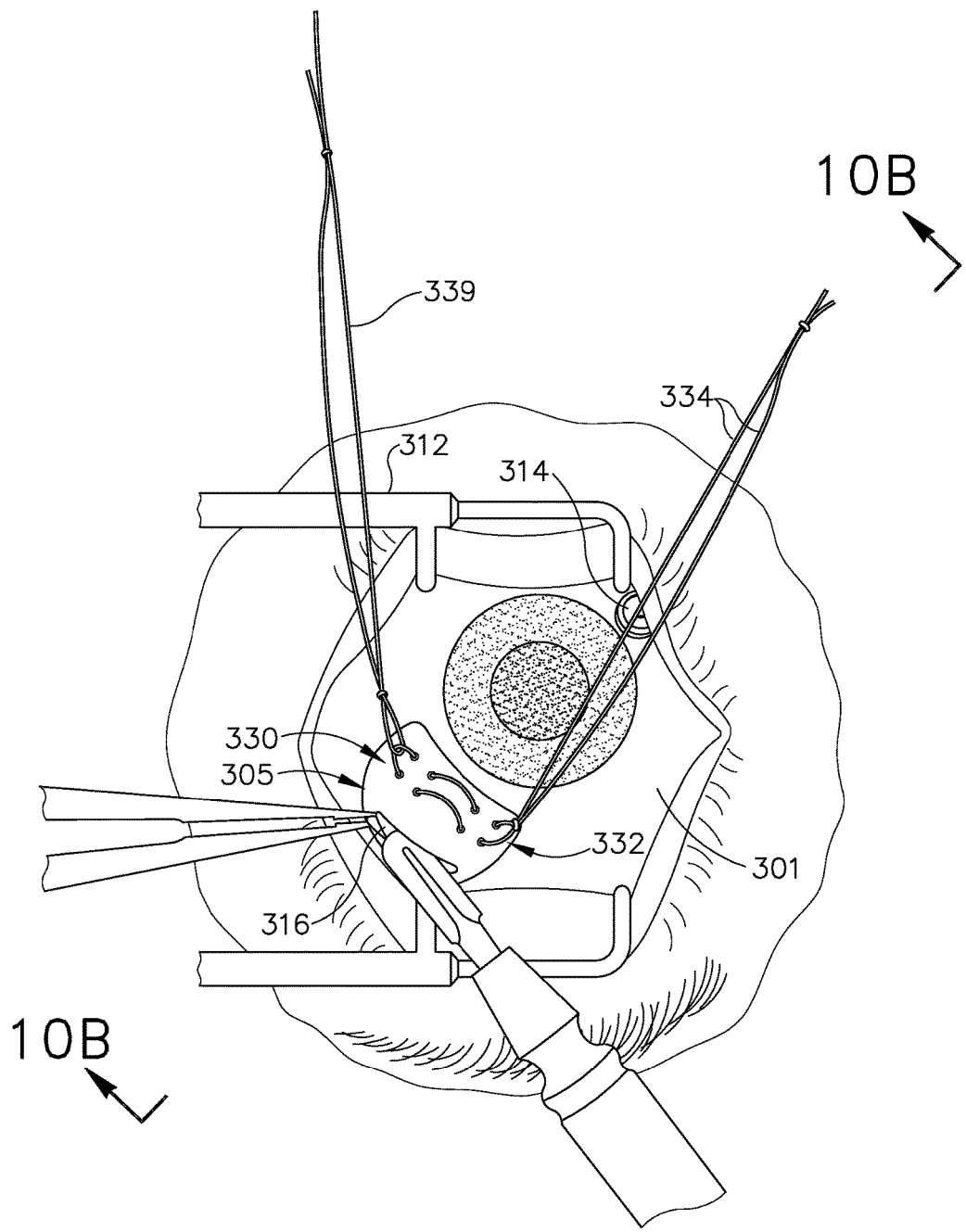
FIG. 9E depicts a top plan view of the eye of FIG. 9A, with a sclerotomy being performed.

FIG. 9D shows a completed suture loop assembly (330). As will be described in greater detail below, suture loop assembly (330) is generally configured to guide cannula (20) of instrument (10) through a sclerotomy and into eye (301). An exemplary procedure that may be employed to create the suture loop assembly (330) that is shown in FIG. 9D is described in U.S. patent application Ser. No. 14/619,256, entitled "Method and Apparatus for Suprachoroidal Administration of Therapeutic Agent," filed Feb. 11, 2015, the disclosure of which is incorporated by reference herein. Once suture loop assembly (330) has been attached to eye (301), a sclerotomy may be performed on eye (301). As seen in FIG. 9E, eye (301) is cut between sclerotomy markers (329) using a conventional scalpel (313) or other suitable cutting instrument. Although sclerotomy markers (329) are shown as comprising two discrete dots, it should be understood that in other examples, markers (329) may comprise any other type of markings such as a solid, dotted or dashed line. The sclerotomy procedure forms a small incision (316) through sclera (304) of eye (301). As can best be seen in FIG. 10B, the sclerotomy is preformed with particular care to avoid penetration of the choroid (306). Thus, the sclerotomy procedure provides access to the space between sclera (304) and choroid (306). Once incision (316) is made in eye (301), a blunt dissection may optionally be performed to locally separate sclera (304) from choroid (306). Such a dissection may be performed using a small blunt elongate instrument, as will be apparent to those of ordinary skill in the art in view of the teachings herein.

Figure 9F:
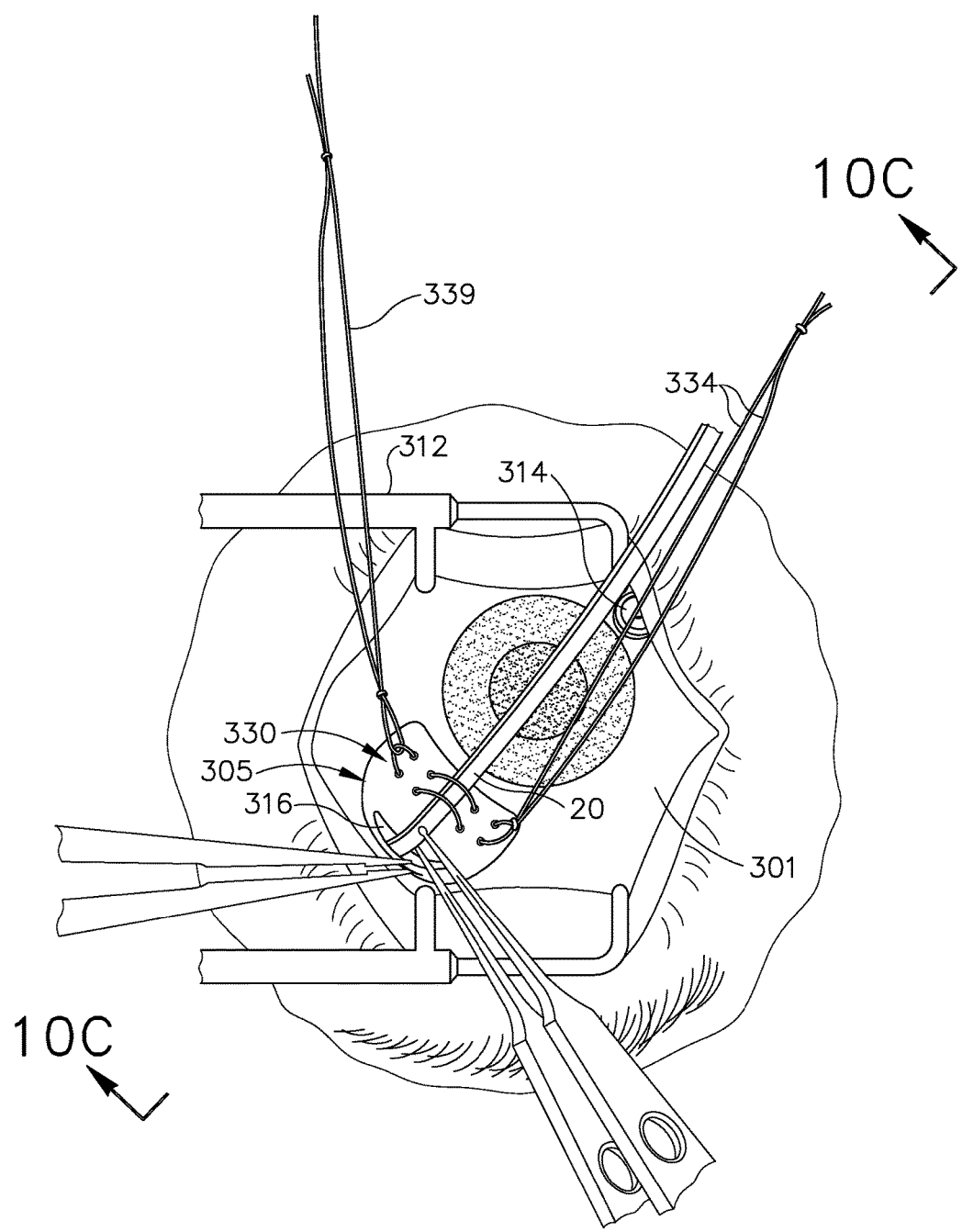
FIG. 9F depicts a top plan view of the eye of FIG. 9A, with the instrument of FIG. 1 being inserted through the sclerotomy opening and in between the sclera and choroid of the eye.

With the sclerotomy procedure performed, an operator may insert cannula (20) of instrument (10) through incision (316) and into the space between sclera (304) and choroid (306). As can be seen in FIG. 9F, cannula (20) is directed through guide loops (336) of suture loop assembly (330) and into incision (316). As described above, guide loops (336) may stabilize cannula (20). Additionally, guide loops (336) maintain cannula (20) in a generally tangential orientation relative to incision (316). Such tangential orientation may reduce trauma as cannula (20) is guided through incision (316) to stabilize cannula (20) and to prevent damage to surrounding tissue. As cannula (20) is inserted into incision (316) through guide loops (336), an operator may use forceps or other instruments to further guide cannula (20) along an atraumatic path. Of course, use of forceps or other instruments is merely optional, and may be omitted in some examples. Although not shown, it should be understood that in some examples cannula (20) may include one or more markers on the surface of cannula (20) to indicate various depths of insertion. While merely optional, such markers may be desirable to aid an operator in identifying the proper depth of insertion as cannula (20) is guided along an atraumatic path. For instance, the operator may visually observe the position of such markers in relation to guide loops (336) and/or in relation to incision (316) as an indication of the depth to which cannula (20) is inserted in eye (301). By way of example only, one such marker may correspond to an approximately 6 mm depth of insertion of cannula (20).

Once cannula (20) is at least partially inserted into eye (301), an operator may insert an optical fiber (315) into eye chandelier port (314) if the fiber (315) had not yet been inserted at this stage. With eye chandelier port (314) in place and assembled with optical fiber (315), an operator may activate eye chandelier port (314) by directing light through optical fiber (315) to provide illumination of eye (301) and thereby visualize the interior of eye (301). Further adjustments to the positioning of cannula (20) may optionally be made at this point to ensure proper positioning relative to the area of geographic atrophy of retina (308). In some instances, the operator may wish to rotate the eye (301), such as by pulling on sutures (334, 339), to direct the pupil of the eye (301) toward the operator in order to optimize visualization of the interior of the eye (301) via the pupil.

Figure 9G:
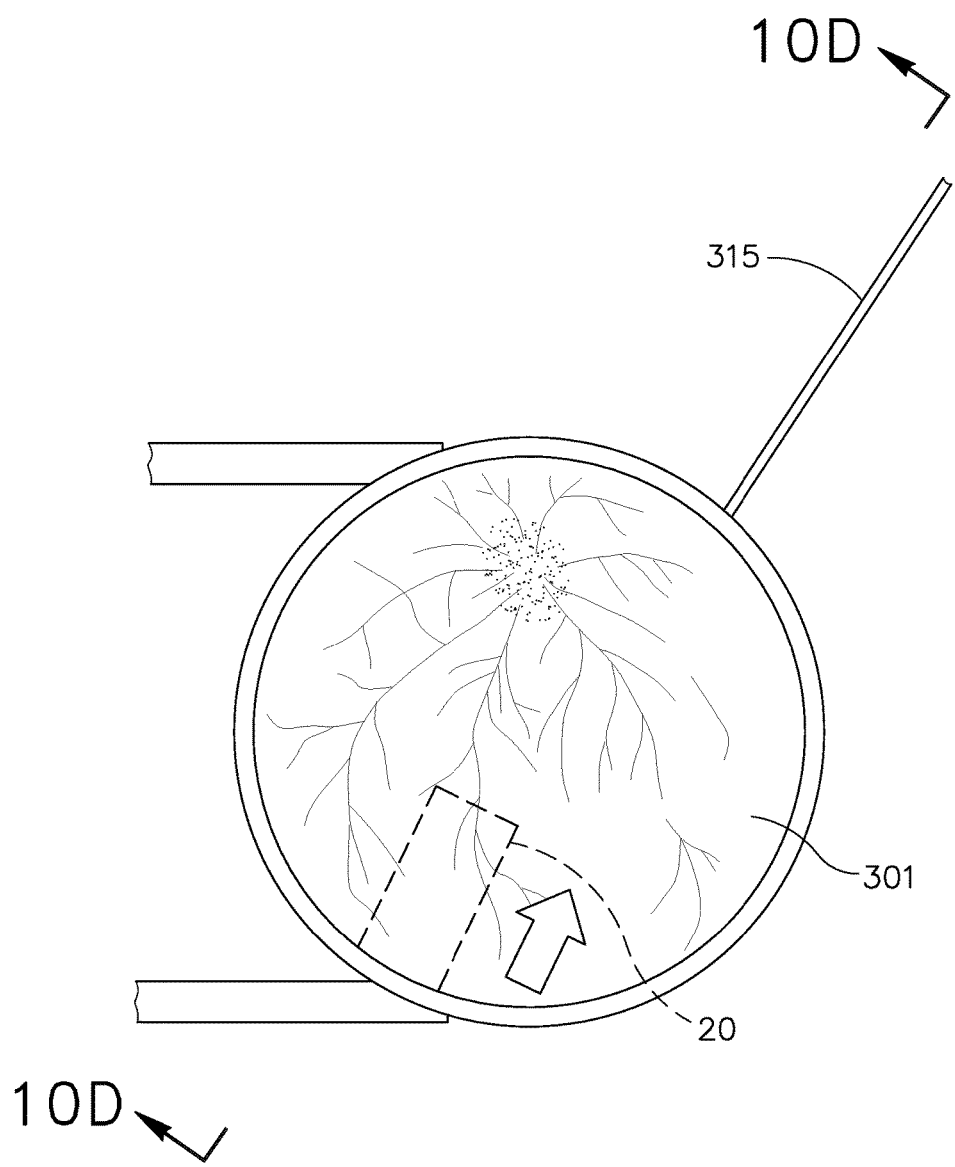
FIG. 9G depicts a top plan view of the eye of FIG. 9A, with the instrument of FIG. 1 under direct visualization at the back of the eye, between the sclera and choroid.
Figure 10C:
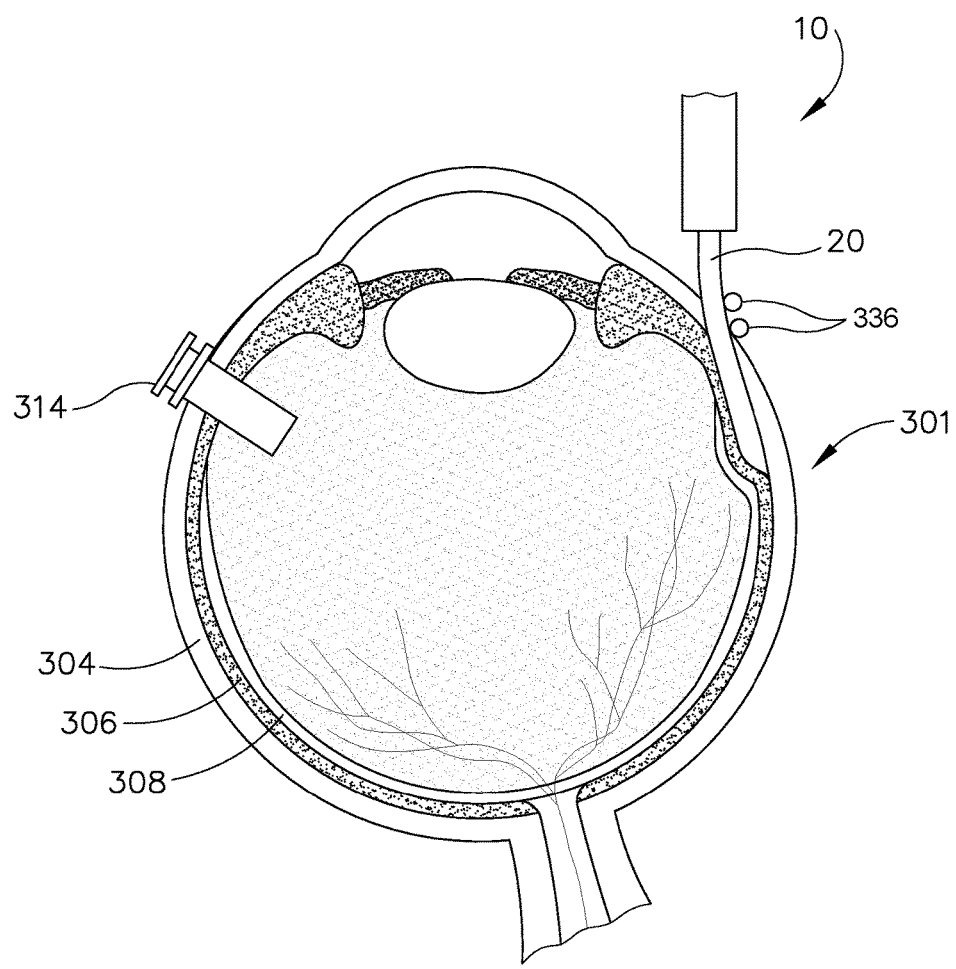
FIG. 10C depicts a cross-sectional view of the eye of FIG. 9A, with the cross-section taken about line 10C-10C of FIG. 9F.
Figure 10D:
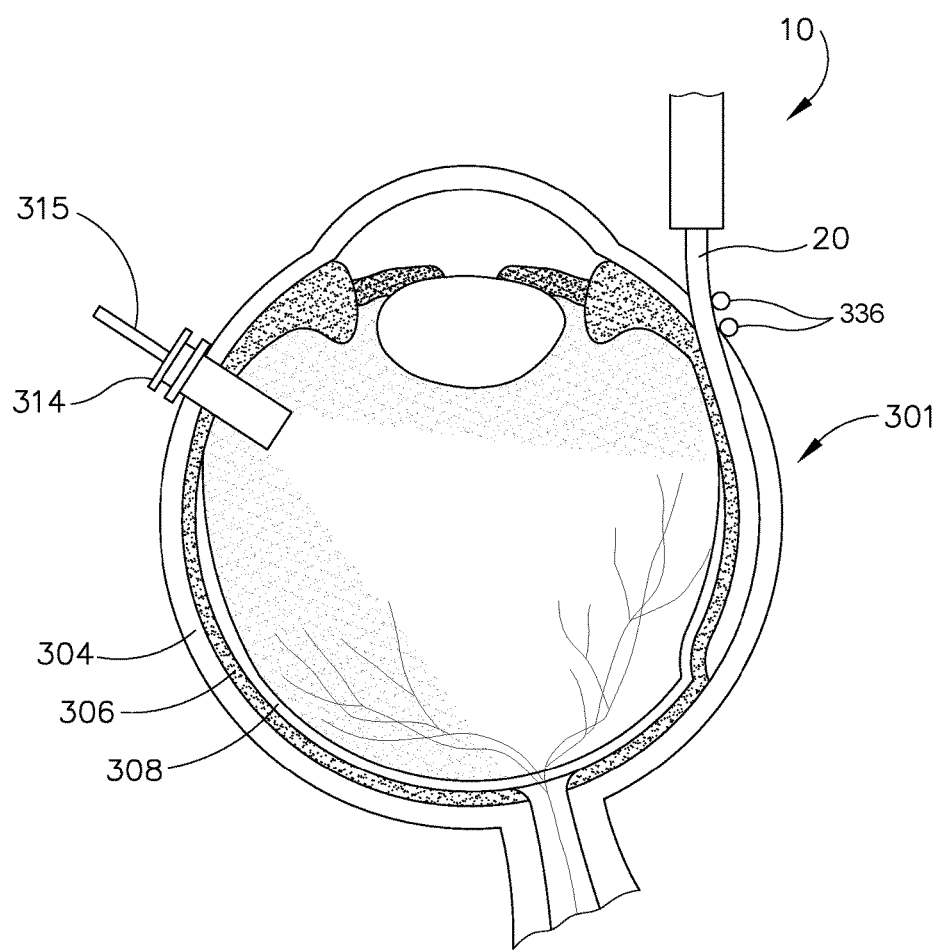
FIG. 10D depicts a cross-sectional view of the eye of FIG. 9A, with the cross-section taken about line 10D-10D of FIG. 9G.
Figure 10E:
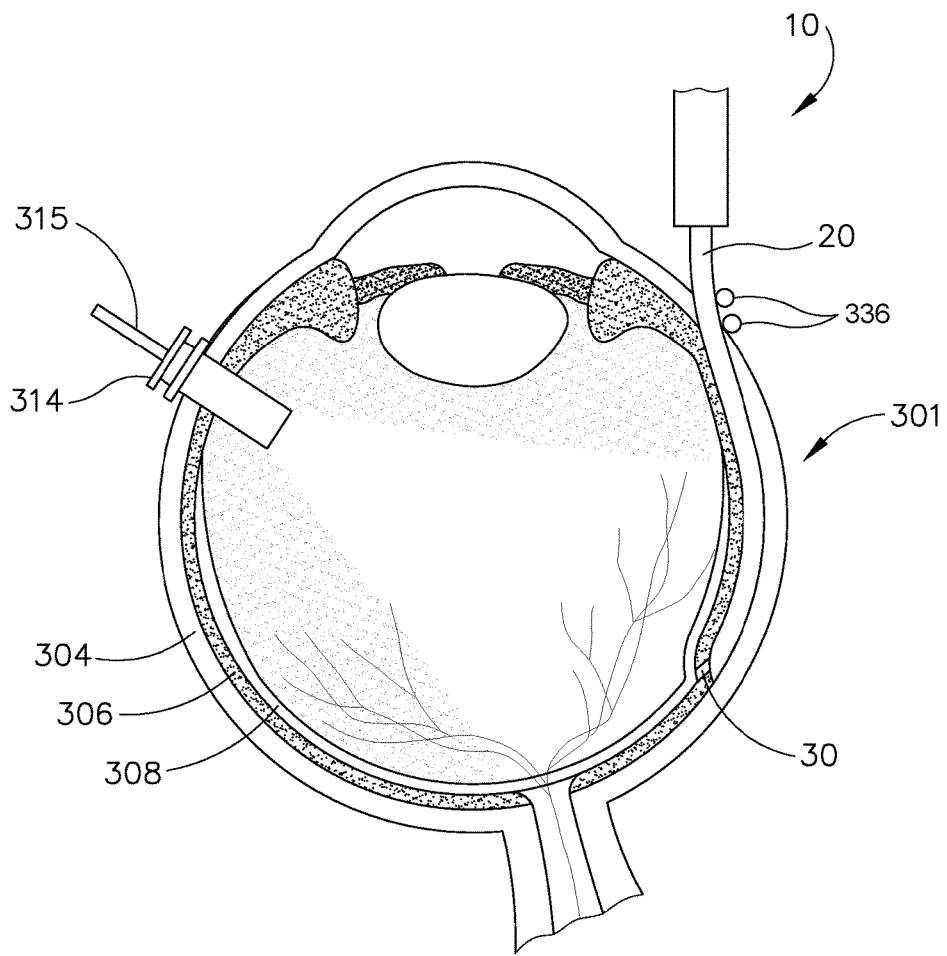
FIG. 10E depicts a cross-sectional view of the eye of FIG. 9A, with the cross-section taken about line 10E-10E of FIG. 9H.

FIGS. 9G and 10C-10D show cannula (20) as it is guided between sclera (304) and choroid (306) to the delivery site for the therapeutic agent. In the present example, the delivery site corresponds to a generally posterior region of eye (301) adjacent to an area of geographic atrophy of retina (308). In particular, the delivery site of the present example is superior to the macula, in the potential space between the neurosensory retina and the retinal pigment epithelium layer. FIG. 9G shows eye (301) under direct visualization through a microscope directed through the pupil of eye (301), with illumination provided through fiber (315) and port (314). As can be seen, cannula (20) is at least partially visible through a retina (308) and choroid (306) of eye (301). Thus, an operator may track cannula (20) as it is advanced through eye (301) from the position shown in FIG. 10C to the position shown in 10D. Such tracking may be enhanced in versions where an optical fiber (315) is used to emit visible light through the distal end of cannula (20).

Figure 9H:
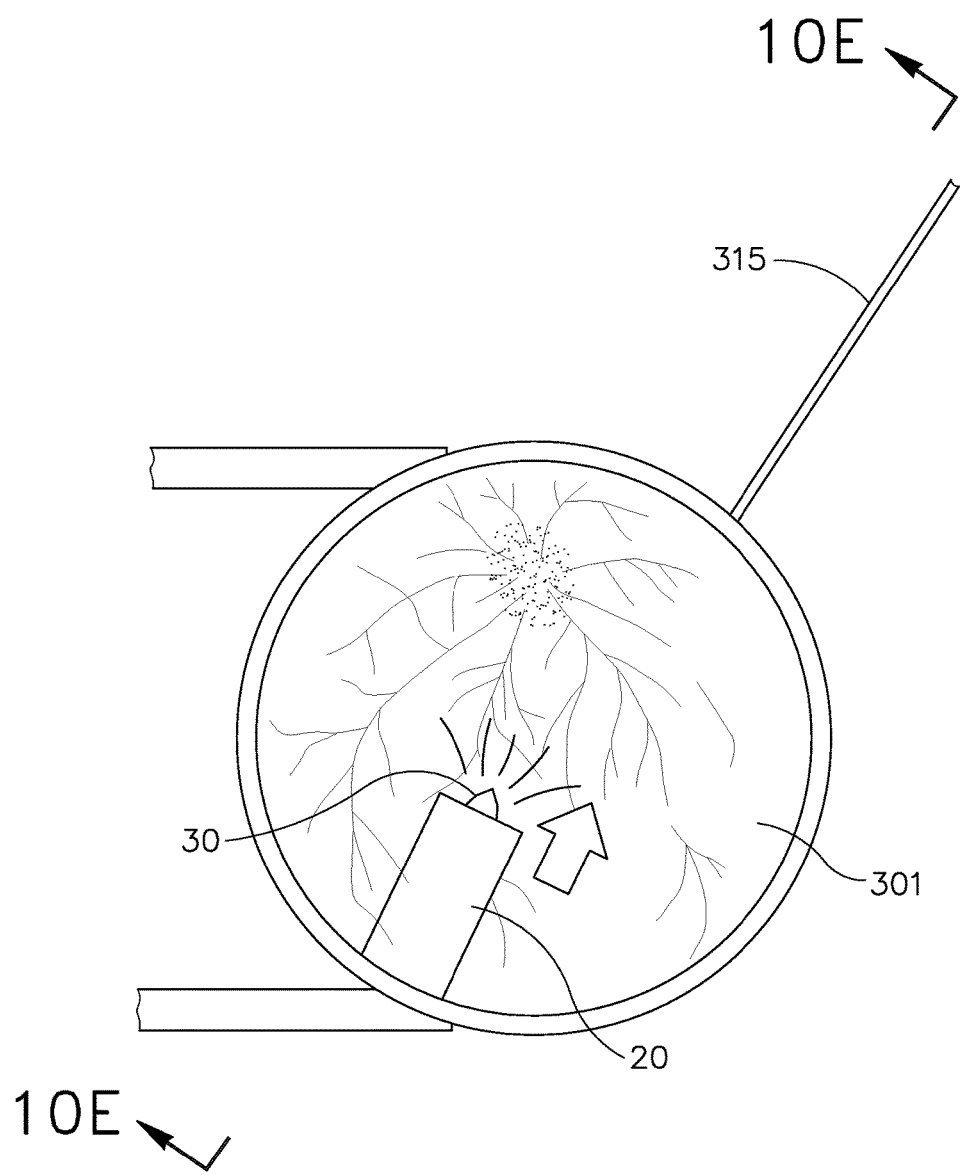
FIG. 9H depicts a top plan view of the eye of FIG. 9A, with the needle of the instrument of FIG. 1 being advanced under direct visualization at the back of the eye, pressing against the outer surface of the choroid causing the choroid to 'tent'.

Once cannula (20) has been advanced to the delivery site as shown in FIG. 10D, an operator may advance needle (30) of instrument (10) as described above with respect to FIGS. 3-4. As can be seen in FIGS. 9H-9I, 10E, and 11A, needle (30) is advanced relative to cannula (20) such that needle (30) pierces through choroid (306) without penetrating retina (308). Immediately prior to penetrating choroid (306), needle (30) may appear under direct visualization as "tenting" the surface of choroid (306), as can be seen in FIG. 9H. In other words, needle (30) may deform choroid (306) by pushing upwardly on choroid, providing an appearance similar to a tent pole deforming the roof of a tent. Such a visual phenomenon may be used by an operator to identify whether choroid (306) is about to be pierced and the location of any eventual piercing. The particular amount of needle (30) advancement sufficient to initiate "tenting" and subsequent piercing of choroid (306) may be of any suitable amount as may be determined by a number of factors such as, but not limited to, general patient anatomy, local patient anatomy, operator preference, and/or other factors. As described above, a merely exemplary range of needle (30) advancement may be between approximately 0.25 mm and approximately 10 mm; or more particularly between approximately 2 mm and approximately 6 mm.

Figure 9I:
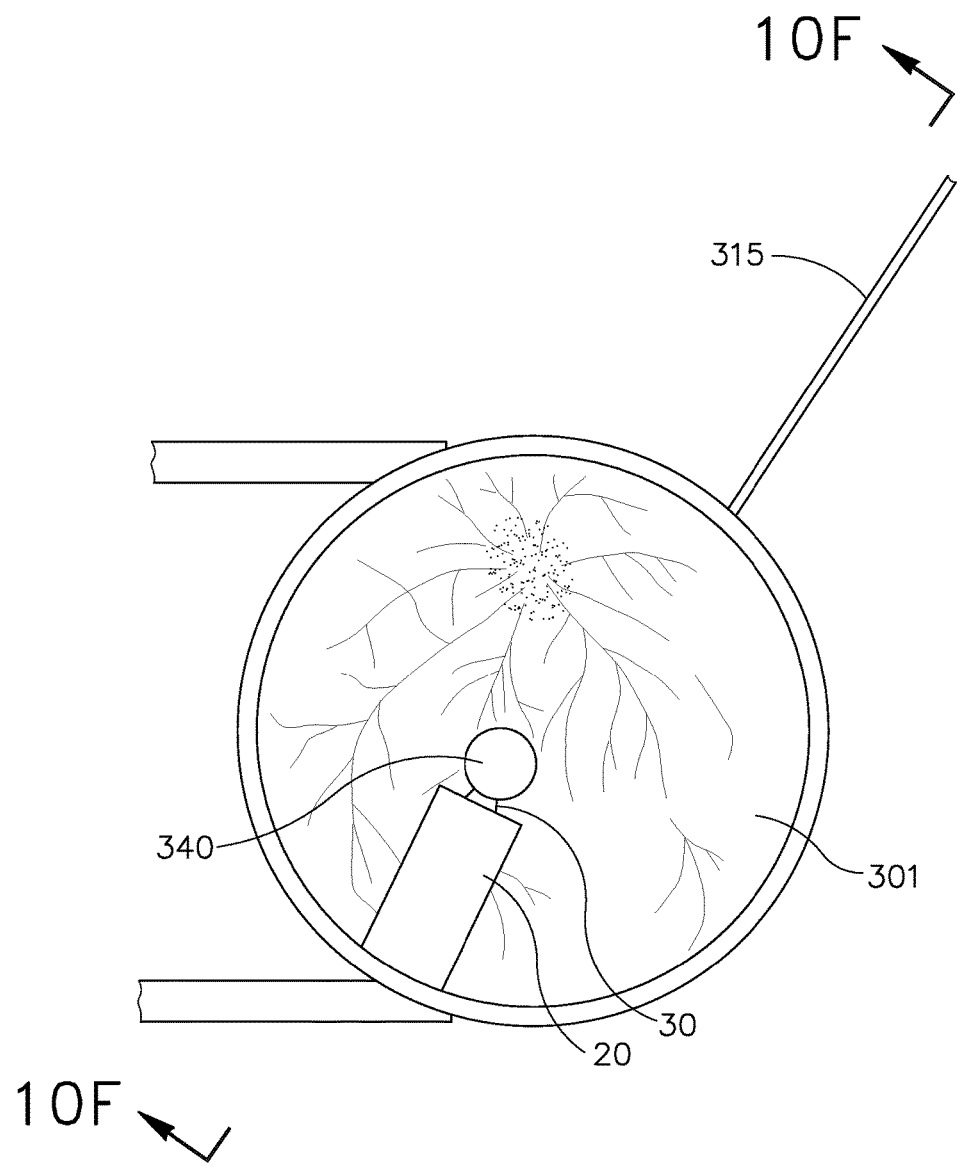
FIG. 9I depicts a top plan view of the eye of FIG. 9A, with the needle dispensing a leading bleb under direct visualization at the back of the eye, the needle between the sclera and choroid, and the leading bleb in the sub retinal space between the choroid and a retina.
Figure 10F:
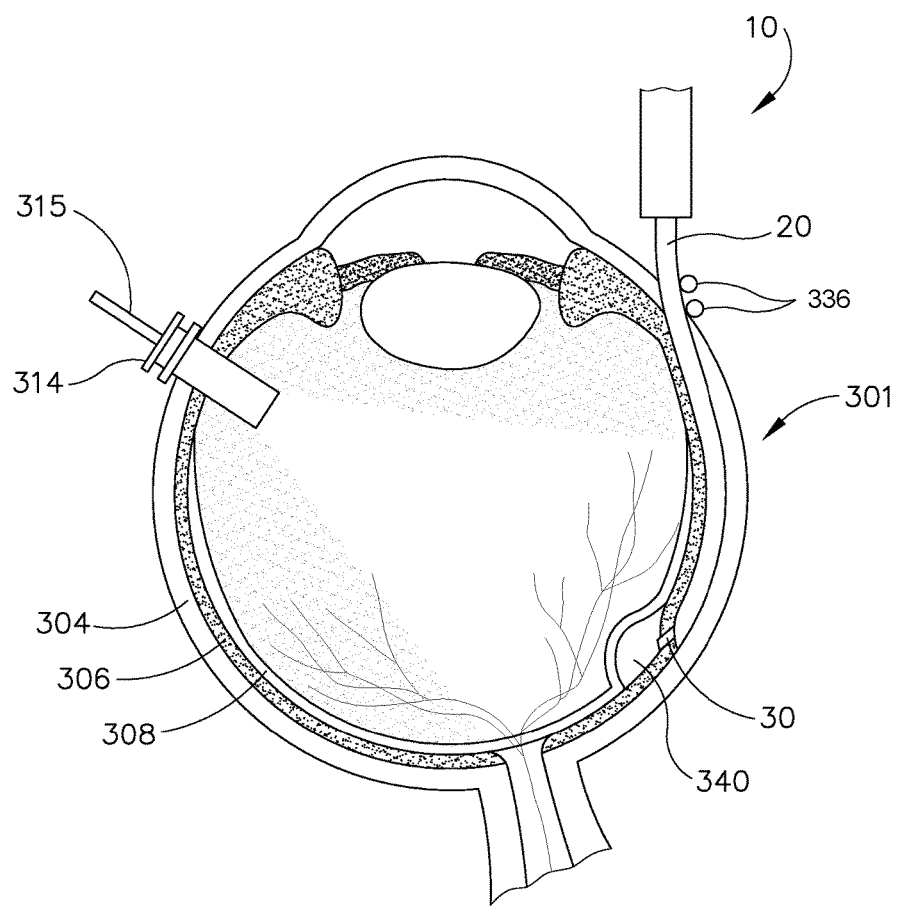
FIG. 10F depicts a cross-sectional view of the eye of FIG. 9A, with the cross-section taken about line 10E-10F of FIG. 9I.
Figure 11A:
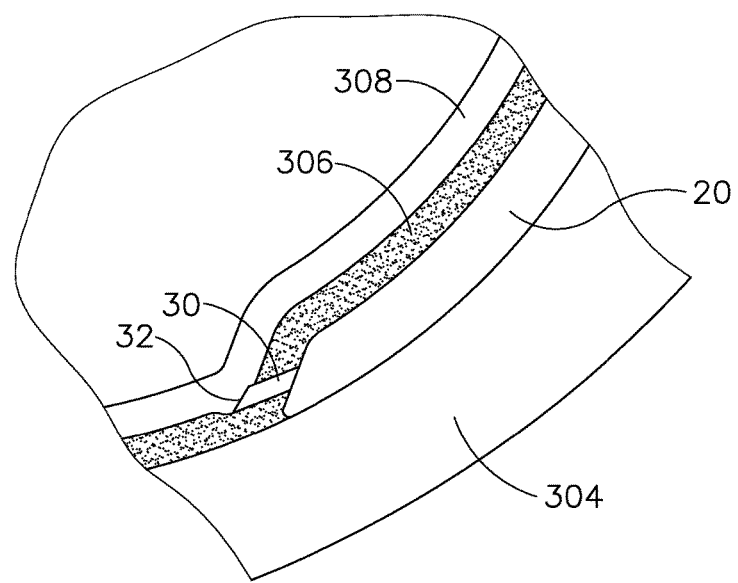
FIG. 11A depicts a detailed cross-sectional view of the eye of FIG. 9A depicted in the state shown in FIG. 10E.
Figure 11B:
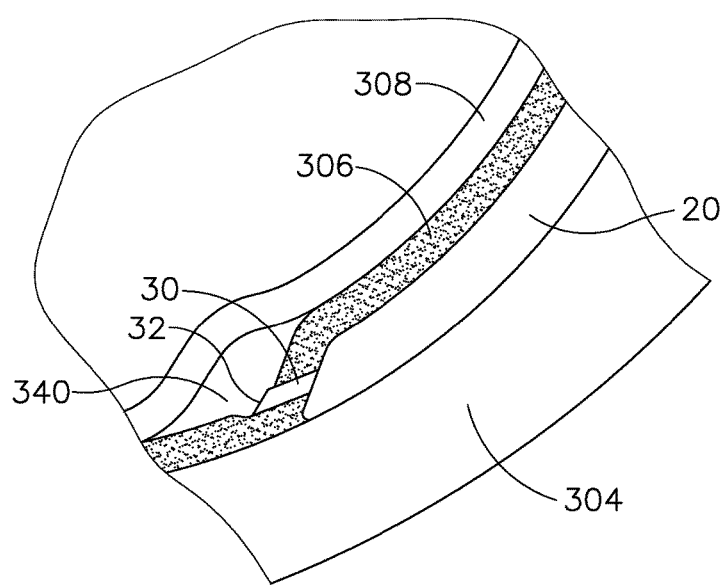
FIG. 11B depicts a detailed cross-sectional view of the eye of FIG. 9A depicted in the state shown in FIG. 10F.

In the present example, after the operator has confirmed that needle (30) has been properly advanced by visualizing the tenting effect described above, the operator infuses a balanced salt solution (BSS) or other similar solution as needle (30) is advanced relative to cannula (20). Such a BSS may form a leading bleb (340) ahead of needle (30) as needle (30) is advanced through choroid (306). Leading bleb (340) may be desirable for two reasons. First, as shown in FIGS. 9I, 10F, and 11B, leading bleb (340) may provide a further visual indicator to an operator to indicate when needle (30) is properly positioned at the delivery site. Second, leading bleb (340) may provide a barrier between needle (30) and retina (308) once needle (30) has penetrated choroid (306). Such a barrier may push the retinal wall outwardly (as is best seen in FIGS. 10F and 11B), thereby minimizing the risk of retinal perforation as needle (30) is advanced to the delivery site. In some versions, a foot pedal is actuated in order to drive leading bleb (340) out from needle (30). Alternatively, other suitable features that may be used to drive leading bleb (340) out from needle (30) will be apparent to those of ordinary skill in the art in view of the teachings herein.

Once the operator visualizes leading bleb (340), the operator may cease infusion of BSS, leaving a pocket of fluid as can be seen in FIGS. 9I, 10F, and 11B. Next, a therapeutic agent (341) may be infused by actuating a syringe or other fluid delivery device as described above with respect to instrument (10). The particular therapeutic agent (341) delivered may be any suitable therapeutic agent configured to treat an ocular condition. Some merely exemplary suitable therapeutic agents may include, but are not necessarily limited to, drugs having smaller or large molecules, therapeutic cell solutions, certain gene therapy solutions, and/or any other suitable therapeutic agent as will be apparent to those of ordinary skill in the art in view of the teachings herein. By way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein.

Figure 9J:
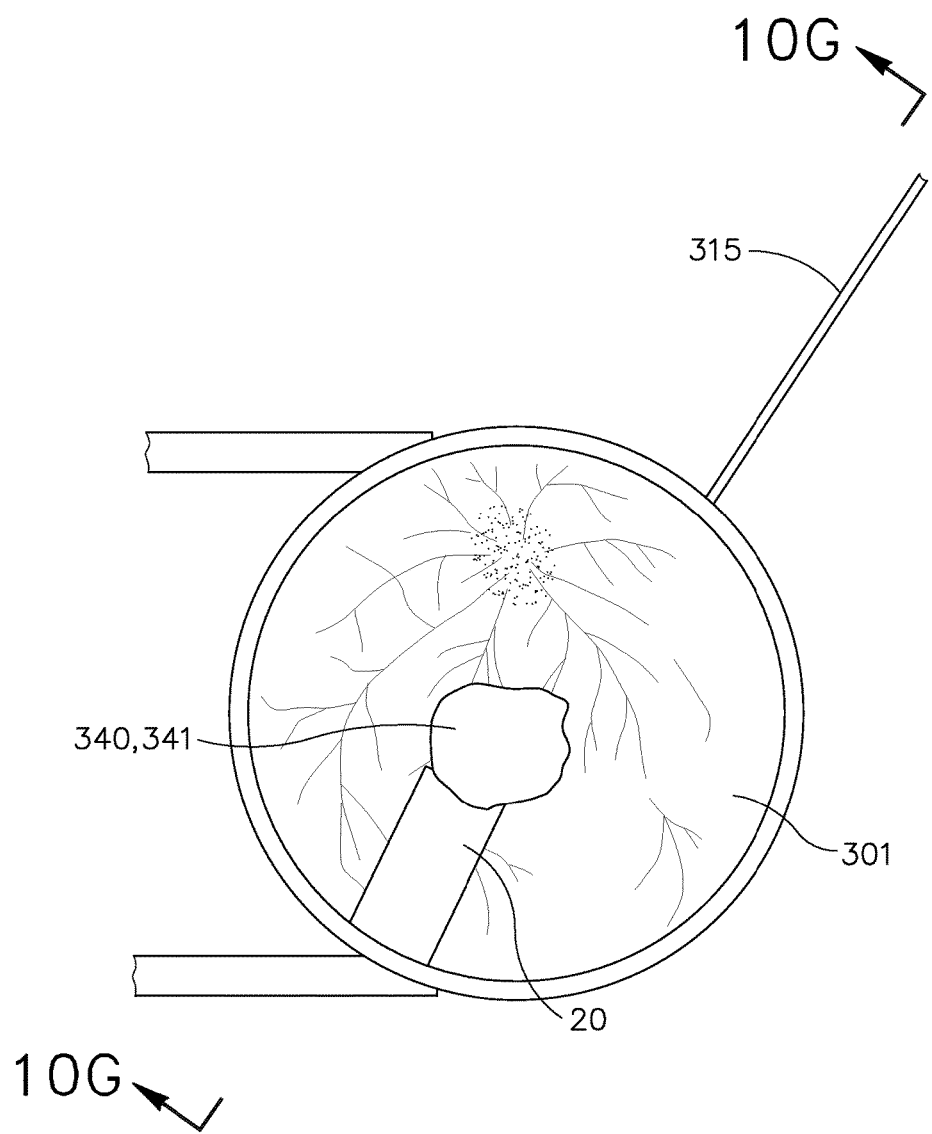
FIG. 9J depicts a top plan view of the eye of FIG. 9A, with the needle dispensing a therapeutic agent to the eye at the back of the eye, between the sclera and choroid.
Figure 10G:
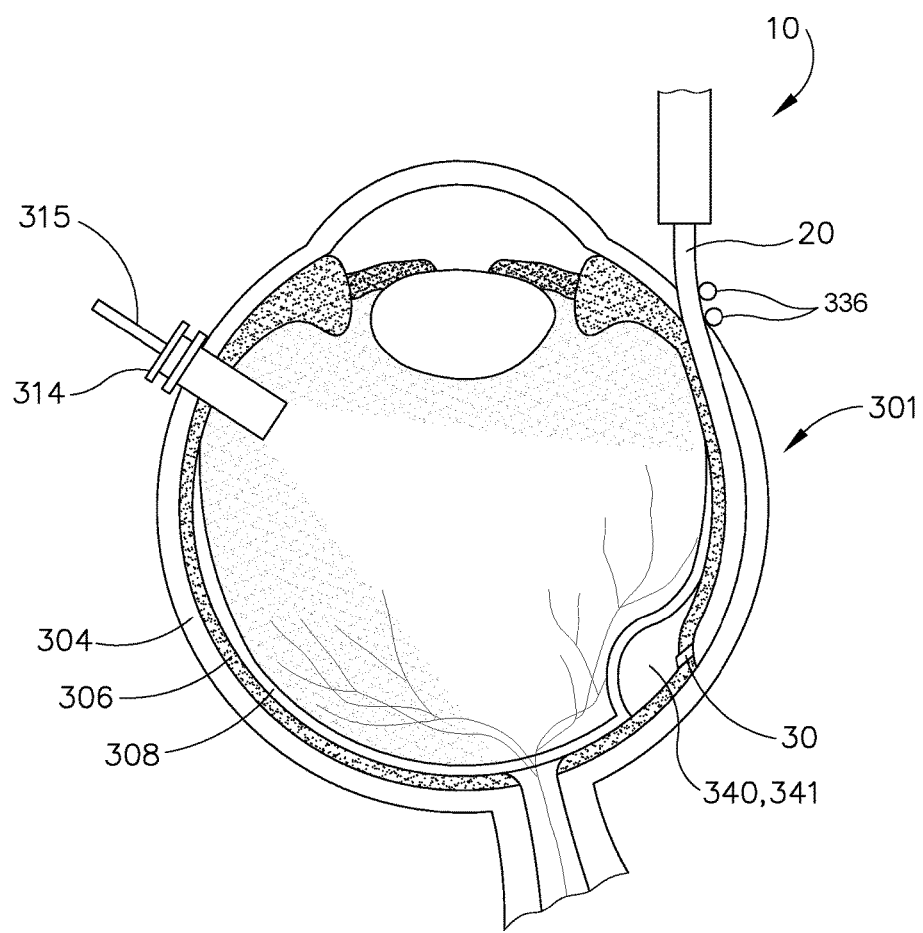
FIG. 10G depicts a cross-sectional view of the eye of FIG. 9A, with the cross-section taken about line 10G-10G of FIG. 9J.
Figure 11C:
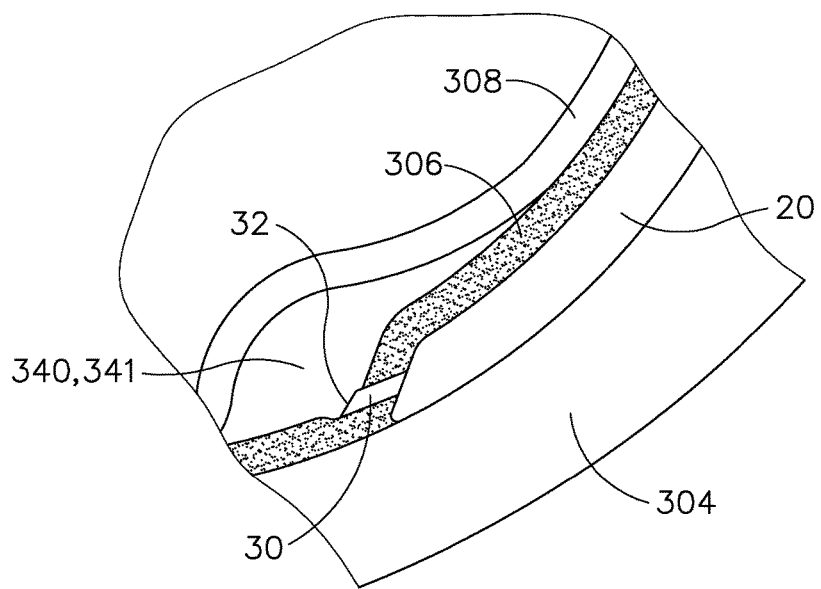
FIG. 11C depicts a detailed cross-sectional view of the eye of FIG. 9A depicted in the state shown in FIG. 10G.
Figure 12:
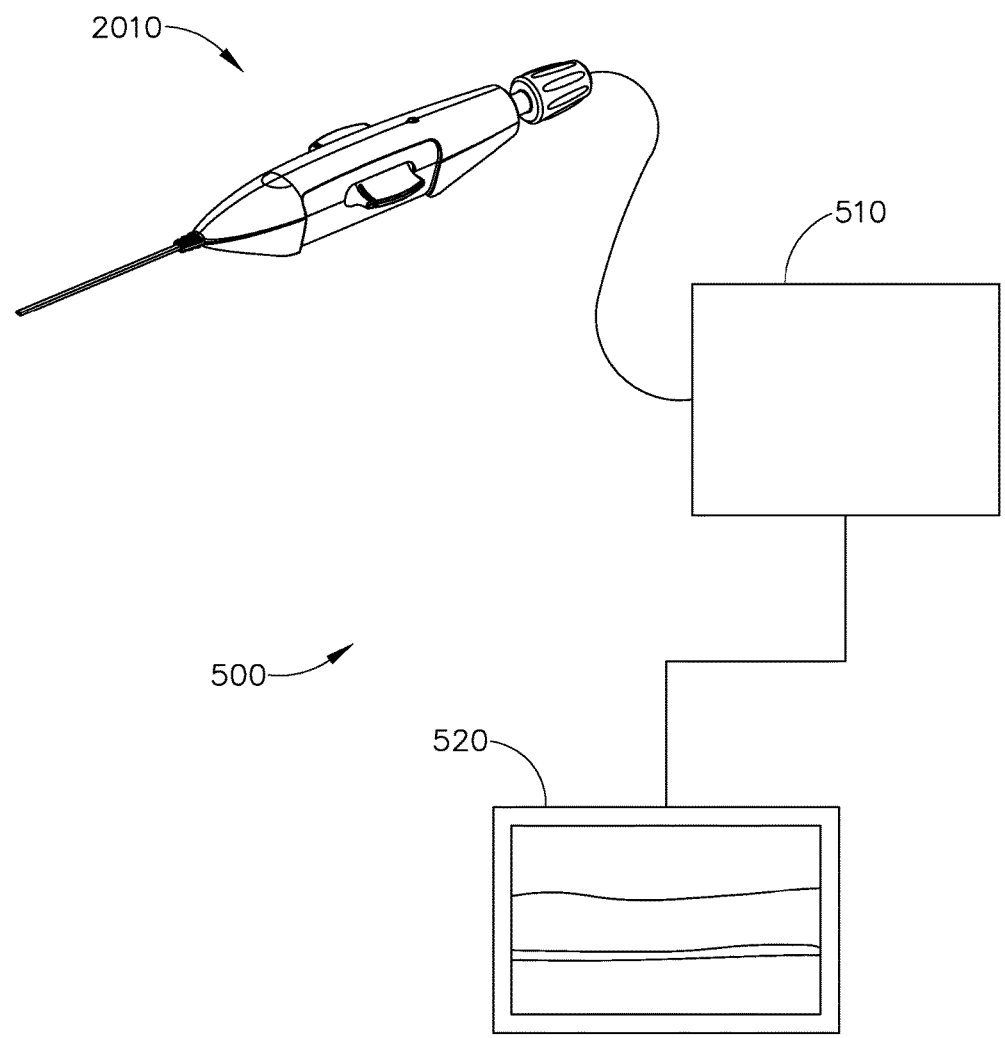
FIG. 12 depicts a schematic view of an exemplary system for subretinal administration of a therapeutic agent from a suprachoroidal approach.

In the present example, the amount of therapeutic agent (341) that is ultimately delivered to the delivery site is approximately 50 µL, although any other suitable amount may be delivered. In some versions, a foot pedal is actuated in order to drive agent (341) out from needle (30). Alternatively, other suitable features that may be used to drive agent (341) out from needle (30) will be apparent to those of ordinary skill in the art in view of the teachings herein. Delivery of therapeutic agent (341) may be visualized by an expansion of the pocket of fluid as can be seen in FIGS. 9J, 10G, and 11C. As shown, therapeutic agent (341) essentially mixes with the fluid of leading bleb (340) as therapeutic agent (341) is injected into the suprachoroidal space.

Once delivery is complete, needle (30) may be retracted by sliding actuation assembly (60) proximally relative to body (40); and cannula (20) may then be withdrawn from eye (301). It should be understood that because of the size of needle (30), the site where needle (30) penetrated through choroid (306) is self sealing, such that no further steps need be taken to seal the delivery site through choroid (306). Suture loop assembly (330) and chandelier (314) may be removed, and incision (316) in the sclera (304) may be closed using any suitable conventional techniques.

As noted above, the foregoing procedure may be carried out to treat a patient having macular degeneration. In some such instances, the therapeutic agent (341) that is delivered by needle (30) may comprise cells that are derived from postpartum umbilicus and placenta. As noted above, and by way of example only, the therapeutic agent (341) may be provided in accordance with at least some of the teachings of U.S. Pat. No. 7,413,734, entitled "Treatment of Retinitis Pigmentosa with Human Umbilical Cord Cells," issued Aug. 19, 2008, the disclosure of which is incorporated by reference herein. Alternatively, needle (30) may be used to deliver any other suitable substance or substances, in addition to or in lieu of those described in U.S. Pat. No. 7,413,734 and/or elsewhere herein. By way of example only, therapeutic agent (341) may comprise various kinds of drugs including but not limited to small molecules, large molecules, cells, and/or gene therapies. It should also be understood that macular degeneration is just one merely illustrative example of a condition that may be treated through the procedure described herein. Other biological conditions that may be addressed using the instruments and procedures described herein will be apparent to those of ordinary skill in the art.

It should also be understood that the procedure described above may be carried out in accordance with any of the teachings of U.S. patent application Ser. No. 14/619,256, entitled "Method and Apparatus for Suprachoroidal Administration of Therapeutic Agent," filed Feb. 11, 2015, the disclosure of which is incorporated by reference herein. Similarly, instrument (10, 2010) may be constructed in accordance with at least some of the teachings of U.S. patent application Ser. No. 14/619,256. Various suitable ways in which the teaching herein may be combined with the teachings of U.S. patent application Ser. No. 14/619,256 will be apparent to those of ordinary skill in the art.

V. Exemplary Suprachoroidal Sensing Systems

In some examples, it may be desirable to provide instruments (10, 2010) with features that are operable to indicate when needles (30, 2030) have fully penetrated choroid (306) so as to minimize the risk of needles (30, 2030) perforating retina (308). In particular, it may be desirable to provide features that provide an operator with real time feedback indicating when distal end (32) of needle (30, 2030) has passed through Bruch's membrane (i.e., the innermost layer of the choroid (306)) and into the subretinal space. As will be described in more detail below, instruments (10, 2010) may include sub-surface imaging technology that is operable to provide operators with images of tissue layers in the eye. Additionally or alternatively, instruments (10, 2010) may include light-emitting features that are operable to direct light through retina (308) after penetrating choroid (306). Instruments having the above referenced variations may be desirable for different surgical procedures, or surgical procedures similar to the procedure discussed above, to engage tissue structures having varying physical properties. While certain examples of variations are described herein, it should be understood that the instruments described herein may include any other alternative features as will be apparent to those of ordinary skill in the art in view of the teachings herein.

A. Exemplary Surgical System with Interferometer

FIGS. 12-24B show an exemplary surgical system (500) that is operable to perform the therapeutic agent delivery procedure described above. System (500) of the present example comprises instrument (2010), an interferometer system (510), and a display (520). Although system (500) will be described below as including instrument (2010), it should be appreciated that instrument (10) or other variations of instrument (2010) may be readily used in lieu of instrument (2010). Further, although system (500) of the present example includes display (520), it should be appreciated that display (520) is merely optional and instrument (2010) may be configured to provide visual and/or tactile feedback to an operator in addition to or in lieu of display (520). For instance, instrument (2010) may be configured to provide visual and/or tactile feedback to an operator once needle (2030) has penetrated choroid (306) but prior to perforating retina (308).

Figure 13:
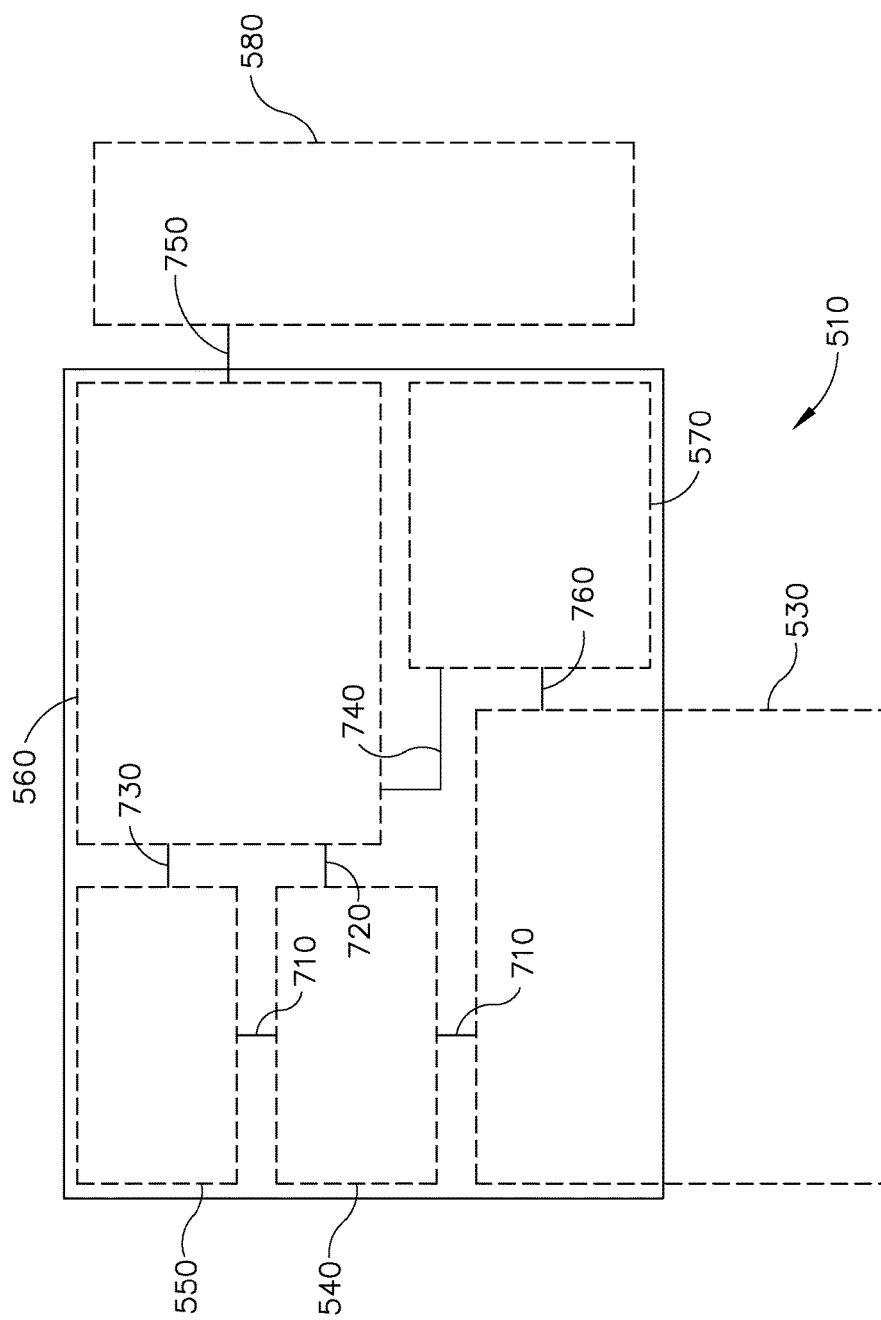
FIG. 13 depicts a schematic view of an exemplary interferometer sub-system of the system of FIG. 12.

As will be understood by one of ordinary skill in the art, and as will be described in more detail below, interferometer system (510) is operable to obtain images of tissue layers within the eye. In particular, interferometer system (510) is operable to provide an operator with an optical coherence tomography (OCT) scan that depicts sub-surface layers of the eye. Interferometer system (510) of the present example comprises a dispersive white-light interferometer (D-WLI), though it should be understood that any other suitable interferometer may be used as will be apparent to those of ordinary skill in the art in view of the teachings herein. FIG. 13 shows how interferometer system (510) is formed by several subsystems, each subsystem having its own set of components. In particular, FIG. 13 shows how interferometer system (510) of the present example comprises a power supply (530), a light source system (540), a position tracking system (550), a fiber optic assembly (560), a spectrometer (570), and an optical probe system (580). While interferometer system (510) is shown as being separate from yet coupled with instrument (2010), it should be understood that all or some of interferometer system (510) may be incorporated into instrument (2010). For instance, in some variations, power supply (530) is separate from yet coupled with instrument (2010); while the remainder of interferometer system (510) is incorporated directly into instrument (2010).

Figure 14:
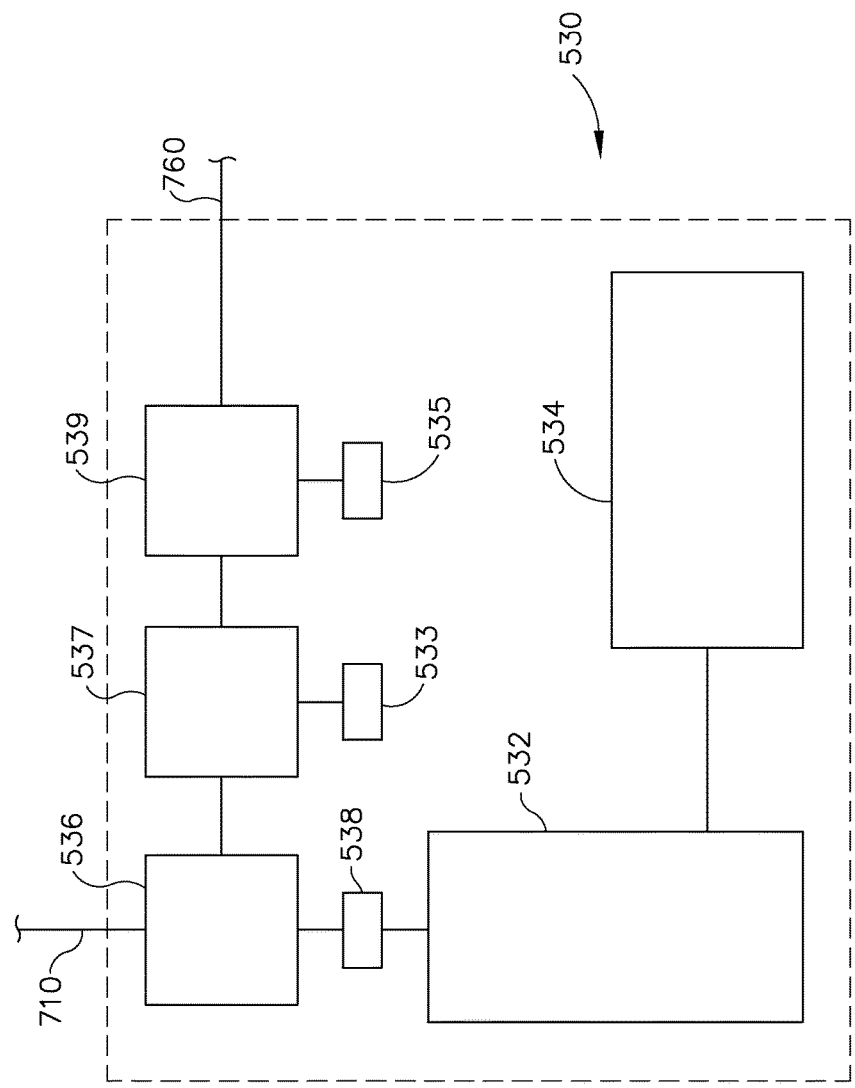
FIG. 14 depicts a detailed schematic view of an exemplary power supply of the interferometer system of FIG. 13.

Power supply (530) is operable to provide power to interferometer system (510). As shown in FIG. 14, power supply (530) of the present example includes an AC/DC power supply (532) connected to an AC power network (534) (e.g., via a conventional cable and wall outlet). AC/DC power supply (532) is further connected to a connection and power distribution/adaptation board (536) via a power supply connector (538). An electrical cable (710) extends from power distribution/adaptation board (536) to light source system (540) as will be described in greater detail below. Power supply (530) further includes a data acquisition board (537) and a line sensor board (539) both of which are connectable with external devices via respective USB connectors (533, 535). Of course, power supply (530) may alternatively include any other suitable components or features in addition to or in lieu of those described above.

Figure 15:
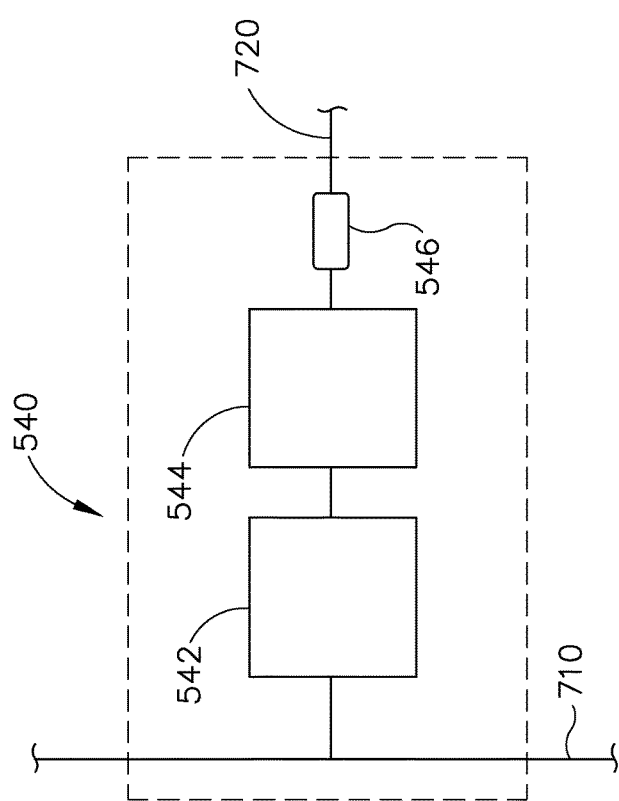
FIG. 15 depicts a detailed schematic view of an exemplary light source of the interferometer system of FIG. 13.

As shown in FIG. 15, light source system (540) of the present example includes a driver (542). Driver (542) is connected with connection and power distribution/adaptation board (536) of power supply (530) via cable (710), such that power supply (530) is operable to deliver electrical power to driver (542) via cable (710). Driver (542) is electrically coupled with light source system (540) such that driver (542) regulates the delivery of electrical power to light source (544). In the present example, light source (544) is operable to generate light in the near-infrared (NIR) spectrum, though it should be understood that light source (544) may alternatively be configured to generate light elsewhere along the spectrum of light. Light source (544) is optically coupled with optical isolator (546) via an optical cable. Optical isolator (546) comprises a conventional optical isolator that is operable to provide one-way communication of light from light source (544), preventing light from being communicated back to light source (544). Optical isolator (544) is further coupled with fiber optic assembly (560) via an optical cable (720). Of course, light source system (540) may alternatively include any other suitable components or features in addition to or in lieu of those described above.

Figure 16:
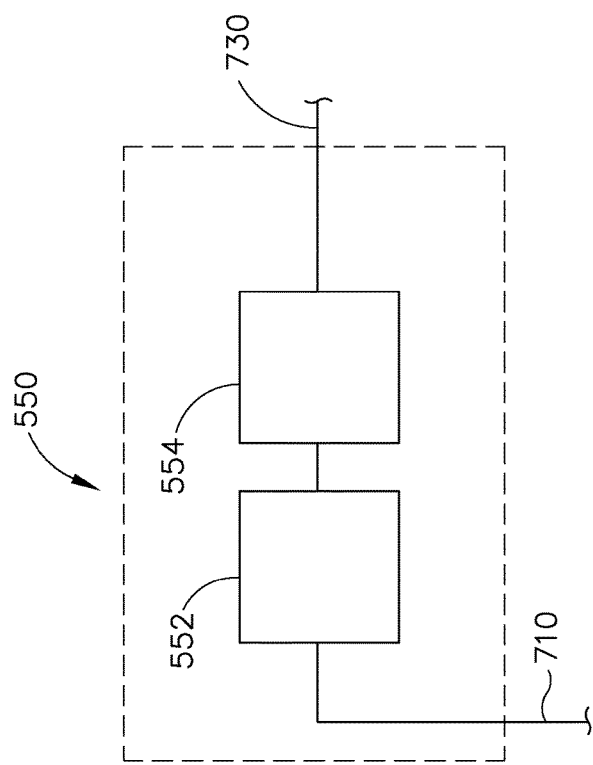
FIG. 16 depicts a detailed schematic view of an exemplary position tracking system of the interferometer system of FIG. 13.

Position tracking system (550) is also coupled with cable (710), such that position tracking system (550) also receives electrical power from power supply (530) via cable (710). As shown in FIG. 16, position tracking system (550) also includes a driver (552). Driver (552) is connected with connection and power distribution/adaptation board (536) of power supply (530) via cable (710). Position tracking system (550) further includes a tracking light source (554) which is connected with driver (552) and is powered by driver (552). Tracking light source (554) is operable to generate light in the visible spectrum. It should be understood, however, that tracking light source (554) may alternatively be configured to generate light elsewhere along the spectrum of light. Tracking light source (554) is further coupled with fiber optic assembly (560) via an optical cable (730). Of course, position tracking system (550) may alternatively include any other suitable components or features in addition to or in lieu of those described above.

Figure 17:
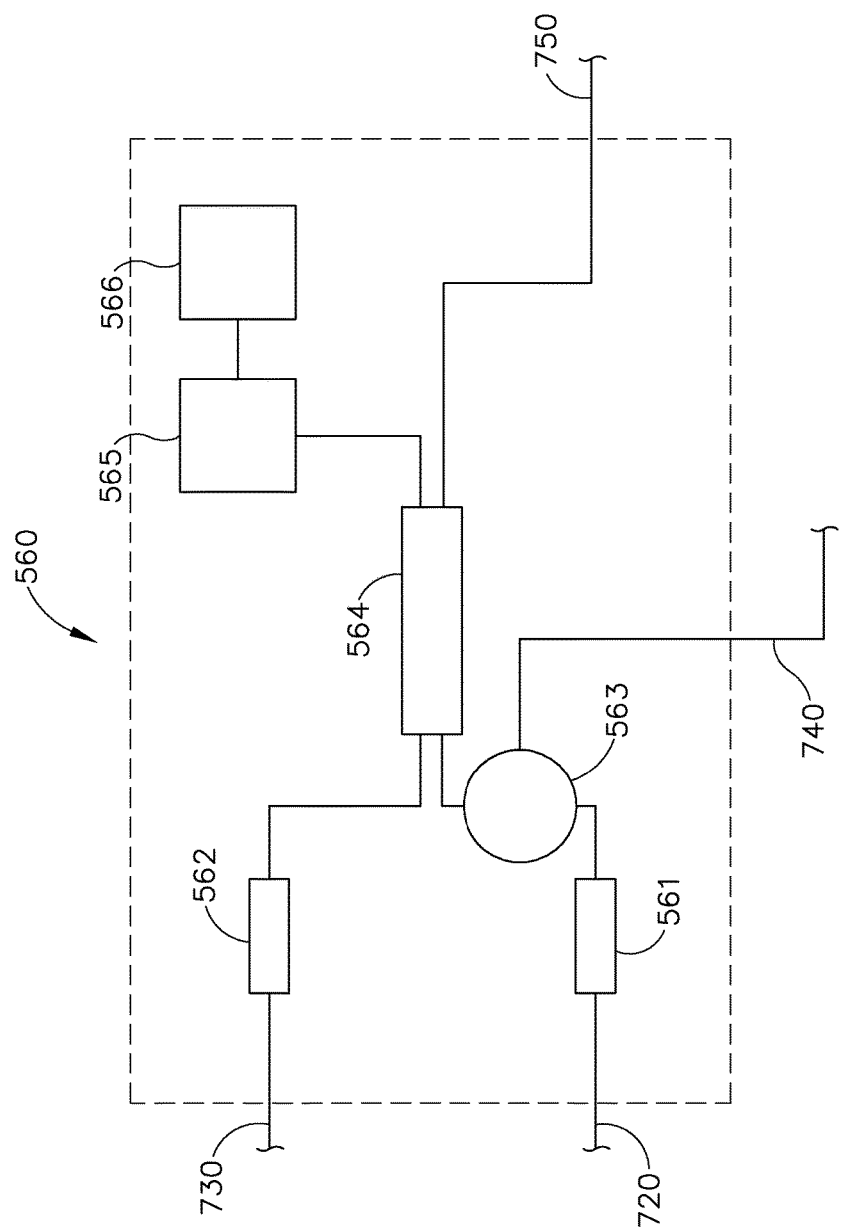
FIG. 17 depicts a detailed schematic view of an exemplary interferometer of the interferometer system of FIG. 13.

As shown in FIG. 17, fiber optic assembly (560) comprises a pair of optical connectors (561, 562). Optical connector (561) is connected to cable (720) from optical isolator (546) of light source system (540). Optical connector (562) is connected to cable (730) from tracking light source (554) of position tracking system (550). Optical connector (561) is further connected with an optical circulator (563). An optical output cable (740) is also coupled with optical circulator (563), leading to spectrometer (570) as will be described in greater detail below. Optical connector (562) and optical circulator (563) are connected to a fiber coupler (564).

Fiber coupler (564) is further connected with a beam collimator (565) and an optical cable (750) that leads to optical probe system (580) as will be described in greater detail below. Beam collimator (565) is operable to project light toward an adjustable optical delay line (566). In the present example, a portion of adjustable optical delay line (566) is manually movable toward and away from beam collimator (565) in order to selectively adjust delay. In particular, a delay line (556) adjustment is used to scan the interferometer path length in order to tune the signal. In some versions, fiber optic assembly (560) has two optical lines—one that is used as reference, and another one to measure. The best quality or strength may be achieved when these two lines have the same (exact) optical length. However, when there are several interfaces on the measurement line side, there may be no guarantee that any of these interfaces are exactly at the location equal to the reference line path. Therefore, in the present example, an operator may change the reference line (which is provided by optical delay line (566)) to adjust the reference line length, such that it would be exactly the sample length as the targeted interface. In this way, the operator may exactly tune on the desired interface rather than having a general field of view. Of course, fiber optic assembly (560) may alternatively include any other suitable components or features in addition to or in lieu of those described above.

Figure 18:
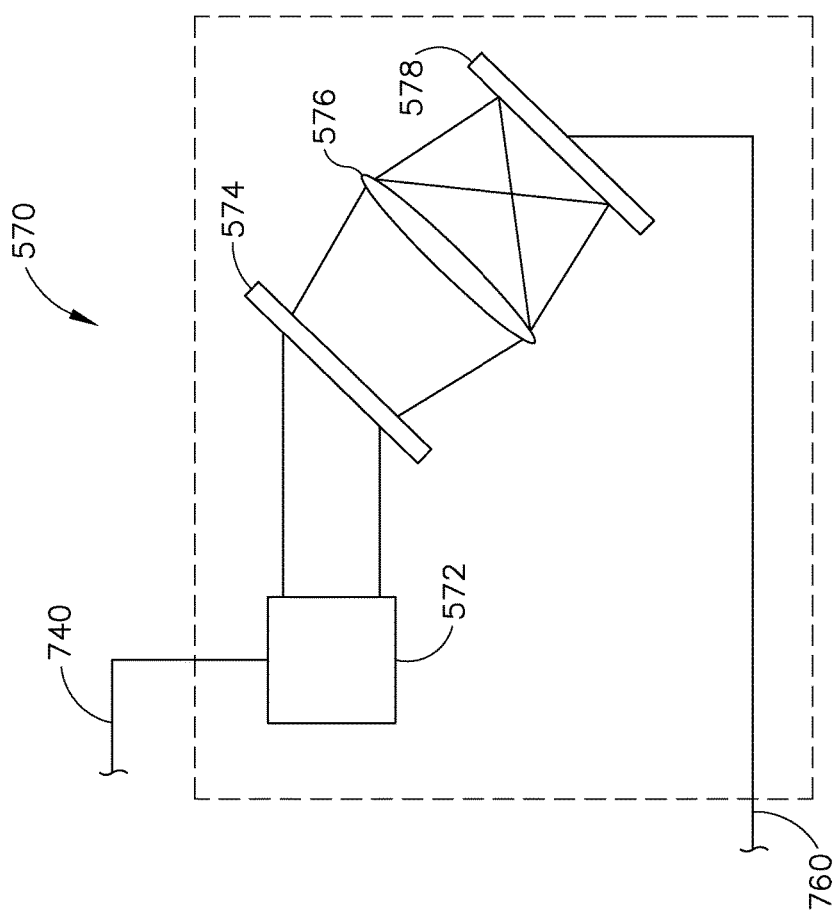
FIG. 18 depicts a detailed schematic view of an exemplary spectrometer of the interferometer system of FIG. 13.

As shown in FIG. 18, spectrometer (570) also includes a beam collimator (572) connected with cable (740) from circulator (563) of fiber optic assembly (560). Beam collimator (572) is operable to project light toward a grating (574) which in turn splits (or defracts) light toward a lens (576). Light passes through lens (576) toward an optical sensor (578). By way of example only, optical sensor (578) may comprise a CCD sensor, a CMOS sensor, and/or any other suitable kind of optical sensor. Optical sensor (578) is connected with line sensor board (539) of power supply (530) via an electrical cable (760), such that optical sensor (578) receives electrical power from power supply (530) via cable (760). Cable (760) is also configured to communicate data from optical sensor (578) to power supply (530), such that the data may be received and processed by data acquisition board (537) as described below. Of course, spectrometer (570) may alternatively include any other suitable components or features in addition to or in lieu of those described above.

Figure 19:
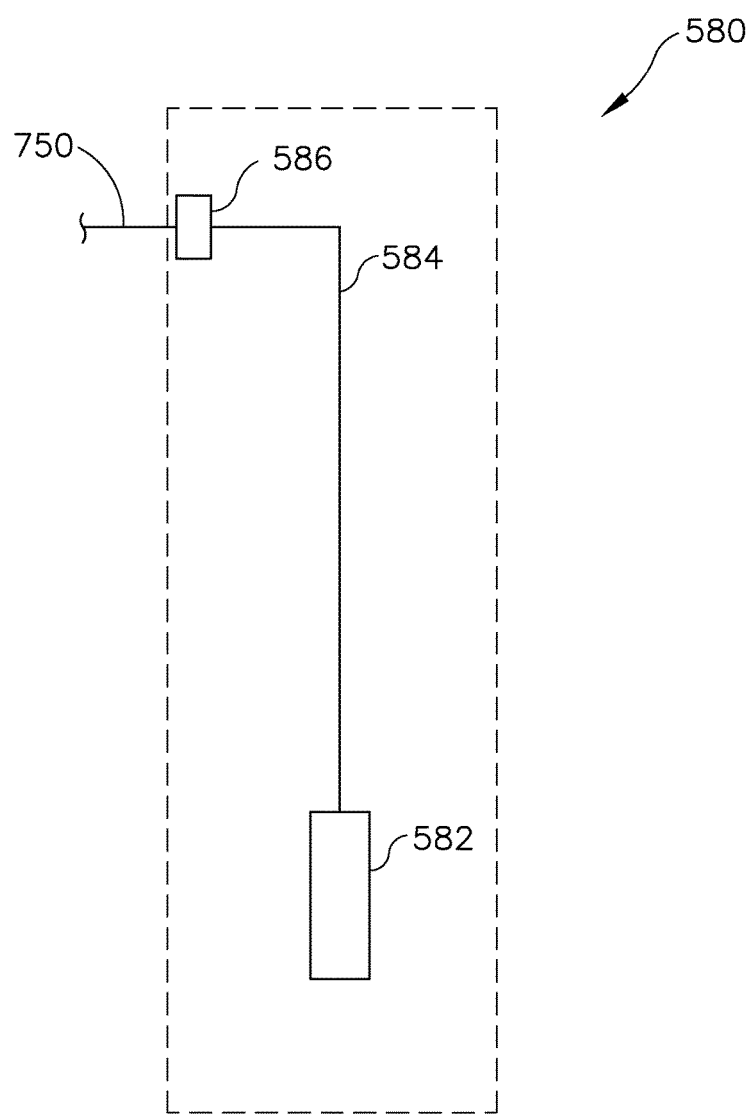
FIG. 19 depicts a detailed schematic view of an exemplary optical probe of the interferometer system of FIG. 13.

As shown in FIG. 19, optical probe system (580) includes an optical connector (586) that is coupled with optical fiber (750) of fiber optic assembly (560). Optical connector (586) is further coupled with an optical probe (582) via an optical fiber (584). By way of example only, optical fiber (584) may comprise light guiding flexible fused silica capillary tubing, with a core of approximately 150 µm, a clad of approximately 165 µm, and a buffer of approximately 195 µm. Alternatively, optical fiber (584) may have any other suitable configuration.

Figure 20:
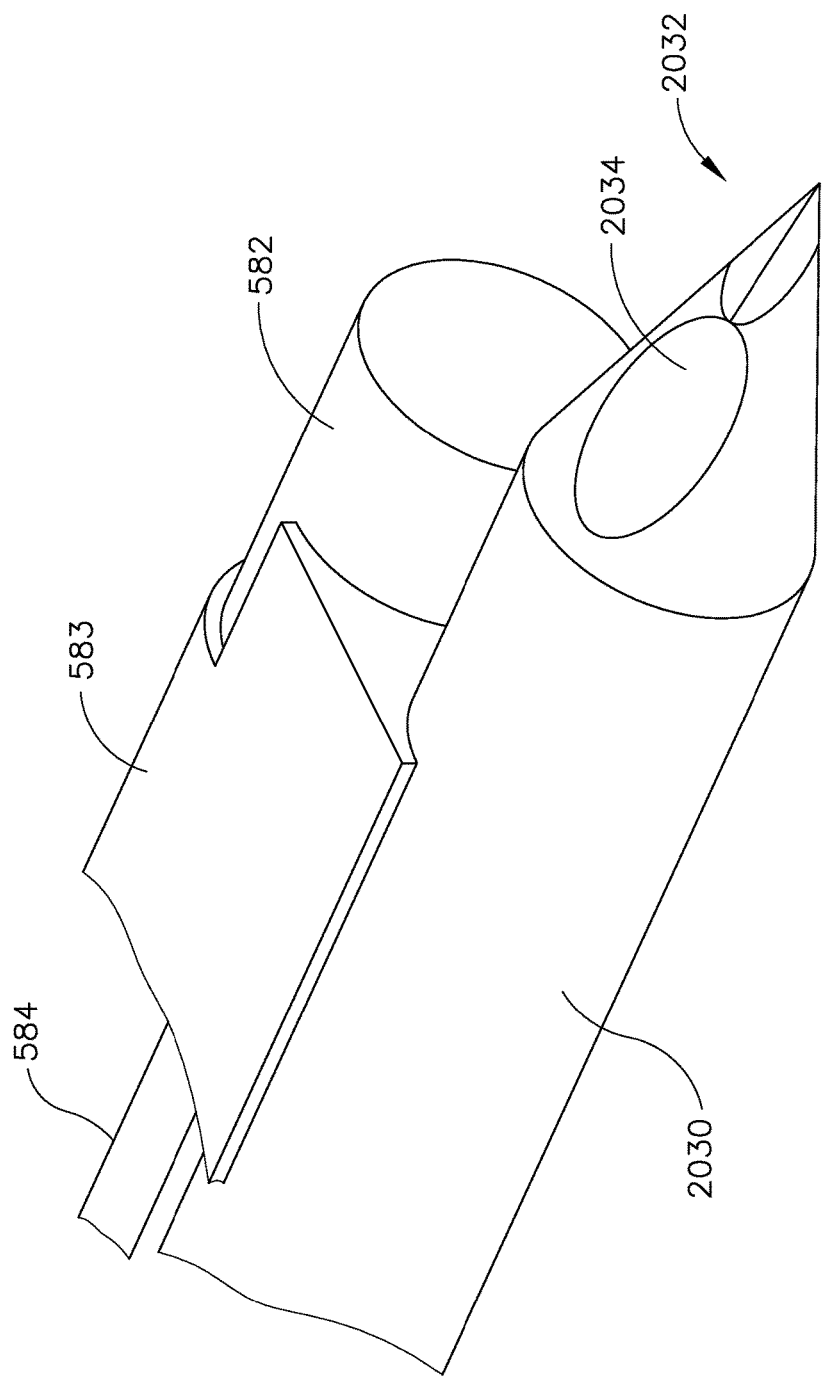
FIG. 20 depicts a perspective view of the distal end of the needle of the instrument of FIG. 1 and the optical probe of FIG. 19.
Figure 21:
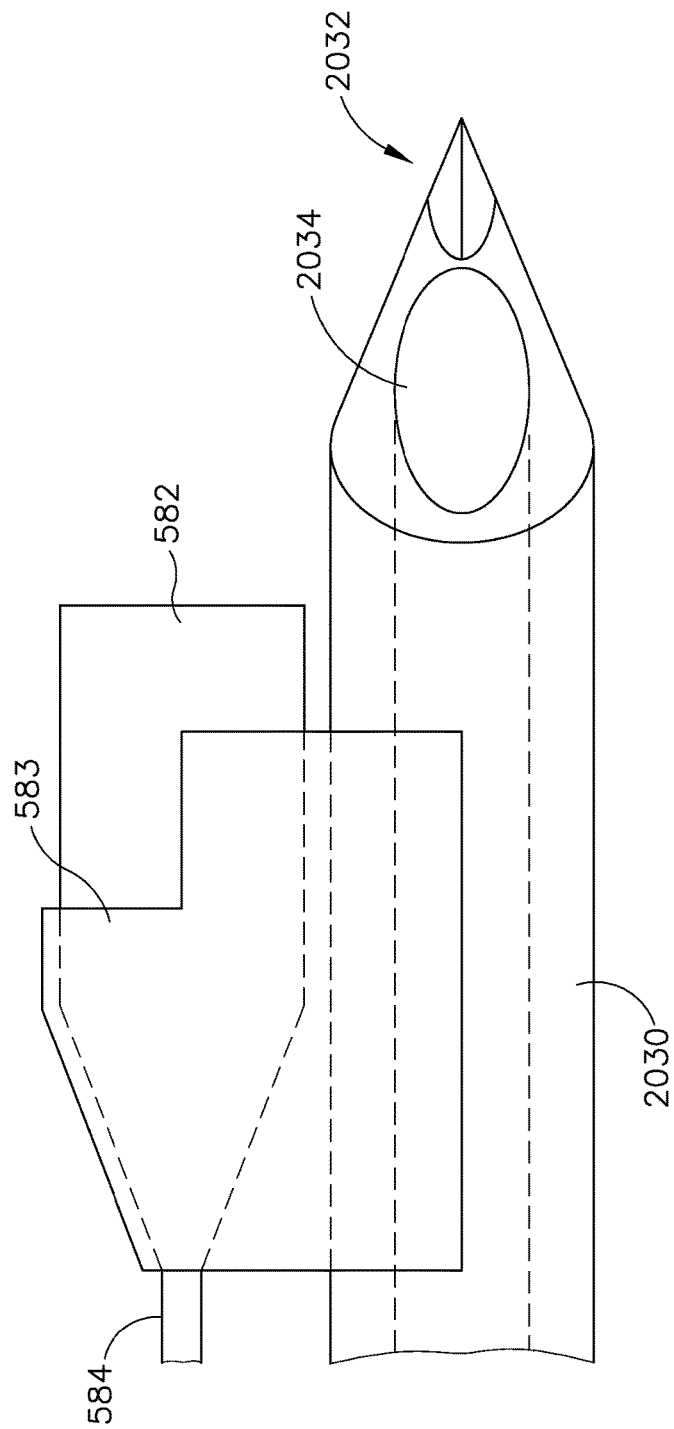
FIG. 21 depicts a top view of the distal end of the needle and probe combination of FIG. 20.

As shown in FIGS. 20 and 21, optical probe (582) is coupled with distal end (2032) of needle (2030) via an adhesive layer (583) such that optical probe (582) is configured to translate concurrently with needle (2030) within internal lumen (84) of needle guide (80) and further with needle (2030) as needle (2030) is directed out of cannula (20) along exit axis (EA) as needle (2030) penetrates the choroid (306). It should be understood that any suitable structures or techniques may be used to secure optical probe (582) with needle (2030), including but not limited to epoxies, clips, etc. Optical probe (582) of the present example is oriented substantially parallel with needle (2030) and is positioned adjacent an exterior side surface of needle (2030). Alternatively, optical probe (582) may be positioned adjacent the exterior surface of needle (2030) at any other appropriate position. For instance, optical probe (582) may be positioned adjacent an exterior top or bottom surface of needle (2030).

As yet another merely illustrative example, optical probe (582) may be positioned in lumen (2034) of needle (2030), with the distal end of optical probe (582) being longitudinally positioned to coincide with the longitudinal position of distal end (2032) of needle (2030). In some such versions, the inner diameter of lumen (2034) is sufficiently larger than the outer diameter of optical probe (582) such that leading bleb (340) and therapeutic agent (341) may flow past optical probe (582) and out of distal end (2032), while optical probe (582) is positioned within lumen (2034). Lumen (2034) may thus be coupled with a fluidic-optical junction that enables the communication of both fluids (e.g., fluid for leading bleb (340) and therapeutic agent (341)) and optical probe (582) through lumen (2034). Various suitable forms that such a fluidic-optical junction may take will be apparent to those of ordinary skill in the art in view of the teachings herein. In some other versions, optical probe (582) is removed from lumen (2034) before leading bleb (340) and therapeutic agent (341) are communicated through lumen (2034).

As best seen in FIG. 21, in the present example optical probe (582) is laterally offset from needle (2030) such that a gap exists between an exterior surface of optical probe (582) and the exterior surface of needle (2030) into which adhesive layer (583) may be positioned. Such a gap may be between 5-50 micrometers thick. Alternatively, optical probe (582) and needle (2030) may abut one another. Further, optical probe (582) of the present example is positioned relative to needle (2030) such that a distal end of optical probe (582) is positioned proximally of the distal end of needle (2030). Optical probe (582) may, however, be positioned at any appropriate position along the length of needle (2030).

Figure 22:
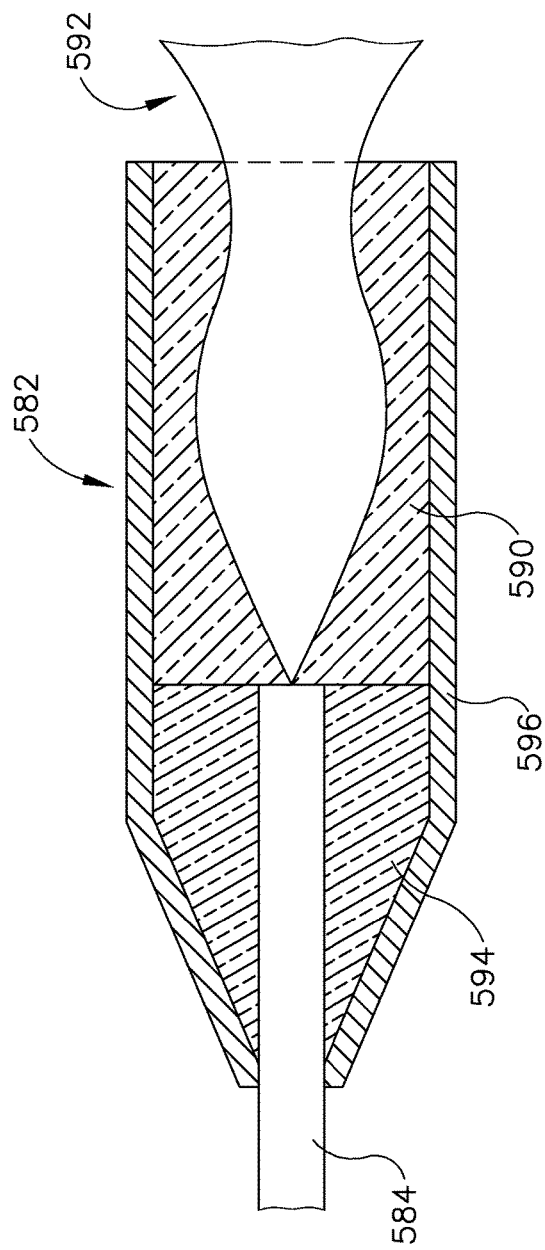
FIG. 22 depicts a side cross-sectional view of the optical probe of FIG. 19.

As shown in FIG. 22, optical probe (582) comprises a gradient-index (GRIN) lens (590), a ferrule (594), and a protective sleeve (596). Optical fiber (584) passes through ferrule (594) and projects an optical beam (592) through GRIN lens (590). Protective sleeve (596) is positioned about GRIN lens (590) and ferrule (594) to prevent damage to optical probe (582). In some versions, optical probe (582) may be within the range of approximately 1.2 mm to 2.0 mm in length and approximately 250 µm in diameter. GRIN lens (590) may within the range of approximately 0.6 mm to 1.0 mm in length and approximately 250 µm in diameter. Ferrule (594) may within the range of approximately 0.6 mm to 1.0 mm in length and approximately 250 µm in diameter. In some versions, adhesive layer (583) may be within the range of approximately 5 µm and 50 µm thick, thereby producing an effective diameter about optical probe (582) in the range of approximately 260 µm to 350 µm. Of course, any other suitable dimensions may be used for any of these components. For instance, some versions of optical probe (582) may have an effective diameter that is less than or equal to approximately 250 µm. Such smaller diameter may be preferred in versions where optical probe (582) is inserted into lumen (2034) of needle (2030).

It should be understood from the foregoing that optical probe (582) may be used to project light from light sources (544, 554) and receive light that is backscattered and reflected from tissue layers that are in front of optical probe (582). The backscattered and reflected light may be collected by optical sensor (578) of spectrometer (570). The corresponding data from optical sensor (578) may then be communicated to data acquisition board (537). It should be understood that the different layers of the eye may provide different respective opacities. These different opacities may provide a series of corresponding spikes in a graph plotting the changes in luminance ($\Delta L$) of backscattered or reflected light along a line of sight of optical probe (582). In other words, the spikes in changes in luminance ($\Delta L$) may represent the different layers of tissue in the eye. Data acquisition board (537) may provide the data from optical sensor (578) to various components that process the data to render optical coherence tomography (OCT) images in real time via display (520) as described below. Various suitable hardware components and software algorithms that may be used to convert data from interferometer system (510) into optical coherence tomography (OCT) images in real time via display (520) will be apparent to those of ordinary skill in the art in view of the teachings herein. It should also be understood that display (520) may be provided through a custom piece of capital equipment, a conventional video monitor, a conventional tablet, and/or any other suitable device.

Figure 23A:
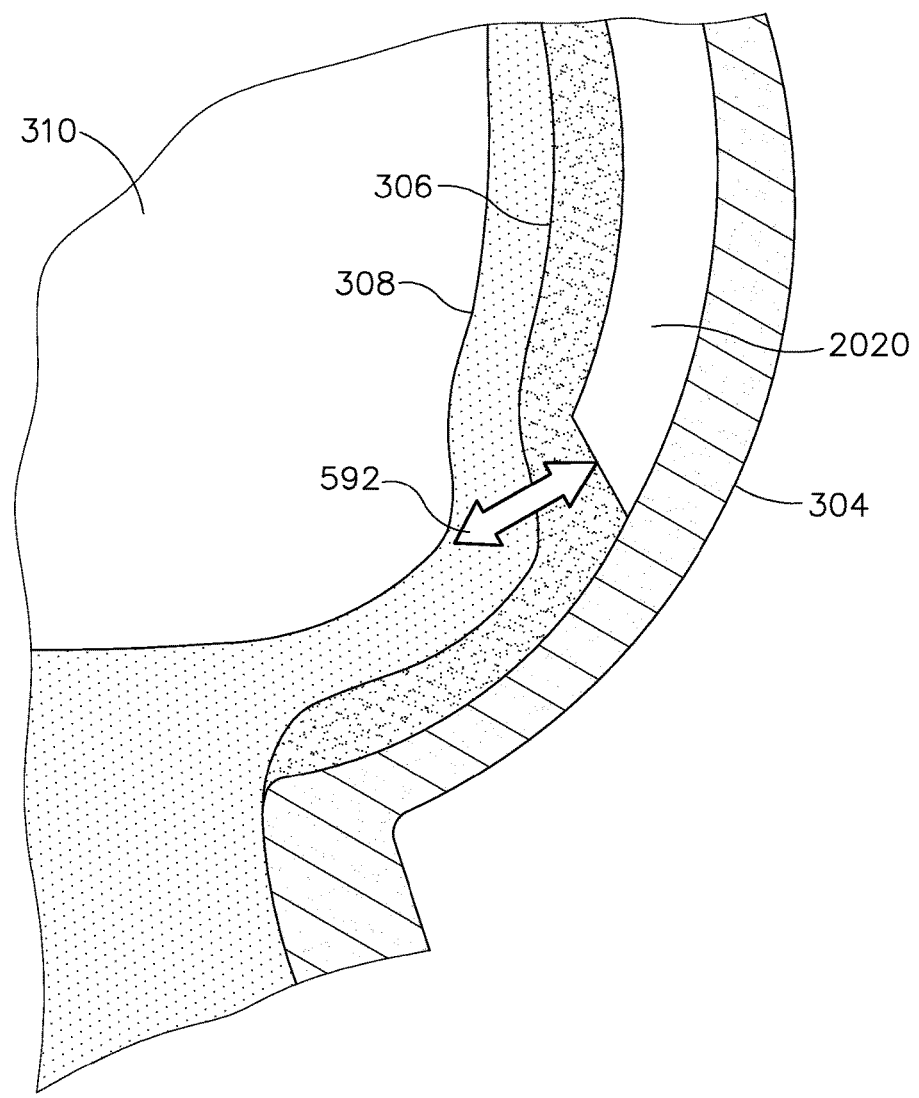
FIG. 23A depicts a detailed cross-sectional view of the eye of FIG. 9A, with the cannula of FIG. 5 under direct visualization at the back of the eye, between the sclera and choroid, and with the optical probe of FIG. 19 emitting and receiving light through the choroid and retina.
Figure 23B:
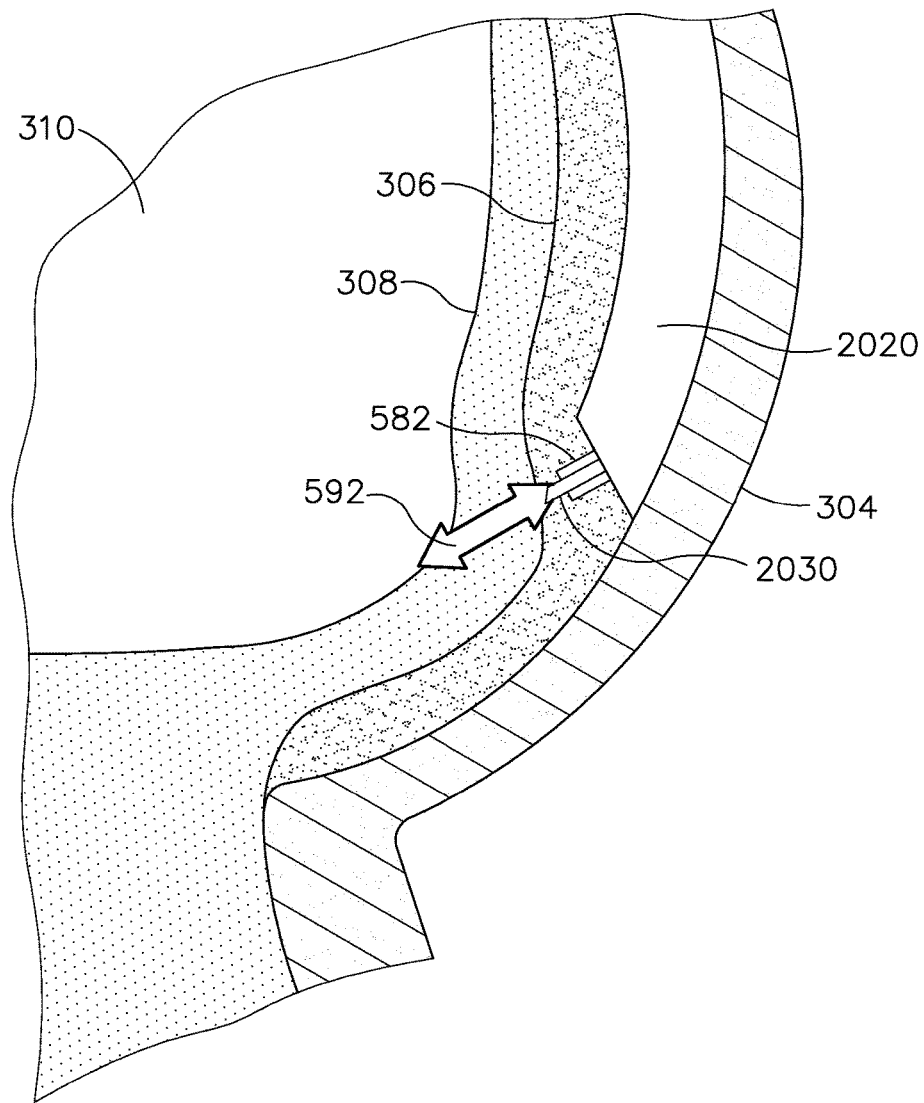
FIG. 23B depicts a detailed cross-sectional view of the eye of FIG. 9A, with the cannula of FIG. 5 being advanced under direct visualization at the back of the eye, between the sclera and choroid, and with the optical probe of FIG. 19 emitting and receiving light through the choroid and retina.
Figure 24A:
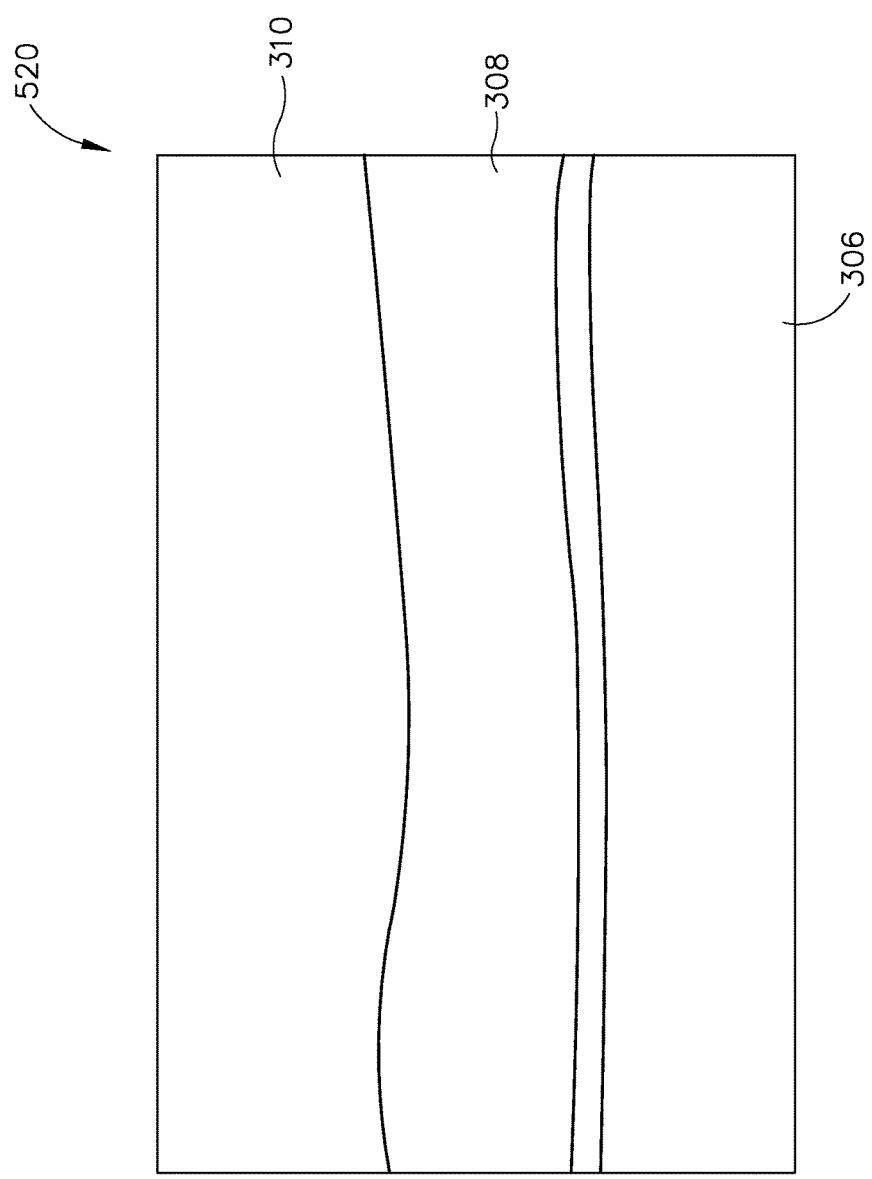
FIG. 24A depicts a diagram of an optical coherence tomography (OCT) scan taken by the optical probe of FIG. 19 at the position shown in FIG. 23A.
Figure 24B:
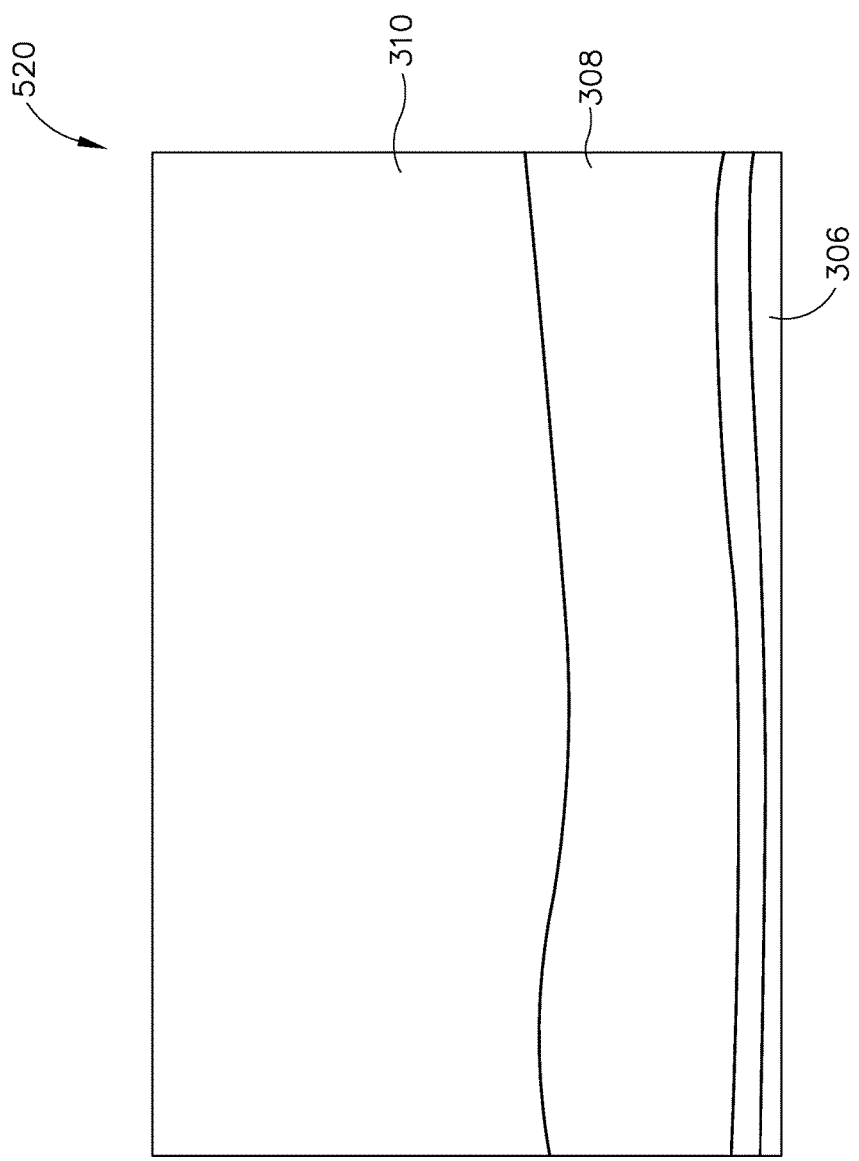
FIG. 24B depicts a diagram of an OCT scan taken by the optical probe of FIG. 19 at the position shown in FIG. 23B.

As shown in FIG. 23A, with cannula (2020) positioned at the delivery site between sclera (304) and choroid (306), needle (2030) and optical probe (582) are disposed within a distal end of cannula (2020) such that optical probe (582) projects optical beam (592) through choroid (306), retina (308), and into the vitreous region (310) of the eye to produce the image shown on display (520) as shown in FIG. 24A. From this image, an operator can tell that choroid (306) has not been pierced as choroid (306) is still visible on display (520). In other words, choroid (306) is still distal to the distal end of needle (2030) and optical probe (582). As shown in FIG. 23B, needle (2030) and optical probe (582) are advanced relative to cannula (2020) such that needle (2030) and optical probe (582) pierce choroid (306) without penetrating retina (308). From this image, an operator can visually observe through display (520) that choroid (306) has been pierced because choroid (306) has nearly disappeared from display (520). As described above, optical probe (582) of the present example is positioned relative to needle (2030) such that a distal end of optical probe (582) is positioned proximally relative to the distal end of needle (2030). Interferometer system (510) may be configured to account for this offset of optical probe (582) relative to the distal end of needle (2030) so as to provide an accurate determination of when the distal end of needle (2030) has penetrated choroid (306) and reached the subretinal space just below choroid (306).

In some versions, instrument (2010) may be configured to provide an operator with visual, audible, and/or tactile feedback to alert the operator that choroid (306) has been pierced. For instance, in some versions of instrument (2010) a computer system (not shown) may receive and process data from interferometer system (510). Such a computer system may exist as an external component relative to instrument (2010) or may be an internal component of instrument (2010). Such a computer system may be configured to alert a user in response to the occurrence of a change in luminance caused by penetration of choroid (306) thereby alerting the user that needle (2030) has reached the subretinal space just below choroid (306). Such an alert may be audible (e.g., a single beep or series of beeps), tactile (e.g., a slight vibration of instrument (2010)), or visual. For instance, instrument (2010) may include a single light or series of lights configured to illuminate or change color in response to a change in luminance as described above. Additionally, or alternatively, such lights may change color (e.g., from green to red) or intensity (e.g. from dim to bright) as needle (2030) penetrates choroid (306). Additionally, or alternatively, optical probe (582) may be configured to illuminate or change color in response to a change in luminance as described above. Additionally, or alternatively, optical probe (582) may change color (e.g., from green to red) or intensity (e.g. from dim to bright) as needle (2030) penetrates choroid (306). In some instances, the operator may prefer to receive notification from instrument (2010) in audible and/or tactile/haptic form. This may enable the operator to maintain a view through a microscope or other instrument that is used to provide a view of the retina (308), etc., without requiring the operator to divert their view from the microscope or other viewing instrument in order to receive the notification from instrument (2010).

Once the operator has been notified that choroid (306) has been pierced, such that the distal end of needle (2030) has passed through Bruch's membrane and into the subretinal space, the operator may immediately cease advancement of needle (2030) and then administer leading bleb (340) and therapeutic agent (341) in accordance with the teachings herein. Other suitable ways in which interferometer system (510) and display (520) may be used in combination with instrument (2010) will be apparent to those of ordinary skill in the art in view of the teachings herein.

B. Exemplary Surgical System with Microscope Imaging Detector

FIGS. 25-27B show another exemplary surgical system (600) that may be used to perform the therapeutic agent delivery procedure described above. System (600) of the present example comprises instrument (2010), a microscope (610), a computer (620), a servo controller (630), a modulator (640), and a light source (650). Although system (600) will be described below as including instrument (2010), it should be appreciated that instrument (10) or other variations of instrument (2010) may be readily used in lieu of instrument (2010).

Figure 25:
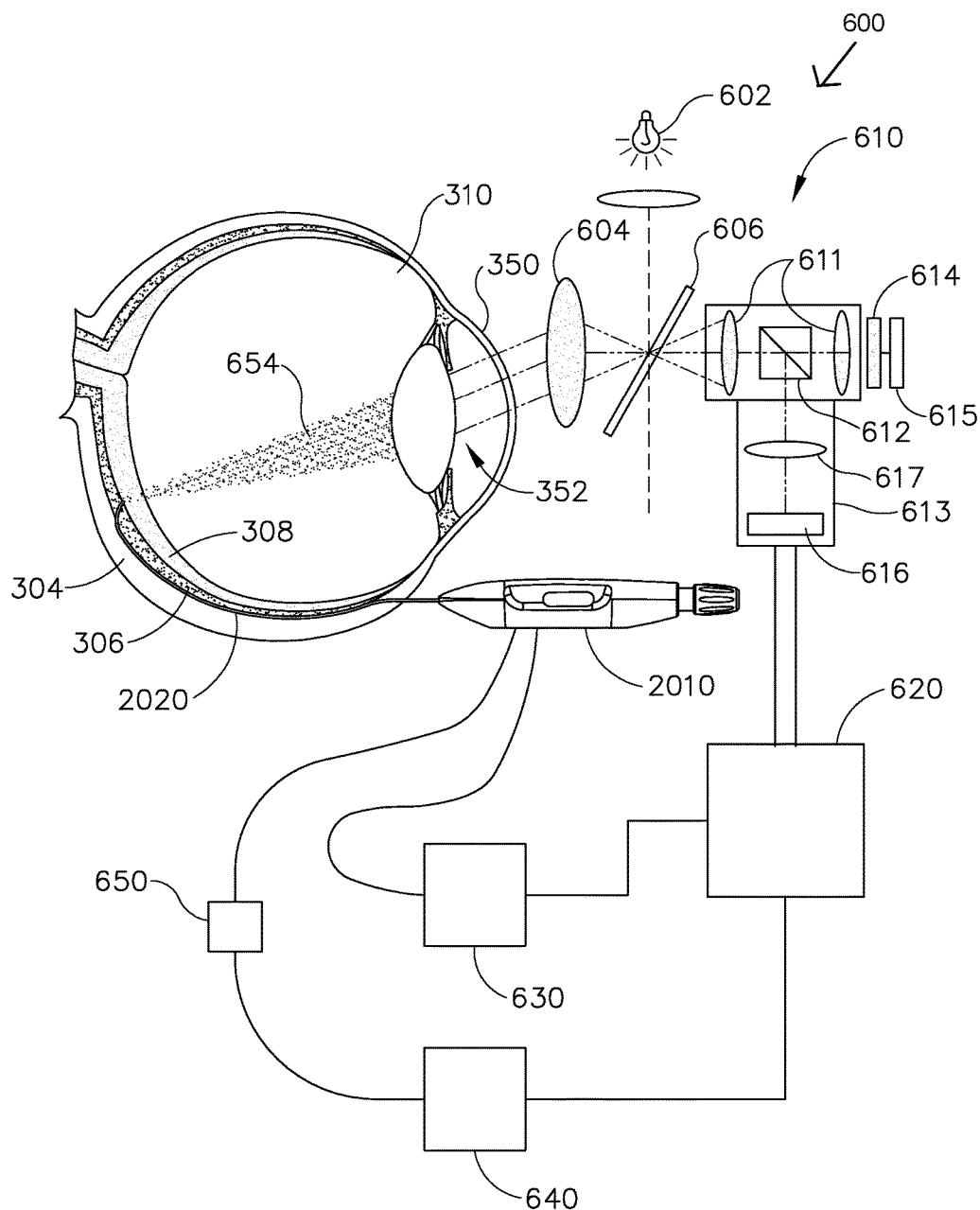
FIG. 25 depicts a schematic view of another exemplary system for subretinal administration of a therapeutic agent from a suprachoroidal approach.

As shown in FIG. 25, instrument (2010) is connected with light source (650) and servo controller (630). As will be described in more detail below, light source (650) comprises a fiber optic cable (652) that is coupled with needle (2030) such that fiber optic cable (652) is operable to translate concurrently with needle (2030). Also as will be described in more detail below, light source (650) is operable to project light from a distal end of needle (2030) into the eye via fiber optic cable (652). Light source (650), of the present example, is operable to generate visible light (i.e., with a wavelength between approximately 430 nm and 700 nm, or more specifically with a wavelength between approximately 500 nm and 600 nm), infrared light (i.e., with a wavelength greater than approximately 700 nm), and/or near-infrared light. In some versions, light source (650) provides light at a wavelength of approximately 635 nm. Light source (650) is connected with modulator (640) which is configured to modulate light provided by light source (650). In some variations, light source (650) comprises a laser. Other suitable forms that light source (650) may take will be apparent to those of ordinary skill in the art in view of the teachings herein.

Servo controller (630) is operable to control a servomotor (not shown). As discussed above, such a servomotor may be operable to drive translation of needle (2030) in addition to or in lieu of rotation member (2110). Various suitable components and features that may be used to provide actuation of needle (2030) under control of servo controller (630) will be apparent to those of ordinary skill in the art in view of the teachings herein. It should also be understood that needle (2030) may instead be driven manually (e.g., via a slider, via a screw advance, etc.), such that servo controller (630) and a servo motor may be omitted if desired.

Servo controller (630) and modulator (640) are connected with computer (620), such that computer (620) is operable to execute control algorithms to drive both servo controller (630) and modulator (640). Computer (620) is connected with a camera (613) that is coupled with microscope (610). As will be described in more detail below computer (620) is operable to control servo controller (630), the servo motor, modulator (640), and light source (650) based on feedback from camera (613). Also as will be described in more detail below, microscope (610) is operable to detect light from light source (650) shone through vitreous region (310) to thereby indicate when needle (2030) has fully penetrated choroid (306).

As shown in FIG. 25, microscope (610) is positioned adjacent the cornea (350) of the eye such that microscope (610) is operable to detect light projecting from vitreous region (310) and through the pupil (352) of the eye. This light projecting from vitreous region (310) and through the pupil (352) of the eye is configured to pass though an aspheric lens (604) so as to reduce or eliminate optical aberrations within the light. A light source (602) is configured to project visible light to provide illumination of the vitreous region (310) of the eye. The visible light from light source (602) passes through a beam splitter (606), which redirects the light to project through the pupil (352) into the vitreous region (310) of the eye. Beam splitter (606) further permits light that is projected back from the eye to pass through beam splitter (606) to reach microscope (610).

Microscope (610) of the present example includes a series of lenses (611) that are operable to provide magnification. Microscope (610) further includes a dichroic beam splitter (612) that is operable to separate light. In particular, dichroic beam splitter (612) is operable to separate light in the visible spectrum (VIS) from light in the infrared spectrum (IR). Once separated, this VIS light is passes through one or more lenses (611) within microscope (610) and then through a filter (614) so as to enable visualization by the naked eye of a user at port (615); while the IR light passes into camera (613). Camera (613) includes one or more lenses (617) through which the IR light passes so as to focus the IR light from dichroic beam splitter (612). This focused IR light then passes to an IR image sensor (616) of camera (613). Image sensor (616) of the present example may be a charge-coupled device (CCD) image sensor, a complementary metal-oxide semiconductor (CMOS) image sensor, or any other appropriate type of image sensor. In some versions, image sensor (616) is operably configured to capture images at a rate of 300 frames per second. This may provide a spatial resolution of approximately 1 µm when needle (2030) is advanced at a piercing speed of approximately 300 µm/s. Alternatively, any other suitable frame rate may be used for image sensor (616); and any other suitable piercing speed may be used for needle (2030).

Figure 26A:
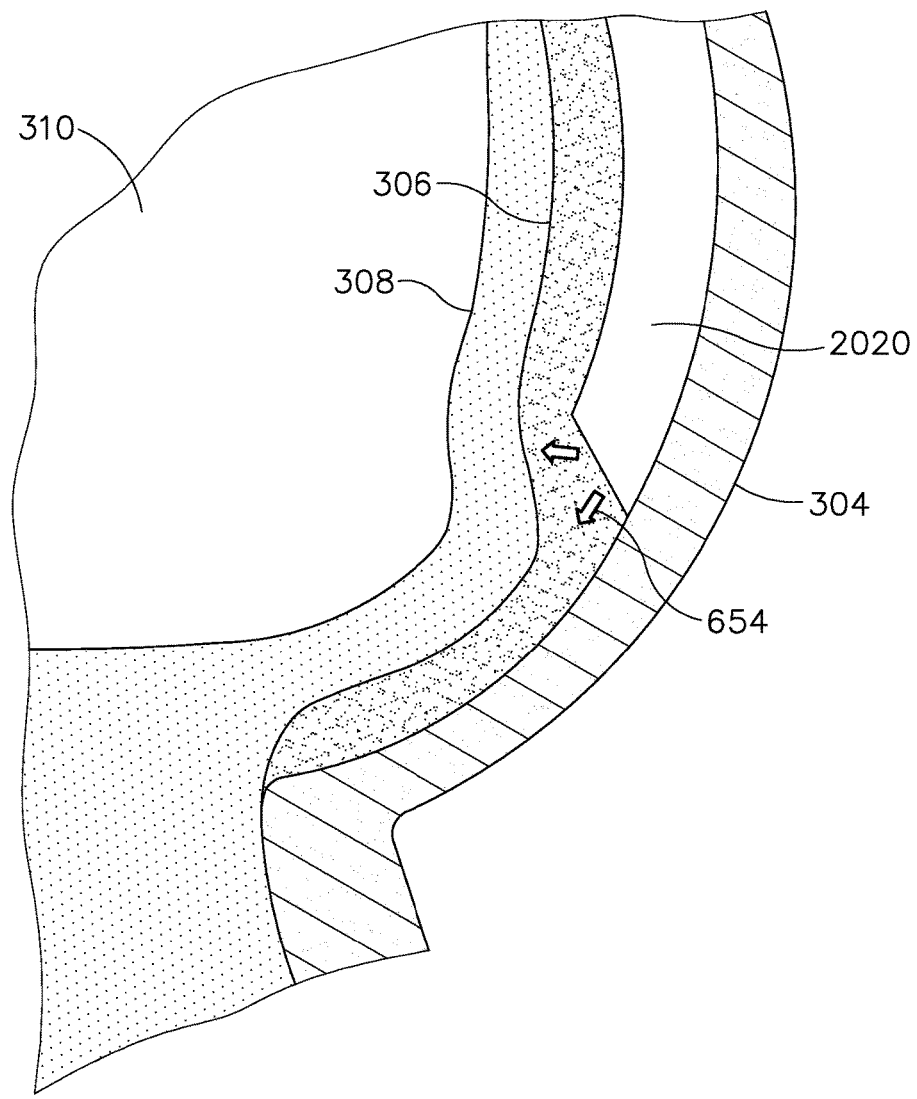
FIG. 26A depicts a detailed cross-sectional view of the eye of FIG. 9A, with the cannula of FIG. 5 under direct visualization at the back of the eye, between the sclera and choroid, and with a light source of the system of FIG. 25 emitting light into the choroid of the eye.
Figure 27A:
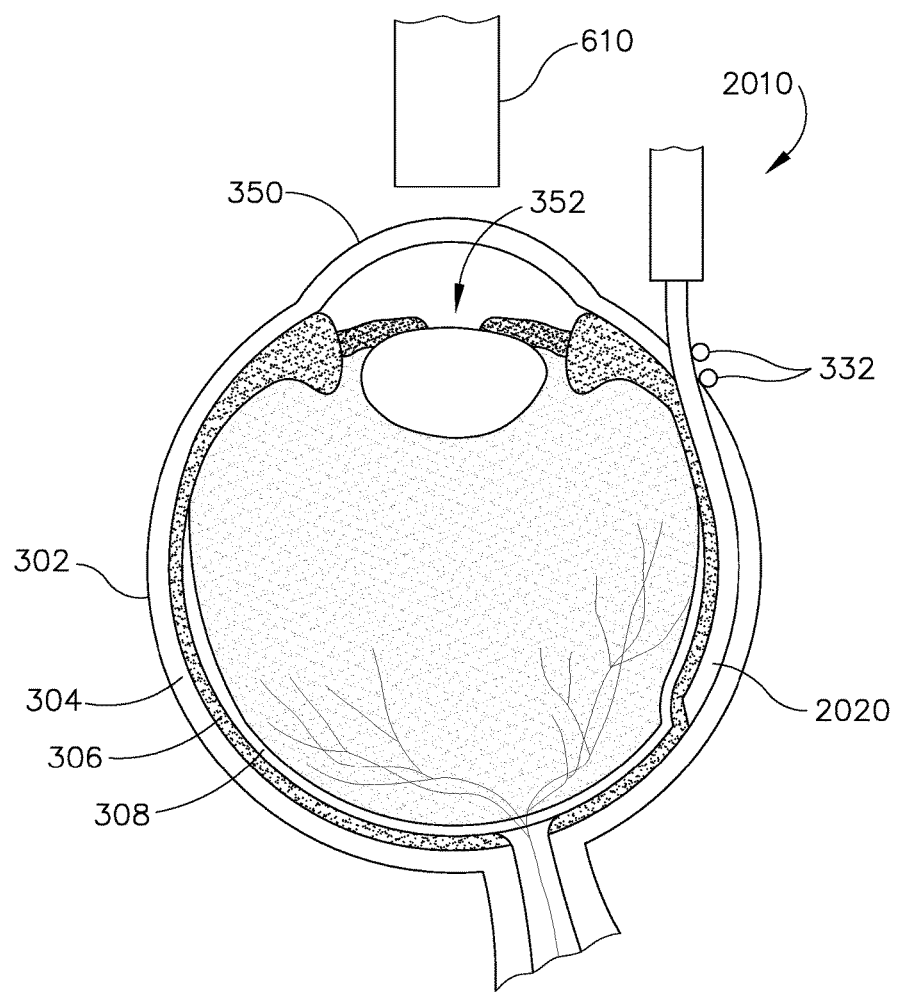
FIG. 27A depicts a detailed cross-sectional view of the eye of FIG. 9A, with the cannula of FIG. 5 under direct visualization at the back of the eye, between the sclera and choroid, and with the light source of FIG. 26A emitting light into the choroid of the eye.

As shown in FIGS. 26A and 27A, cannula (2020) is positioned between sclera (304) and choroid (306). In this position, needle (2030) and fiber optic cable (652) are disposed within a distal end of cannula (2020) such that fiber optic cable (652) projects light (654) into choroid (306). Because of the relatively opaque nature of choroid (306), light (654) from optic cable (652) does not pass through choroid (306) into retina (308) and vitreous region (310). Thus, at this point, light (654) from fiber optic cable (652) is either not visible or detectable via image sensor (616); or is partially detectable but faint.

Figure 26B:
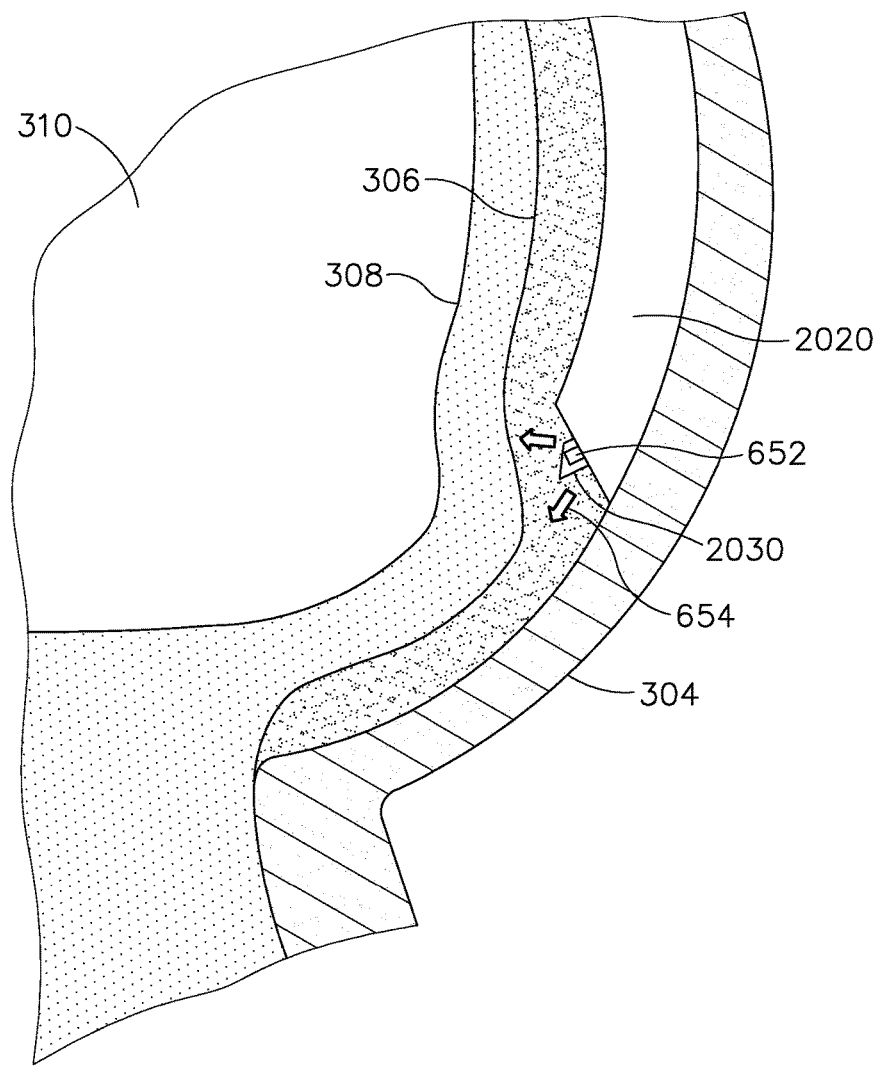
FIG. 26B depicts a detailed cross-sectional view of the eye of FIG. 9A, with the cannula of FIG. 5 being advanced under direct visualization at the back of the eye, between the sclera and choroid, and with the light source of FIG. 26A emitting light into the choroid of the eye.

As shown in FIG. 26B, needle (2030) and fiber optic cable (652) are advanced relative to cannula (2020) such that needle (2030) and fiber optic cable (652) partially pierce choroid (306). In this position, distal end (2032) of needle (2030) and fiber optic cable (652) are partially exposed relative to the distal end of cannula (2020) such that fiber optic cable (652) projects light (654) into choroid (306). Again, because of the relatively opaque nature of choroid (306), light (654) from optic cable (652) does not pass completely through choroid (306) into retina (308) and vitreous region (310). Thus, at this point, while some light (654) from fiber optic cable (652) may be visible or detectable via image sensor (616) of camera (613), the light is not so intense as to exceed a threshold associated with the fiber optic cable (652) reaching the subretinal space beyond choroid (306).

Figure 26C:
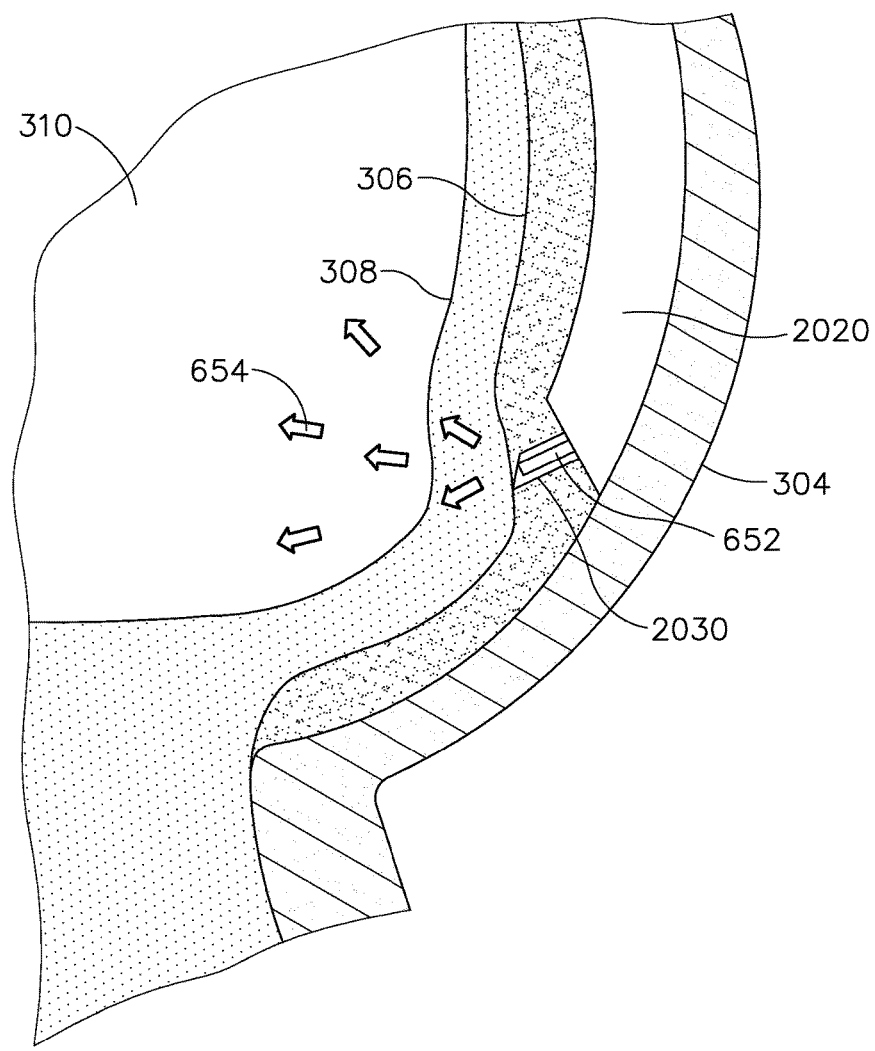
FIG. 26C depicts a detailed cross-sectional view of the eye of FIG. 9A, with the needle of the instrument of FIG. 1 being advanced further under direct visualization at the back of the eye, between the sclera and choroid, and with the light source of FIG. 26A emitting light through the retina and vitreous of the eye.
Figure 27B:
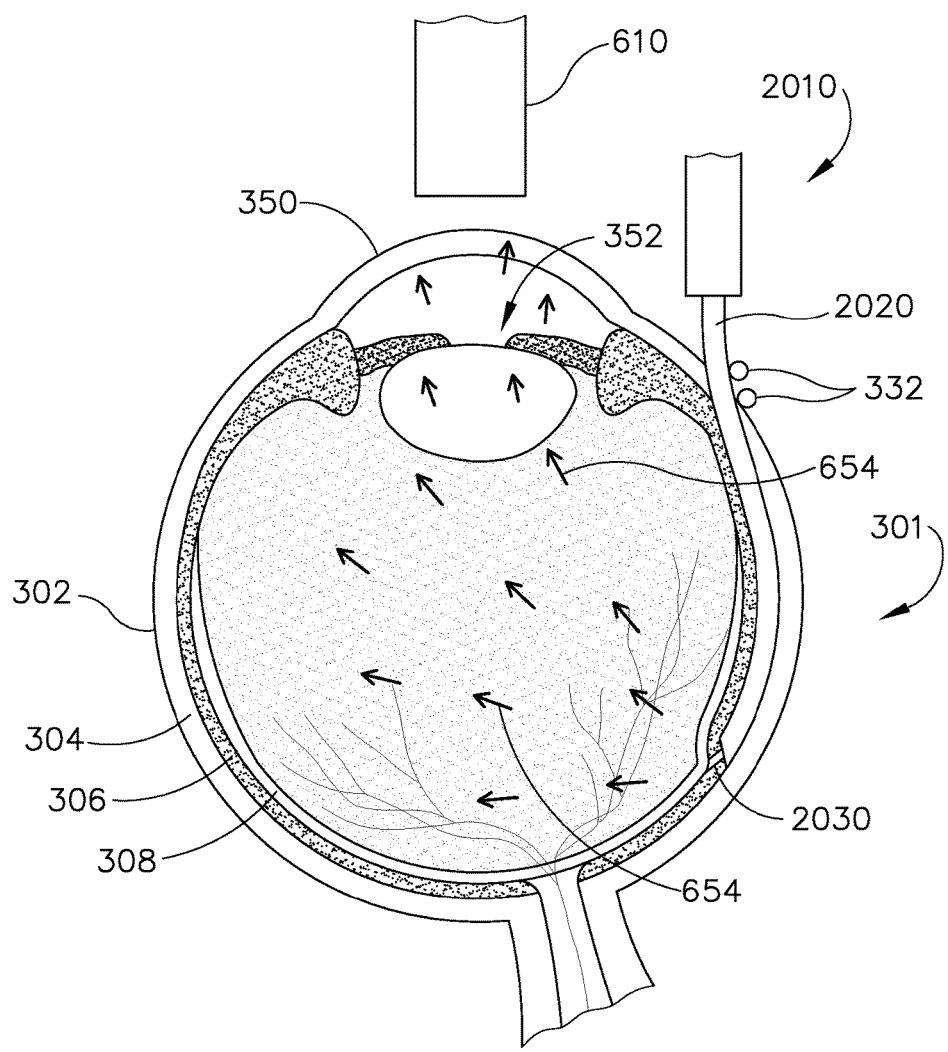
FIG. 27B depicts a detailed cross-sectional view of the eye of FIG. 9A, with the needle of the instrument of FIG. 1 being advanced under direct visualization at the back of the eye, between the sclera and choroid, and with the light source of FIG. 26A emitting light through the retinal pigment epithelium layer and the vitreous of the eye.

As shown in FIGS. 26C and 27B, needle (2030) and fiber optic cable (652) are further advanced relative to cannula (2020) such that needle (2030) and fiber optic cable (652) fully pierce choroid (306) without penetrating retina (308). In this position, fiber optic cable (652) projects light (654) into retina (308). Because of the relatively transparent nature of retina (308), light (654) from fiber optic cable (652) passes through retina (308) and into vitreous region (310). Thus, at this point, light (654) from fiber optic cable (652) is visible and/or detectable via image sensor (616) at an intensity associated with distal end (2032) of needle (2030) and fiber optic cable (652) reaching the subretinal space above the choroid (306).

Once image sensor (616) detects light (654) that exceeds the threshold intensity associated with distal end (2032) of needle (2030) and fiber optic cable (652) reaching the subretinal space above the choroid (306), computer (620) may stop the servomotor so as to prevent further translation of needle (2030) and fiber optic cable (652). In addition or in the alternative, once image sensor (616) detects light (654) that exceeds the threshold intensity associated with distal end (2032) of needle (2030) and fiber optic cable (652) reaching the subretinal space above the choroid (306), instrument (2010) may provide an audible, tactile, and/or visual signal to the operator to indicate that the subretinal space has been reached. As noted above, the operator may prefer to receive notification from instrument (2010) in audible and/or tactile/haptic form. This may enable the operator to maintain a view through a microscope or other instrument that is used to provide a view of the retina (308), etc., without requiring the operator to diver their view from the microscope or other viewing instrument in order to receive the notification from instrument (2010). In versions where needle (2030) is advanced manually instead of being advanced via servomotor, the operator may cease advancement of needle (2030) in response to the audible, tactile, and/or visual signal indicating that the subretinal space has been reached.

Regardless of how the operator is notified that the subretinal space has been reached, and regardless of how the advancement of needle (2030) is driven and stopped, the operator may then administer leading bleb (340) and therapeutic agent (341) in the subretinal space in accordance with the teachings herein. Other suitable ways in which system (600) may be used in combination with instrument (2010) will be apparent to those of ordinary skill in the art in view of the teachings herein.

It should be understood that, as distal end (2032) of needle (2030) advances through the choroid (306), the intensity of the light received by image sensor (616) increases. By way of example only, the highest jump in light intensity may occur once distal end (2032) of needle (2030) and fiber optic cable (652) pass from below the retinal pigment epithelium (RPE) to above the RPE. In some instances, the light intensity may suddenly increase by approximately 20% to approximately 40% once distal end (2032) of needle (2030) and fiber optic cable (652) perforate the RPE. The intensity of the light received by image sensor (616) may also vary based on the position of distal end (2032) of needle (2030) and fiber optic cable (652) in the eye in accordance with the teachings of Gao, et al. "Measuring Retinal Contributions to the Optical Stiles-Crawford Effect with Optical Coherence Tomography." OPTICS EXPRESS, 16.9 (2008): pp. 6486-6501, the disclosure of which is incorporated by reference herein.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system for delivering therapeutic agent to an eye, wherein the system comprises: (a) a surgical instrument, wherein the surgical instrument comprises: (i) a body, (ii) a cannula extending distally from the body, wherein the cannula is sized and configured to be insertable between a choroid and a sclera of a patient's eye, wherein the cannula defines a longitudinal axis, (iii) a hollow needle, wherein the needle is slidable relative to the cannula, and (iv) an actuation assembly, wherein the actuation assembly is operable to actuate the needle relative to the cannula to thereby drive a distal portion of the needle along an exit axis; and (b) an interferometer system comprising an optical probe, the optical probe is coupled with a distal end of the hollow needle such that the optical probe is operable to slide concurrently with the hollow needle within the cannula, wherein the interferometer system is operable to provide data indicating a position of the distal end of the hollow within a patient's eye.

Example 2

The system of Example 1, wherein the optical probe comprises a gradient-index (GRIN) lens.

Example 3

The system of any one or more of Examples 1 through 2, wherein the exit axis is oriented obliquely relative to the longitudinal axis of the cannula.

Example 4

The system of any one or more of Examples 1 through 3, wherein the interferometer system comprises a spectrometer.

Example 5

The system of any one or more of Examples 1 through 4, wherein the interferometer system is operable to provide an operator with an optical coherence tomography (OCT) scan that depicts sub-surface layers of the eye.

Example 6

The system of Example 5, wherein the system further comprises a display operable to depict the OCT scan of the interferometer.

Example 7

The system of any one or more of Examples 1 through 6, wherein the interferometer system comprises a dispersive white-light interferometer (D-WLI).

Example 8

The system of any one or more of Examples 1 through 7, wherein the interferometer system comprises a display operable to depict a choroid and a retina of a patient's eye.

Example 9

The system of any one or more of Examples 1 through 8, wherein the optical probe of the interferometer system is coupled with a distal end of the hollow needle via an adhesive layer.

Example 10

The system of any one or more of Examples 1 through 9, wherein the interferometer system is operable to provide visual, audible, and/or tactile feedback to an operator.

Example 11

The system of Example 10, wherein the interferometer system is operable to provide visual, audible, and/or tactile feedback to an operator in response to the hollow needle piercing the choroid.

Example 12

The system of any one or more of Examples 1 through 11, wherein the interferometer system comprises a position tracking system.

Example 13

The system of any one or more of Examples 1 through 12, wherein the optical probe is positioned proximally relative to a distal end of the needle.

Example 14

The system of any one or more of Examples 1 through 13, wherein the optical probe is oriented substantially parallel to the needle.

Example 15

The system of any one or more of Examples 1 through 14, wherein the optical probe is laterally offset from the needle.

Example 16

A system for delivering therapeutic agent to an eye, wherein the system comprises: (a) a surgical instrument, wherein the surgical instrument comprises: (i) a body, (ii) a cannula extending distally from the body, wherein the cannula is sized and configured to be insertable between a choroid and a sclera of a patient's eye, wherein the cannula defines a longitudinal axis, (iii) a hollow needle, wherein the needle is slidable relative to the cannula, (iv) a light-emitting fiber optic cable, wherein the fiber optic cable is operable to emit light through a patient's eye, and (v) an actuation assembly, wherein the actuation assembly is operable to actuate the needle relative to the cannula to thereby drive a distal portion of the needle along an exit axis; and (b) a microscope imaging detector, wherein the microscope imaging detector is operable to detect light emitted from the fiber optic cable through a patient's eye.

Example 17

The system of Example 16, wherein the fiber optic cable is coupled with a distal end of the needle such that the fiber optic cable is operable to slide concurrently with the needle within the cannula.

Example 18

The system of any one or more of Examples 16 through 17, wherein one or both of the instrument or the microscope imaging detector includes a feedback feature operable to provide audible, tactile, or visual feedback in response to the distal end of the needle reaching a space between a retina and a choroid of a patient's eye, based on light detected by the microscope imaging detector.

Example 19

The system of any one or more of Examples 16 through 18, wherein the actuation assembly comprises a servo motor, wherein the servo motor is operable to actuate the needle relative to the cannula, wherein the actuation assembly further comprises a servo controller in communication with the microscope imaging detector, wherein the servo controller is operable to control the servo motor based on light detected by the microscope imaging detector.

Example 20

A system for delivering therapeutic agent to an eye, wherein the system comprises: (a) a surgical instrument, wherein the surgical instrument comprises: (i) a body, (ii) a cannula extending distally from the body, wherein the cannula is sized and configured to be insertable between a choroid and a sclera of a patient's eye, wherein the cannula defines a longitudinal axis, (iii) a hollow needle, wherein the needle is slidable relative to the cannula, and (iv) an actuation assembly, wherein the actuation assembly is operable to actuate the needle relative to the cannula to thereby drive a distal portion of the needle along an exit axis; and (b) a detection or visualization system, wherein a portion of the detection or visualization system is coupled with a distal end of the needle such that the detection or visualization system is operable to slide concurrently with the needle within the cannula, wherein the detection or visualization system is operable to detect or visualize penetration of a choroid of a patient's eye.

VII. Miscellaneous

It should be understood that any of the versions of the instruments described herein may include various other features in addition to or in lieu of those described above. By way of example only, any of the devices herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A system for delivering therapeutic agent to an eye, wherein the system comprises:
   (a) a surgical instrument, wherein the surgical instrument comprises:
      (i) a body,
      (ii) a cannula extending distally from the body, wherein the cannula is sized and configured to be insertable between a choroid and a sclera of a patient's eye, wherein the cannula defines a longitudinal axis,
      (iii) a hollow needle having a sharp distal tip, wherein the needle is slidable relative to the cannula, and
      (iv) an actuation assembly, wherein the actuation assembly is operable to actuate the needle relative to the cannula to thereby drive a distal portion of the needle along an exit axis; and
   (b) an interferometer system comprising:
      (i) a light source,
      (ii) an optical fiber in communication with the light source, and
      (iii) an optical probe coupled with a distal end of the optical fiber, wherein the optical probe is coupled with a distal portion of the hollow needle such that a central axis of the optical probe is laterally offset from a central axis of the distal portion of the hollow needle, wherein the optical probe is operable to slide concurrently with the hollow needle within the cannula,
      wherein the optical probe is configured to project light onto tissue and receive light reflected back from the tissue such that the interferometer system is operable to provide data indicating a position of the distal tip of the hollow needle within a patient's eye.

2. The system of claim 1, wherein the optical probe comprises a gradient-index (GRIN) lens.

3. The system of claim 1, wherein the exit axis is oriented obliquely relative to the longitudinal axis of the cannula.

4. The system of claim 1, wherein the interferometer system comprises a spectrometer.

5. The system of claim 1, wherein the interferometer system is operable to provide an operator with an optical coherence tomography (OCT) scan that depicts sub-surface layers of the eye, wherein the system further comprises a display operable to depict the OCT scan of the interferometer.

6. The system of claim 1, wherein the interferometer system comprises a dispersive white-light interferometer (D-WLI).

7. The system of claim 1, wherein the interferometer system comprises a display operable to depict a choroid and a retina of a patient's eye.

8. The system of claim 1, wherein the optical probe of the interferometer system is coupled with the distal portion of the hollow needle via an adhesive layer.

9. The system of claim 1, wherein the interferometer system is operable to provide visual, audible, and/or tactile feedback to an operator in response to the hollow needle piercing the choroid.

10. The system of claim 1, wherein the interferometer system comprises a position tracking system.

11. The system of claim 1, wherein the optical probe is positioned proximally relative to the distal tip of the needle.

12. The system of claim 1, wherein the optical probe is oriented substantially parallel to the needle.

13. The system of claim 1, wherein the optical probe is coupled to an exterior side surface of the hollow needle.

14. A system for delivering therapeutic agent to an eye, wherein the system comprises:
   (a) a surgical instrument, wherein the surgical instrument comprises:
      (i) a body,
      (ii) a cannula extending distally from the body, wherein the cannula is sized and configured to be insertable between a choroid and a sclera of a patient's eye, wherein the cannula defines a longitudinal axis,
      (iii) a hollow needle having a sharp distal tip, wherein the needle is translatable relative to the cannula,
      (iv) a light-emitting fiber optic cable, wherein the fiber optic cable is operable to emit light into the patient's eye through a retina thereof, and
      (v) an actuation assembly, wherein the actuation assembly is operable to actuate the needle relative to the cannula to thereby drive a distal portion of the needle along an exit axis;
   (b) a microscope positionable adjacent to a cornea of the patient's eye, wherein the microscope is operable to receive light emitted from the fiber optic cable as the light exits the patient's eye through a pupil thereof; and
   (c) an image sensor operatively connected with the microscope, wherein the image sensor is operable to detect that the light received by the microscope exceeds a threshold light intensity associated with the distal tip of the needle reaching a subretinal space in the patient's eye.

15. The system of claim 14, wherein the fiber optic cable is coupled with a distal portion of the hollow needle such that the fiber optic cable is operable to slide concurrently with the hollow needle within the cannula.

16. The system of claim 14, wherein in response to the image sensor detecting that the received light exceeds the threshold light intensity, the system is operable to at least one of:
   (a) provide an indication to a user, or
   (b) cease translation of the needle relative to the cannula.

17. The system of claim 14, wherein the actuation assembly comprises a servo motor, wherein the servo motor is operable to drive translation of the needle relative to the cannula, wherein the actuation assembly further comprises a servo controller in communication with the image sensor, wherein the servo controller is operable to control the servo motor to cease translation of the needle in response to detection by the image sensor that the received light exceeds the threshold light intensity.

18. The system of claim 14, wherein the microscope comprises:
(i) a beam splitter, and
(ii) a view port,
wherein the microscope is configured to receive light emitted from the fiber optic cable through the patient's eye, wherein the beam splitter is operable to separate the received light into a first light beam viewable by a user through the view port, and a second light beam directed to the image sensor,
wherein the image sensor is operable to detect that the second light beam exceeds the threshold light intensity associated with the distal tip of the needle reaching a subretinal space in the patient's eye.

19. A system for delivering therapeutic agent to an eye, wherein the system comprises:
(a) a surgical instrument, wherein the surgical instrument comprises:
(i) a body,
(ii) a cannula extending distally from the body, wherein the cannula is sized and configured to be insertable between a choroid and a sclera of a patient's eye, wherein the cannula defines a longitudinal axis,
(iii) a hollow needle having a sharp distal tip, wherein the needle is slidable relative to the cannula, and
(iv) an actuation assembly, wherein the actuation assembly is operable to actuate the needle relative to the cannula to thereby drive a distal portion of the needle along an exit axis; and
(b) a detection or visualization system having:
(i) an optical fiber, and
(ii) an optical probe at a distal end of the optical fiber, wherein the optical probe is configured to project light onto tissue and receive light reflected back from the tissue,
wherein the optical fiber and the optical probe are fixedly disposed along an exterior side surface of a distal portion of the needle and are operable to slide concurrently with the needle within the cannula, wherein the detection or visualization system is operable to detect or visualize penetration of the choroid of the patient's eye.

20. The system of claim 19, wherein the optical fiber and the optical probe are fixed relative to the exterior side surface of the needle with an adhesive element.

* * * * *